US012678454B2

(12) United States Patent
Brown et al.

(10) Patent No.: US 12,678,454 B2
(45) **Date of Patent: *Jul. 14, 2026**

(54) BICARBONATE AS A POTENTIATOR FOR ANTIMICROBIAL AGENTS

(71) Applicant: MCMASTER UNIVERSITY, Hamilton (CA)

(72) Inventors: Eric Brown, Oakville (CA); Maya Farha, Ancaster (CA); Craig MacNair, Ancaster (CA)

(73) Assignee: McMaster University, Hamilton (CA)

( * ) Notice: Subject to any disclaimer, the term of this patent is extended or adjusted under 35 U.S.C. 154(b) by 288 days.

This patent is subject to a terminal disclaimer.

(21) Appl. No.: 18/236,164

(22) Filed: Aug. 21, 2023

(65) Prior Publication Data

US 2023/0390328 A1 Dec. 7, 2023

Related U.S. Application Data

(60) Continuation-in-part of application No. 17/157,118, filed on Jan. 25, 2021, now Pat. No. 11,779,595, which is a division of application No. 15/887,469, filed on Feb. 2, 2018, now Pat. No. 10,940,163.

(60) Provisional application No. 62/524,866, filed on Jun. 26, 2017, provisional application No. 62/483,032, filed on Apr. 7, 2017, provisional application No. 62/453,701, filed on Feb. 2, 2017.

(51) Int. Cl.

| | |
|---|---|
| ***A61K 33/00*** | (2006.01) |
| ***A61K 31/431*** | (2006.01) |
| ***A61P 31/04*** | (2006.01) |
| ***A61P 31/10*** | (2006.01) |
| ***A61P 31/16*** | (2006.01) |
| ***A61P 31/18*** | (2006.01) |
| ***A61P 31/22*** | (2006.01) |
| ***A61P 33/02*** | (2006.01) |

(52) U.S. Cl.
CPC .............. *A61K 33/00* (2013.01); *A61P 31/04* (2018.01); *A61P 31/10* (2018.01); *A61P 31/16* (2018.01); *A61P 31/18* (2018.01); *A61P 31/22* (2018.01); *A61P 33/02* (2018.01); *A61K 31/431* (2013.01); *A61K 2300/00* (2013.01); *Y02A 50/30* (2018.01)

(58) Field of Classification Search
CPC ................ A61K 33/10; A61K 31/7036; A61K 31/7048; A61P 31/04
See application file for complete search history.

(56) References Cited

U.S. PATENT DOCUMENTS

| | | | | |
|---|---|---|---|---|
| 4,328,245 | A | 5/1982 | Yu et al. | |
| 4,409,239 | A | 10/1983 | Yu | |
| 4,410,545 | A | 10/1983 | Yu et al. | |
| 6,159,458 | A | 12/2000 | Bowman et al. | |
| 6,239,113 | B1 | 5/2001 | Dawson et al. | |
| 6,350,458 | B1 | 2/2002 | Modi | |
| 6,569,443 | B1 | 5/2003 | Dawson et al. | |
| 6,861,411 | B1 | 3/2005 | Ahmed | |
| 6,984,403 | B2 | 1/2006 | Hagen | |
| 7,056,893 | B2 | 6/2006 | Roy et al. | |
| 9,198,862 | B2 | 12/2015 | Pilgaonkar et al. | |
| 10,940,163 | B2 | 3/2021 | Brown et al. | |
| 11,779,595 | B2 * | 10/2023 | Brown | A61P 31/22 424/717 |
| 2003/0143259 | A1 | 7/2003 | Roy et al. | |
| 2009/0062221 | A1 | 3/2009 | Dow | |
| 2010/0273748 | A1 | 10/2010 | Gallo et al. | |
| 2015/0141328 | A1 * | 5/2015 | Sullivan | A61K 31/568 514/11.3 |
| 2018/0243333 | A1 * | 8/2018 | Brown | A61P 31/16 |

FOREIGN PATENT DOCUMENTS

| | | | |
|---|---|---|---|
| CA | 2159984 | | 10/1994 |
| CN | 101703465 | | 5/2010 |
| CN | 102283799 | B | 7/2013 |
| CN | 104447918 | | 3/2015 |
| CN | 105010307 | A | 11/2015 |
| CN | 107 998 399 | A | 5/2018 |
| EP | 0778021 | A1 | 6/1997 |
| WO | 2011/125075 | A2 | 10/2011 |
| WO | 2018141063 | A1 | 8/2018 |

OTHER PUBLICATIONS

Corral et al (Journal of Food Science, 1988, vol. 53, pp. 981-982) (Year: 1988).*
Opitz et al. (Ophthalmology and Eye Disease, 2012, pp. 1-14) (year: 2012).
Barankowski et al. (The Scientific World Journal, 2014, vol. 2014, p. 1-14) (year: 2014).
Marvola et al. "Bioavailability of Erythromycin Acistrate from Hard Gelatin Capsules Containing Sodium Bicarbonate," Pharmaceutical Research 8(8): 1056-1058 (1991).
Dinshaw (McMaster University, 2022 http://healthsci.mcmaster.ca/home/2022/05/16mcmasteruniversity-entrepreneur-uses-baking-soda-to-supercharge-antibiotic) (year:2022).
Yang et al. (Frontiers in Microbiology, Oct. 2016, vol. 7, pp. 1-8) (year:2016).
Farha et al. (ACS Infectious diseases, 2020, vol. 6, pp. 2709-2718, abstract) (year:2020).

(Continued)

*Primary Examiner* — Mark V Stevens
(74) *Attorney, Agent, or Firm* — Gowling WLG (Canada) LLP

(57) ABSTRACT

Provided herein are methods and compositions for modulating a microorganism's response to an antimicrobial agent. In one embodiment, the method comprises contacting the microorganism with an antimicrobial agent and bicarbonate. In one embodiment, provided herein are methods for treating a microbial infection comprising administering to a subject in need an effective amount of (i) bicarbonate and (ii) an antimicrobial agent. Also provided herein are methods of screening for antimicrobial compounds.

18 Claims, 28 Drawing Sheets

(56) References Cited

OTHER PUBLICATIONS

Baba et al., "Construction of *Escherichia coli* K-12 in-frame, single-gene knockout mutants: the Keio collection," Mol Syst Biol 2, pp. 1-11 (2006).
Bakker and Mangerich, "Interconversion of components of the bacterial proton motive force by electrogenic potassium transport," J Bacteriol 1981, 147: 820-826 (1981).
Berge et al., "Pharmaceutical Salts," J. Pharm. Sci. 66(1):1-19 (1977).
Bowman et al., "Development of a Topical Polymeric Mucoadhesive Ocular Delivery System for Azithromycin," Journal of Ocular Pharm and Therapeutics 25(2):133-139 (2009).
Ejim et al., "Combinations of antibiotics and nonantibiotic drugs enhance antimicrobial efficacy," Nature chemical biology 7:348-350 (2011).
Ersoy et al., "Correcting a Fundamental Flaw in the Paradigm for Antimicrobial Susceptibility Testing," EBioMedicine 20:173-181 (2017).
Farha et al. "Bicarbonate Alters bacterial Susceptibility to Antibiotics by Targeting the Proton Motive Force," ACS Infectious Diseases, pp. A-I (2017).
French et al., "A robust platform for chemical genomics in bacterial systems," Mol Biol Cell 27:1015-1025 (2016).
Gutierrez-Huante et al., "Bicarbonate enhances the in-vitro antibiotic activity of kanamycin in *Escherichia coli*," Letters in Applied Microbiology 60:440-446 (2015).
Kaushik et al., "Tobramycin and Bicarbonate synergise to kill planktonic Pseudomonas aeruginosa, but antagonise to promote biofilm survival," NPJ Biofilms Microbiomes 2:16006 (2016), 21 pages.
Keseler et al., "EcoCyc: fusing model organism databases with systems biology," Nucleic Acids Res 41:D605-D612 (2013).
Ko et al., "Influence of Zinc, Sodium Bicarbonate, and Citric Acid on the Antibacterial Activity of Ovotransferrin Against *Escherichia coli* 0157:H7 and Listeria monocytogenes in Model Systems and Ham," Poultry Science 87:2660-2670 (2008).
Letscher-Bru et al., "Antifungal Activity of Sodium Bicarbonate against Fungal agent causing superficial infections," Mycopathologia 175:153-158 (2013).
Lobritz et al., Antibiotic efficacy is linked to bacterial cellular respiration. Proc Natl Acad Sci USA 112:8173-8180 (2015).
Mangat et al., "Rank ordering plate data facilitates data visualization and normalization in high-throughput screening," J Biomol Screen 19:1314-1320 (2014).
Martinez-Duncker, et al., "Bicarbonate has Varied Effect on the In Vitro Activity of Antibiotics in *Escherichia coli*," Interscience Conference on Antimicrobial Agents and Chemotherapy (ICAAC), San Diego, CA, Abstract C-616, 2 pages (Sep. 19, 2015).
Miyasaki et al., "Antimicrobial Properties of Hydrogen Peroxide and Sodium bicarbonate Individually and in Combination against Selected Oral, Gram-negative, Facultative Bacteria," J. Dent. Res. 65(9):1142-1148 (1986).
Mobley et al., "Erythromycin plus sodium bicarbonate in chronic bacterial prostatitis," Urology 3(1):60-62 (1974).
Newbrun et al., "Bactericidal Action of Bicarbonate Ion on selected periodontal pathogenic microorganisms," J. Periodontol. 55(11):658-667 (1984).
Piddock et al., "Quinolone accumulation by *Pseudomonas aeruginosa, Staphylococcus aureus* and *Escherichia coli*," J Antimicrob Chemother 43:61-70 (1999).
Stokes, et al., "Cold Stress Makes *Escherichia coli* Susceptible to Glycopeptide Antibiotics by Altering Outer Membrane Integrity," Cell Chem. Biol. 23(2):267-277 (2016).
Thompson et al., "Antibacterial Activity of Lidocaine in Combination with a Bicarbonate Buffer," J. Dennatol. Surg. Onco. 19:216-220 (1993).
Zasloff, "Antimicrobial Peptides in Health and Disease," N Engl J Med 347: 1199-1200 (2002).
Zhang et al; "Bicarbonate induces high-level resistance to the human antimicrobial peptide LL-37 in *Staphylococcus aureus* small colony variants," Journal of Antimicrobial Chemotherapy 73:615-619 (2018) (Published on Dec. 4, 2017).
Richter et al., "Predictive rules for compound accumulation yield a broad-spectrum antibiotic," Nature. May 18, 2017;545(7654): 299-304.
Promega, Buffers for Biochemical Reactions, copyright 2004-2012, pp. 15-1 to 15-5 (Year: 2012).
Dorschner et al., "The Mammalian lonic Environment Dictates Microbial Susceptibility to Antimicrobial Defense Peptides," The FASEB Journal, vol. 20, 8 pages (2006).
Ersoy et al., "Bicarbonate Resensitization of Methicillin-Resistant *Staphylococcus aureus* top-Lactam Antibiotics," Antimicrob. Ag. Chemother., 63(7):e00496-19, pp. 1-16 (2019).
Sigma Life Science (Cell Culture Manual, 2011-2014, pp. 1-380) (2014).
Vytone webpage. dated May 7, 2019, retrieved July 9. 2019. at https://www.drugs.com/cdi/vytone.html, 4 pages.
Xolegel CorePak webpage, dated Feb. 9, 2019, retrieved Jul. 9, 2019, at https:/Avww.drugs.com/cdi/xolegel-corepak.html, 5 pages.
Erymed, retrieved Jul. 11, 2019, at https:/Avww.ndrugs.com/?s=crymed%20plus&t=side%20effects, 4 pages.
Gentamicin 0.3%—Eye drops, Patient Leaflet, Mar. 2014, retrieved Jul. 11, 2019, at https://www.medicines.org.uk/emc/files/pil.6552.pdf, one page.
Gentamicin Otic, 2019, retrieved Jul. 11, 2019, at https://www.drugs.com/cons/gentamicin-otic.html, 4 pages.
Diver et al., "The accumulation of five quinolone antibacterial agents by *Escherichia coli*." J Antimicrob Chemother 25:319-333 (1990).
Zaslaver A. et al., "A comprehensive library of fluorescent transcriptional reporters for *Escherichia coli*," Nat Methods 3:623-628 (2006).
Melissa Archer and Gary Oderda, "Otic Antibiotic-Corticosteroid Drug Class Review," University of Utah College of Pharmacy, University of Utah College of Pharmacy, Feb. 2013, 12 pages.
Prednisolone Ophthalmic Package Insert, Mar. 2014, 7 pages.
AzaSite (azithromycin ophthalmic solution) Prescribing Information, Jul. 2012, 12 pages.
Altabax (retapamulin ointment) prescribing information, Dec. 2012, 12 pages.
Altargo (retapamulin), Product Monograph, Aug. 2018, retrieved Jul. 10, 2019 at https://au.gsk.com/media/212995/altargo cmi au 002 approved.pdf, 3 pages.
Bacitracin Ointment, Updated Oct. 18, 2016, retrieved Jul. 11, 2019, at https://dailymed.nlm.nih.gov/dailymed/drugInfo.cfin?setid=024bc706-2da7-4e41-blbc-60falb351463, 6 pages.
Bactroban Approved Package Insert, 5 pages, dated Dec. 6, 2013.
Besivance Prescribing Information, Apr. 2018, 2 pages.
Ciloxan, dated Nov. 2018, retrieved Jul. 11, 2019, at haps : //dailymed.nlm.nih.govklailyme d/drugInfo.cfin?setid=1c29270 6-a900-4d6f-979e-9c42d6ff2fb2, 7 pages.
Cipro HC, Updated Nov. 14, 2018, retrieved Jul. 11, 2019, at https://dailymed.nlm.nih.gov/dailymed/drugInfo.cfm?setid=70b19501-34b6-4f95-a8dd-dd3e67d22399, 7 pages.
Ciprodex Prescribing Information, Feb. 2019, 13 pages.
Clindamycin 1%, Updated May 9, 2019, retrieved Jul. 11, 2019, at https://dailymed.nlm.nih.gov/dailymed/ drugInfo.cfm?setid=887a3793-15 2c-6 b 7 f-e053-2a95a90ab09b, 8 pages.
Cochereau et al., "3-day treatment with azithromycin 1.5% eye drops versus 7-day treatment with tobramycin 0.3% for purulent bacterial conjunctivitis: multicentre, randomised and controlled trial in adults and children," Br J. Ophthalmol 91:465-469 (2007).
Coly-mycin, dated Feb. 2016, retrieved Jul. 11, 2019, at https://dailymed.nlm.nih.gov/dailymed/drugInfo.cfm?setid=256f4083-5b34-4643-a75a-ddla59a5d964, 9 pages.
Cortisporin TC Otic description, dated Jan. 15, 2019, retrieved Jul. 11, 2019, at https://dailymed.nlm.nih.gov/dailymed/drugInfo.cfm?setid=9c6fcic7-3350-42ae-b999-aca48e704bb1, 9 pages.
Eryacne Package Leaflet: Information for the User, approved Sep. 2009, retrieved Jul. 11, 2019, at https://www.drugs.com/uk/eryacne-4-leaflet.html, 2 pages.

(56) References Cited

OTHER PUBLICATIONS

Erythromycin, dated Jul. 2017, retrieved Jul. 11, 2019, at https://dailymed.nlm.nih.gov/dailymed/drugInfo.cfm?setid=b21d02ea-5394-4f88-8d2b-3a8cd6e807a0, 5 pages.
Floxin OTIC, dated Aug. 24, 2009, retrieved Jul. 11, 2019 at https://dailymed.nlm.nih.gov/dailymed/drugInfo.cfm?setid=b4968de4-3644-953a-d5d1-28f029cb4175, 13 pages.
Fusidic Acid Cream Package Leaflet, dated Jul. 2016, retrieved Jul. 10, 2019, at https://www.drugs.comiukfiusidic-acid-20-mg-g-cream-leaflet.html, 2 pages.
Gatifloxacin, dated May 3, 2018, retrieved Jul. 11, 2019, at https://dailymed.nlm.nih.gov/dailymed/drugInfo.cfin?setid=14312de6-67d4-4de2-854c-ef764090dd83, A88, 9 pages.
Gentamicin, dated Sep. 26, 2013, retrieved Jul. 11, 2019 at https://dailymed.nlm.nih.gov/dailymed/drugInfo.cfm?setid=84f5c763-1cd3-4d85-9afb-934db8666fbf, 13 pages.
Kugelberg et al., "Establishment of a Superficial Skin Infection Model in Mice by Using *Staphylococcus aureus* and *Streptococcus pyogenes*," Antimicrobial Agents and Chemotherapy 49(8):3435-3441 (2005).
Marquardt, "Animal Models of Bacterial Keratitis," Hindawi Publishing Corporation, Journal of Biomedicine and Biotechnology, vol. 2011, Article ID 680642, 12 pages (2011.
Neosporin, dated Oct. 3, 2006, retrieved Jul. 11, 2019, at https://dailymed.nlm.nih.gov/dailymed/drugInfo.cfin?setid=7e971c99-1f3f-4a9f-5084-fbe5b9f1a9e1, 5 pages.
Neosporin (Bacitracin, Neomycin, and Polymyxin B, Pramoxine hcl), dated Jun. 8, 2017, retrieved Jul. 11, 2019, at https://dailymed.nlm.nih.gov/dailymed/drugInfo.cfm?setid=41c49d4f-201e-4aa9-b6a6-ea6ledaf9530, 4 pages.
Ocuflox, dated Apr. 14, 2017, retrieved Jul. 11, 2019 at https://dailymed.nlm.nih.gov/dailymed/drugInfo.cfin?setid=7aab4449-3dda-4e2c-8e40-b3244a548bf5, 8 pages.
Okamycin webpages, dated 2017, retrieved Jul. 11, 2019, at http://wwwv.instantremedies.net/okamycin-500, 3 pages.
Opitz and Harthan, "Review of Azithromycin Ophthalmic 1% solution (Azasite®) for the Treatment of Ocular Infections," Ophthalmology and Eye Diseases 4:1-14 (2012).
Otiprio Prescribing Information, dated Mar. 2018, retrieved Jul. 10, 2019, at https://otiprio.com/prescribing-information.pdf, 4 pages.
Otovel Prescribing Information, Apr. 2016, 20 pages.
Polymyxin B, dated Jun. 21, 2011, retrieved Jul. 11, 2019, at https://www.accessdata.fda.gov/drugsatfda_docs/label/2012/060716Orig1s020Lbl.pdf, 3 pages.
Polysporin, dated Dec. 1, 2016, retrieved Jul. 11, 2019, at https://dailymed.nlm.nih.gov/dailymed/drugInfo.cfm?setid=e0fcf83e-a374-4fc0-a629-873033054392, 4 pages.
Quixin Prescribing Information, dated Aug. 1, 2018, retrieved Jul. 11, 2019, at https://www.drugs.com/pro/quixin.html, 8 pages.
Sulfamethoxazole and Trimethoprim, dated Dec. 30, 2013, retrieved Jul. 11, 2019, at https://dailymed.nlm.nih.gov/dailymed/drugInfo.cfm?setid=804f8363-8eal-4a57-bbd1-7fd9b6b4d29b, 16 pages.
TobraDex (tobramycin and dexamethasone ophthalmic suspension) sterile, (May 2018), 4 pages.
Tobrex, dated Dec. 3, 2018, retrieved Jul. 11, 2019, at https://dailymed.nlm.nih.gov/dailymed/drugInfo.cfm?setid=cdd42 3 c 5-a2 31-47d4-bf51-00b5c29e6a60, 6 pages.
Vigamox Product Monograph including Patient Medication Information (Moxifloxacin Ophthalmic Solution), dated Dec. 1, 2017, 27 pages.
Zineryt Package Leaflet, dated, retrieved online Jul. 11, 2019, at https://www.medicines.org.uk/emc/files/pil.5488.pdf, 2 pages.
Ala-Quin webpage, dated Jun. 5, 2019, retrieved online Jul. 9, 2019 at https://www.drugs.com/mtm/ala-quin.html, 4 pages.
Mycolog II webpage, dated Dec. 3, 2018, retrieved online Jul. 9, 2019 at https://www.drugs.com/mtm/mycolog-ii-topical.html, 4 pages.
Xerese Cream webpage, dated Jun. 5, 2019, retrieved Jul. 9, 2019 at https://www.drugs.comixerese.html, 4 pages.
Lotrisone webpage, dated Apr. 28, 2019, retrieved Jul. 9, 2019, at https://www.drugs.com/lotrisone.html, 4 pages.
Alcortin webpage, dated Jan. 14, 2019, retrieved Jul. 9, 2019, at https://www.drugs.com/mtm/alcortin-a-topical.html, 4 pages.
Cortisporin Cream webpage, dated Apr. 1, 2018, retrieved Jul. 9, 2019, at https://www.drugs.com/pro/cortisporin-cream.html, 8 pages.
Cortisporin Ointment webpage, dated Apr. 1, 2018, retrieved Jul. 9, 2019, at https://www.drugs.com/pro/cortisporin-ointment.html, 9 pages.
Dermazene webpage, dated May 7, 2019, retrieved Jul. 9, 2019, at https://www.drugs.com/cdi/dermazene.html, 4 pages.
Mytrex webpage, dated Dec. 3, 2018, retrieved Jul. 9, 2019, at https://www.drugs.com/mtm/mytrex-topical.html, 4 pages.
Neo-Synalar webpage, dated Nov. 16, 2018, retrieved Jul. 9, 2019, at https://www.drugs.com/mtm/neo-synalar.html, 4 pages.

* cited by examiner

3A

3B

8A

8B

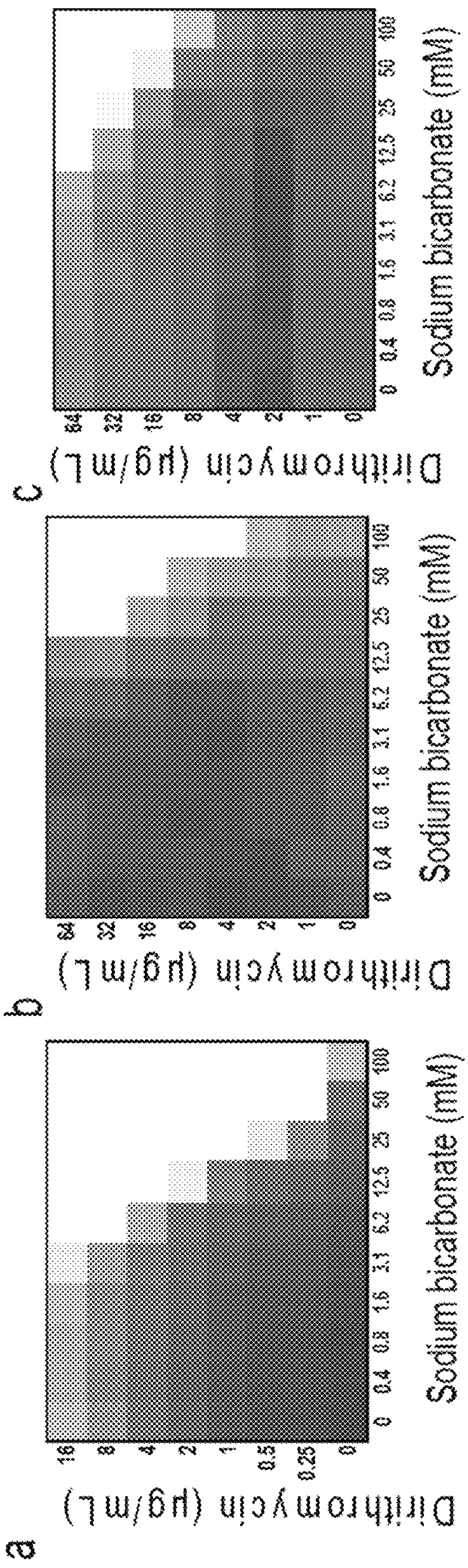
FIG. 8C, Panels a-c

FIG. 10, Panels a-h

FIG. 11, Panels a-c

FIG. 13, Panels a-b

FIG. 17, Panels a-b

FIG. 18, Panels a-c

FIG. 19, Panels a-b

FIG. 21, Panels a-b

BICARBONATE AS A POTENTIATOR FOR ANTIMICROBIAL AGENTS

This application is a continuation-in-part application of U.S. application Ser. No. 17/157,118 filed Jan. 25, 2021, which is a divisional application of U.S. application Ser. No. 15/887,469 filed Feb. 2, 2018 and granted as U.S. Pat. No. 10,940,163, which claims the benefit of U.S. Provisional Patent Application No. 62/524,866, filed Jun. 26, 2017, U.S. Provisional Patent Application No. 62/483,032, filed Apr. 7, 2017 and U.S. Provisional Patent Application No. 62/453,701, filed Feb. 2, 2017, each of which is incorporated by reference herein in its entirety.

FIELD OF THE INVENTION

The present application relates to the activity of bicarbonate as a modulator of antimicrobial agents, and in particular the use of sodium bicarbonate as a modulator of antibiotics.

BACKGROUND OF THE INVENTION

There has been a steady increase in the use of antimicrobial agents, such as antibiotics and anti-fungal agents. Over the past 20 years, there has been an explosion in the prevalence of antibiotic resistant bacterial infections, both in the hospital and in the general community. Notably, the ESKAPE pathogens (*Enterococcus faecium, Staphylococcus aureus, Klebsiella pneumoniae, Acinetobacter baumannii, Pseudomonas aeruginosa*, and *Enterobacter* species) are responsible for a substantial percentage of nosocomial infections and present serious therapeutic challenges for physicians. These multi-drug resistant infections increase morbidity and mortality and undoubtedly, require broad-spectrum antimicrobial coverage, or the increased usage of antibiotics.

Needed are ways than can further modulate the response of microorganisms to various antimicrobial agents, in order to achieve control of activity of antimicrobial agents, useful in various contexts.

For example, needed are methods to potentiate the response of a microorganism to an antimicrobial agent, allowing for either a greater response at a given concentration of the antimicrobial agent, or an increased response at a lower concentration of the antimicrobial agent. This could, for example, establish a way by which to preserve the efficacy of existing antibiotics that may work better in a host than originally thought or a means to afford novel and alternate clinical indications.

SUMMARY OF THE INVENTION

The invention provides methods for inhibiting the growth of a virus, a bacterium, a fungus or a parasite, comprising contacting the virus, the bacterium, the fungus or the parasite with an effective amount of (i) bicarbonate and (ii) an antimicrobial agent;

wherein the bacterium is:

(a) a spiral-shaped bacterium, a filamentous bacterium, a pleomorphic bacterium or a rectangular bacterium;

(b) an obligate aerobe or an obligate anaerobe;

(c) a Gram positive rod-shaped bacterium;

(d) a Gram negative sphere-shaped bacterium;

(e) a species of *Acinetobacter, Actinomyces, Aerococcus, Agrobacterium, Anaplasma, Azorhizobium, Azotobacter, Bacillus, Bacteroides, Bartonella, Bordetella,*

*Borrelia, Brucella, Burkholderia, Calymmatobacterium, Campylobacter, Chlamydia, Chlamydophila, Clostridium, Corynebacterium, Coxiella, Ehrlichia, Enterobacter, Enterococcus, Francisella, Fusobacterium, Gardnerella, Haemophilus, Helicobacter, Klebsiella, Lactobacillus, Lactococcus, Legionella, Listeria, Methanobacterium, Microbacterium, Micrococcus, Moraxella, Mycobacterium, Mycoplasma, Neisseria, Pasteurella, Pediococcus, Peptostreptococcus, Porphyromonas, Prevotella, Pseudomonas, Rhizobium, Rickettsia, Rochalimaea, Rothia, Salmonella, Serratia, Shigella, Sarcina, Spirillum, Spirochaetes, Stenotrophomonas, Streptobacillus, Streptococcus, Tetragenococcus, Treponema, Vibrio, Viridans, Wolbachia* or *Yersinia*; or (f) *Staphylococcus epidermidis.*

The invention also provides methods for treating or preventing a microbial infection, comprising administering to a subject in need thereof an effective amount of (i) bicarbonate and (ii) an antimicrobial agent;

wherein the microbial infection is an infection by a virus, a bacterium, a fungus or a parasite; and wherein the bacterium is:

(a) a spiral-shaped bacterium, a filamentous bacterium, a pleomorphic bacterium or a rectangular bacterium;

(b) an obligate aerobe or an obligate anaerobe;

(c) a Gram positive rod-shaped bacterium;

(d) a Gram negative sphere-shaped bacterium;

(e) a species of *Acinetobacter, Actinomyces, Aerococcus, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Clostridium, Corynebacterium, Coxiella, Ehrlichia, Enterobacter, Enterococcus, Francisella, Fusobacterium, Gardnerella, Haemophilus, Helicobacter, Klebsiella, Lactobacillus, Lactococcus, Legionella, Listeria, Methanobacterium, Microbacterium, Micrococcus, Moraxella, Mycobacterium, Mycoplasma, Neisseria, Pasteurella, Pediococcus, Peptostreptococcus, Porphyromonas, Prevotella, Pseudomonas, Rhizobium, Rickettsia, Rochalimaea, Rothia, Salmonella, Serratia, Shigella, Sarcina, Spirillum, Spirochaetes, Stenotrophomonas, Streptobacillus, Streptococcus, Tetragenococcus, Treponema, Vibrio, Viridans, Wolbachia* or *Yersinia*; or (f) *Staphylococcus epidermidis.*

The invention further provides methods for inhibiting the growth of a virus, a bacterium, a fungus or a parasite, comprising contacting the virus, the bacterium, the fungus or the parasite with an effective amount of (i) bicarbonate and (ii) an antimicrobial agent;

wherein the antimicrobial agent is an antiviral agent, an anti-fungal agent, an anti-parasitic agent, an antibiotic agent, or an innate immunity factor;

wherein the antibiotic agent is (a) a macrolide, a tetracycline, a cephalosporin, a quinolone, a rifampin or a fluoroquinolone; or (b) Amoxicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, or a pharmaceutically acceptable salt thereof; and wherein the innate immunity factor is an antimicrobial enzyme or an antimicrobial secretion.

The invention further provides methods for treating or preventing a microbial infection, comprising administering to a subject in need thereof an effective amount of (i) bicarbonate and (ii) an antimicrobial agent;

wherein the microbial infection is an infection by a virus, a bacterium, a fungus or a parasite;

wherein the antimicrobial agent is an antiviral agent, an anti-fungal agent, an anti-parasitic agent, an antibiotic agent, or an innate immunity factor;

wherein the antibiotic agent is (a) a macrolide, a tetracycline, a cephalosporin, a quinolone, a rifampin or a fluoroquinolone; or (b) Amoxicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, or a pharmaceutically acceptable salt thereof; and wherein the innate immunity factor is an antimicrobial enzyme or an antimicrobial secretion.

The invention further provides methods for modulating a microorganism's response to an antimicrobial agent, comprising contacting a microorganism with an antimicrobial agent in the presence of bicarbonate, wherein the antimicrobial agent is an antibiotic, and wherein the antibiotic is a macrolide, tetracycline, peptide, glycopeptide, penicillin, cephalosporin, quinolone, fluoroquinolone, rifampin, an innate immunity factor or an antifungal agent.

The invention further provides methods for modulating a microorganism's response to an antimicrobial agent, comprising contacting a microorganism with an antimicrobial agent in the presence of bicarbonate, wherein the antimicrobial agent is not an aminoglycoside, kanamycin, gentamicin, LL-37, or pharmaceutically acceptable salts thereof.

The invention further provides methods for modulating a microorganism's response to an antimicrobial agent, comprising contacting a microorganism with the antimicrobial agent in the presence of bicarbonate, wherein the antimicrobial agent is pentamidine, indolicidin, bactenesin, alpha-defensin, bile salts, lysozyme, protegrin, hyaluronic acid, chloramphenicol, dirithromycin, erythromycin, doxycycline, tetracycline, linezolid, bacitracin, fosfomycin, fosmidomycin, ampicillin, amoxicillin, cloxacillin, piperacillin, oxacillin, ceftriaxone, cefoperazone, vancomycin, polymyxin B, ciprofloxacin, besifloxacin, enoxacin, nalidixic acid, norfloxacin, levofloxacin, moxifloxacin, pefloxin, novobiocin, rifampicin, trimethoprim or sulfamethoxazole, or a pharmaceutically acceptable salts thereof.

The invention further provides methods for modulating a microorganism's response to an antimicrobial agent comprising contacting a microorganism with an antimicrobial agent in the presence of bicarbonate, wherein the antimicrobial agent is pentamidine, indolicidin, bactenesin, alpha-defensin, bile salts, lysozyme, protegrin, hyaluronic acid, apramycin, neomycin, paromycin, spectinomycin, chloramphenicol, dirithromycin, erythromycin, doxycycline, tetracycline, linezolid, bacitracin, fosfomycin, fosmidomycin, ampicillin, amoxicillin, cloxacillin, piperacillin, oxacillin, ceftriaxone, cefoperazone, vancomycin, polymyxin B, ciprofloxacin, besifloxacin, enoxacin, nalidixic acid, norfloxacin, levofloxacin, moxifloxacin, pefloxin, novobiocin or rifampicin, or a pharmaceutically acceptable salt thereof.

The invention further provides compositions comprising: an effective amount of (i) bicarbonate and (ii) an antimicrobial agent.

The invention further provides compositions comprising: an effective amount of (i) bicarbonate and (ii) an antimicrobial agent;

wherein the antimicrobial agent is an antiviral agent, an antibiotic agent, an anti-fungal agent, an anti-parasitic agent or an innate immunity factor; and wherein the antibiotic agent is (a) a macrolide, a tetracycline, a cephalosporin, a quinolone or a fluoroquinolone; or (b) Amikacin, Neomycin, Tobramycin, Paromomycin, Streptomycin, Spectinomycin, Ertapenem, Doripenem, Imipenem/Cilastatin, Meropenem, Cefadroxil, Cefazolin, Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Teicoplanin, Vancomycin, Telavancin, Clindamycin, Lincomycin, Lipopeptide, Daptomycin, Azithromycin, Clarithromycin, Dirithromycin, Erythromycin, Roxithromycin, Troleandomycin, Telithromycin, Spiramycin, Aztreonam, Linezolid, Posizolid, Radezolid, Torezolid, Amoxicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Bacitracin, Colistin, Polymyxin B, Besifloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Sulfonamidochrysoidine, Demeclocycline, Doxycycline, Minocycline, Oxytetracycline, Tetracycline, Arsphenamine, Chloramphenicol, Fosfomycin, Fusidic acid, Metronidazole, Mupirocin, Platensimycin, Quinupristin/Dalfopristin, Thiamphenicol, Tigecycline, Tinidazole, Trimethoprim, Clofazimine, Dapsone, Capreomycin, Cycloserine, Ethambutol, Ethionamide, Isoniazid, Pyrazinamide, Rifampicin, Rifabutin, Rifapentine or Streptomycin, or a pharmaceutically acceptable salt thereof.

The invention further provides methods of potentiating the activity of an antimicrobial agent, comprising administering to a subject in need thereof an effective amount of (i) bicarbonate and (ii) an antimicrobial agent, wherein the antimicrobial agent is an antimicrobial agent whose concentration in a cell of the microorganism is increased by one or both of (1) decrease in pH gradient across the microorganism's cytoplasmic membrane; and (2) increase in the microorganism's cytoplasmic membrane potential.

The invention further provides compositions comprising sodium bicarbonate and an antimicrobial agent wherein the antimicrobial agent's concentration in a cell of the microorganism is increased by one or both of (1) decrease in pH gradient across the microorganism's cytoplasmic membrane; and (2) increase in the microorganism's cytoplasmic membrane potential.

The invention further provides methods of treating a microbial infection, or a disease, disorder or condition arising from a microbial infection, comprising administering, to a subject in need thereof, an effective amount of (i) bicarbonate and (ii) an antimicrobial peptide, an antimicrobial enzyme, or an antimicrobial secretion.

The invention further provides compositions comprising sodium bicarbonate and an antimicrobial peptide, an antimicrobial enzyme, or an antimicrobial secretion.

The invention further provides methods for treating a microbial infection, or a disease, disorder or condition arising from a microbial infection, comprising administering, to a subject in need thereof, an effective amount of (i) bicarbonate and (ii) an antimicrobial agent, wherein the antimicrobial agent targets the membrane potential of a cell.

The invention further provides methods for inhibiting the growth of a bacterium, comprising contacting the bacterium with an effective amount of (i) bicarbonate and (ii) an antimicrobial agent, wherein the antimicrobial agent is azithromycin, and the effective amount of the bicarbonate is a concentration of greater than about 150 mM.

The invention further provides a kit comprising i) a first bicarbonate composition and ii) a second antimicrobial composition, wherein the first composition comprises bicarbonate in an amount of greater than about 150 mM, and the second composition comprises the antimicrobial agent azithromycin.

The invention further provides methods for screening for antimicrobial compounds comprising: (1) contacting a microorganism with a test compound in the presence of bicarbonate; and (2) observing growth of the microorganism, wherein a decrease in the growth of the microorganism in the presence of the test compound compared to in the absence of the test compound indicates that the test compound is an antimicrobial compound.

The invention further provides methods for screening for an antimicrobial compound that can be modulated by bicarbonate comprising: (1) contacting a microorganism with a test compound (i) in the presence of bicarbonate or (ii) not in the presence of bicarbonate; and (2) observing growth of the microorganism, wherein a greater change in the growth of the microorganism with the test compound in the presence of bicarbonate compared to the growth of the microorganism with the test compound not in the presence of bicarbonate indicates that the test compound is an antimicrobial compound that can be modulated by bicarbonate.

Other features and advantages of embodiments provided herein will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

Embodiments of the invention are shown in more depth by the following descriptions of their respective drawings listed below.

FIG. 8C, Panels a-c show the combination of the macrolide, dirithromycin, and sodium bicarbonate against multi-drug resistant clinical isolates of (a) *Acinetobacter baumannii* (b) *Klebsiella pneumoniae* and (c) *Pseudomonas aeruginosa.*

DETAILED DESCRIPTION

Figure 1A:
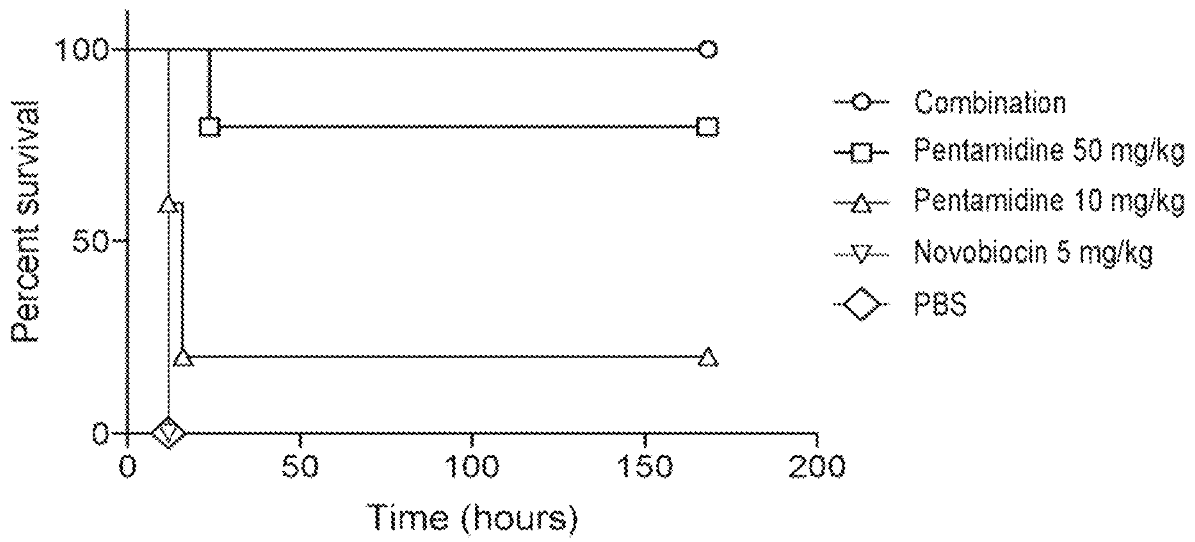
FIG. 1A shows graphically that pentamidine possesses antibacterial activity alone and in the presence of novobiocin.

Provided herein are compositions and methods for modulating a microorganism's response to an antimicrobial agent. The methods comprise contacting a microorganism with an antimicrobial agent in the presence of bicarbonate, whereby the bicarbonate modulates the microorganism's response to the antimicrobial agent.

Also provided herein are compositions and methods for treating a microbial infection, or a disease, disorder or condition arising from a microbial infection. The treatment methods comprise administering to a subject in need thereof, an effective amount of (i) bicarbonate and (ii) an antimicrobial agent.

Also provided herein are methods of screening for antimicrobial agents comprising (1) contacting a microorganism with a test compound in the presence of bicarbonate; and (2) observing growth of the microorganism, wherein a decrease in the growth of the microorganism in the presence of the test compound compared to in the absence of the test compound indicates that the test compound is an antimicrobial agent.

Definitions

Unless otherwise indicated, the definitions and embodiments described in this and other sections are intended to be applicable to all embodiments and aspects of the present invention herein described for which they are suitable as would be understood by a person skilled in the art.

The term "substantially", "about" and "approximately", when immediately preceding a number or numeral, means that the number or numeral ranges plus or minus 10%, and in some embodiments plus or minus 5%.

In embodiments comprising an "additional" or "second" component, such as an additional or second antibiotic, the second component as used herein is chemically different from the other components or first component. A "third" component is different from the other, first, and second components, and further enumerated or "additional" components are similarly different.

The term "microbial infection" as used herein refers to an invasion of cells or bodily tissues by a foreign, undesirable microorganism.

The term "subject" as used herein includes all members of the animal kingdom including mammals, and in some embodiments, to humans. Thus, the methods provided herein are applicable to both human therapy and veterinary applications. In some embodiments, the subject is a mammal. In another embodiment, the subject is human.

The term "pharmaceutically acceptable" means compatible with the treatment of subjects, for example humans.

The term "pharmaceutical composition" as used herein refers to a composition that is suitable for pharmaceutical use.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject. One non-limiting example of such a carrier is a pharmaceutically acceptable oil typically used for parenteral administration.

The term "pharmaceutically acceptable salt" means either an acid addition salt or a base addition salt which is suitable for, or compatible with the treatment of subjects.

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, isethionic, p-toluenesulfonic acid and other sulfonic acids such as methanesulfonic acid, ethanesulfonic acid and 2-hydroxyethanesulfonic acid. Either the mono- or di-acid salts can be formed, and such salts can exist in either a hydrated, solvated or substantially anhydrous form. In general, acid addition salts are more soluble in water and various hydrophilic organic solvents, and generally demonstrate higher melting points in comparison to their free base forms. Other non-pharmaceutically acceptable salts include but are not limited to oxalates.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, EGFRaine, ethylenediamine, glucosamine, methylglucamine, theobromine, purines, piperazine, piperidine, N-ethylpiperidine, polyamine resins, and the like. Illustrative organic bases are isopropylamine, diethylamine, ethanolamine, trimethylamine, dicyclohexylamine, choline, and caffeine. [See, for example, S. M. Berge, et al, "Pharmaceutical Salts," *J. Pharm. Sci.* 1977, 66, 1-19]. The selection of the appropriate salt may be useful so that an ester functionality, if any, elsewhere in a compound is not hydrolyzed. The selection criteria for the appropriate salt will be known to one skilled in the art.

The formation of a desired compound salt is achieved using standard techniques. For example, the neutral compound is treated with an acid or base in a suitable solvent and the formed salt is isolated by filtration, extraction or any other suitable method.

As used herein, the term "effective amount" or "therapeutically effective amount" means an amount effective, at dosages and/or for periods of time necessary to achieve a desired result.

The term "bicarbonate" as used herein refers to a compound of the formula $XHCO_3$, wherein X is a suitable cation. In some embodiments, "bicarbonate" refers to $HCO_3^-$ together with a cation. In some embodiments, a cation is an alkali metal cation. For example, a cation may be sodium, lithium or potassium. In some embodiments, a cation is an alkaline earth metal cation. For example, a cation may be magnesium or calcium. In other embodiments, bicarbonate is ammonium bicarbonate or zinc bicarbonate.

The expression "cytoplasmic membrane potential" as used herein refers to difference in electric potential between the interior and the exterior of a biological cell.

The expression "proton motive force" and "PMF" as used interchangeably herein refers to the measure of the potential energy stored as a combination of proton and voltage (electrical potential) gradients across a membrane. The electrical gradient is a consequence of the charge separation across the membrane (when the protons $H^+$ move without a counterion, such as chloride $Cl^-$).

The expression "psi component of the proton motive force (PMF)" or $\Delta\psi$, as used herein refers to the transmembrane electrical potential, the difference in electrical potential across a membrane.

The term "aminoglycoside" as used herein refers to a class of antibiotic agents that inhibit bacterial protein synthesis and contain, as a portion of the molecule, an amino-modified glycoside (sugar). Aminoglycosides include, but are not limited to, apramycin, gentamicin, kanamycin, neomycin, paromycin, and spectinomycin.

As used herein, the "minimal inhibitory concentration" or "MIC" is the lowest detectable concentration that completely inhibits microbial growth under standard growth conditions.

The term "microorganism", as used herein, refers to an organism that is microscopic. Microorganisms include single-celled and multicellular organisms. Microorganisms include bacteria, archaea, protozoa, algae, fungi, viruses, and multicellular animal parasites (helminths).

The term "potentiating", as used herein, refers to increasing the effect of an antimicrobial agent on a microorganism.

The term "modulating", as used herein, refers to changing (potentiating or lessening) the effect of an antimicrobial agent on a microorganism.

Antimicrobial Agents

The methods provided herein comprise contacting a microorganism with an antimicrobial agent in the presence of bicarbonate. Also provided herein are compositions comprising (a) an effective amount of (i) bicarbonate and (ii) an antimicrobial agent; and, optionally, (b) a pharmaceutically acceptable carrier, diluent or excipient. In some aspects of the methods and compositions described herein, an antimicrobial agent is an antiviral agent, an antibiotic agent, an anti-fungal agent, an anti-parasitic agent or an innate immunity factor. In some embodiments, the methods comprise contacting a microorganism with (i) bicarbonate and (ii) a plurality of different antimicrobial agents.

In some embodiments, the antimicrobial agent causes an increase in the pH gradient across the microorganism's cytoplasmic membrane. In some embodiments, the antimicrobial agent causes a decrease in the pH gradient across the microorganism's cytoplasmic membrane. In some embodiments, the antimicrobial agent causes an increase in the microorganism's cytoplasmic membrane potential. In some embodiments, the antimicrobial agent is a cationic antimicrobial agent, an antimicrobial agent that is an energy dependent efflux substrate, an antimicrobial agent for which entry depends on membrane potential, or an antimicrobial agent that disrupts membrane potential as a primary mechanism of action.

Antibiotics

In some embodiments, an antimicrobial agent is an antibiotic. The terms "antibiotic", "antibiotic agent" and "antibacterial agent" may be used interchangeably.

In some embodiments, the antibiotic is a macrolide, an aminoglycoside, a tetracycline, a peptide, a glycopeptide, a penicillin, a cephalosporin, a quinolone, a fluoroquinolone or a rifampin. An antibiotic may also be a pharmaceutically acceptable salt of any molecule described above, or a combination of these molecules.

In some embodiments, the antibiotic is an aminoglycoside. In some embodiments, the antibiotic is apramycin, gentamicin, kanamycin, neomycin, paromycin, spectinomycin, a combination thereof, or a pharmaceutically acceptable salt thereof. In some embodiments, the antibiotic is not kanamycin or a pharmaceutically acceptable salt thereof. In some embodiments, the antibiotic is not gentamicin or a pharmaceutically acceptable salt thereof. In some embodiments, the antibiotic is not pentamidine or a pharmaceutically acceptable salt thereof.

In some embodiments, the antibiotic is not an aminoglycoside or a pharmaceutically acceptable salt thereof.

In some embodiments the antibiotic is a macrolide. In some embodiments, the antibiotic is dirithromycin, erythromycin, a combination thereof, or a pharmaceutically acceptable salt thereof.

In some embodiment, the antibiotic is not a macrolide or a pharmaceutically acceptable salt thereof.

In some embodiments the antibiotic is a tetracycline or a pharmaceutically acceptable salt thereof. In some embodiments the antibiotic is doxycycline, tetracycline, a combination thereof, or a pharmaceutically acceptable salt thereof.

In some embodiments the antibiotic is not a tetracycline or a pharmaceutically acceptable salt thereof.

In some embodiments the antibiotic is a penicillin or a pharmaceutically acceptable salt thereof. In some embodiments, the antibiotic is ampicillin, amoxicillin, cloxacillin, piperacillin, oxacillin, a combination thereof, or a pharmaceutically acceptable salt thereof.

In some embodiments the antibiotic is not a penicillin or a pharmaceutically acceptable salt thereof. In some embodiments the antibiotic is not ampicillin or a pharmaceutically acceptable salt thereof.

In some embodiments the antibiotic is a quinolone, fluoroquinolone, or a pharmaceutically acceptable salt thereof. In some embodiments, the antibiotic is ciprofloxacin, besifloxacin, enoxacin, nalidixic acid, norfloxacin, levofloxacin, moxifloxacin, pefloxin, a combination thereof, or a pharmaceutically acceptable salt thereof.

In some embodiments the antibiotic is not a quinolone, fluoroquinolone, or a pharmaceutically acceptable salt thereof. In some embodiments the antibiotic is not ciprofloxacin or a pharmaceutically acceptable salt thereof.

In some embodiments the antibiotic is a cephalosporin or a pharmaceutically acceptable salt thereof. In some embodiments the antibiotic is ceftriaxone, cefoperazone, a combination thereof, or a pharmaceutically acceptable salt thereof.

In some embodiments the antibiotic is not a cephalosporin or a pharmaceutically acceptable salt thereof.

In some embodiments the antibiotic is a peptide, glycopeptide, or a pharmaceutically acceptable salt thereof. In some embodiments, the antibiotic is vancomycin, polymyxin B, a combination thereof, or a pharmaceutically acceptable salt thereof. In some embodiments, the antibiotic is a cathelicidin peptide.

In some embodiments the antibiotic is not a peptide, glycopeptide, or a pharmaceutically acceptable salt thereof. In some embodiments, the antibiotic is not a cathelicidin peptide.

In some embodiments, the antibiotic is chloramphenicol, dirithromycin, erythromycin, doxycycline, tetracycline, linezolid, bacitracin, fosfomycin, fosmidomycin, ampicillin, amoxicillin, cloxacillin, piperacillin, oxacillin, ceftriaxone, cefoperazone, vancomycin, polymyxin B, ciprofloxacin, besifloxacin, enoxacin, nalidixic acid, norfloxacin, levofloxacin, moxifloxacin, pefloxin, novobiocin, pentamidine, rifampicin, trimethoprim, sulfamethoxazole, a combination thereof, or a pharmaceutically acceptable salt thereof.

In some embodiments, the antibiotic is apramycin, neomycin, paromycin, spectinomycin, chloramphenicol, dirithromycin, erythromycin, doxycycline, tetracycline, linezolid, bacitracin, fosfomycin, fosmidomycin, ampicillin, amoxicillin, cloxacillin, a combination thereof, or a pharmaceutically acceptable salt thereof.

In some embodiments, the antibiotic is erythromycin, dirithromycin, levofloxacin, norfloxacin, ciprofloxacin, enoxacin, moxifloxacin, besifloxacin polymyxin B, a combination thereof, or a pharmaceutically acceptable salt thereof.

In some embodiments, the antibiotic is cefoperazone, novobiocin, ampicillin, cloxacillin, oxacillin, doxycycline or a pharmaceutically acceptable salt thereof.

In some embodiments, an antibiotic agent is Amikacin, Apramycin, Gentamicin, Kanamycin, Neomycin, Tobramycin, Paromomycin, Streptomycin, Spectinomycin, Ertapenem, Doripenem, Imipenem/Cilastatin, Meropenem, Cefadroxil, Cefazolin, Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Teicoplanin, Vancomycin, Telavancin, Clindamycin, Lincomycin, Lipopeptide, Daptomycin, Azithromycin, Clarithromycin, Dirithromycin, Erythromycin, Roxithromycin, Troleandomycin, Telithromycin, Spiramycin, Aztreonam, Linezolid, Posizolid, Radezolid, Torezolid, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Bacitracin, Colistin, Polymyxin B, Besifloxacin, Ciprofloxacin, Enoxacin, Gatifloxacin, Gemifloxacin, Levofloxacin, Lomefloxacin, Moxifloxacin, Nalidixic acid, Norfloxacin, Ofloxacin, Pefloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Sulfonamidochrysoidine, Demeclocycline, Doxycycline, Minocycline, Oxytetracycline, Tetracycline, Arsphenamine, Chloramphenicol, Fosfomycin, Fusidic acid, Metronidazole, Mupirocin, Platensimycin, Quinupristin/Dalfopristin, Thiamphenicol, Tigecycline, Tinidazole, Trimethoprim, Clofazimine, Dapsone, Capreomycin, Cycloserine, Ethambutol, Ethionamide, Isoniazid, Pyrazinamide, Rifampicin, Rifabutin, Rifapentine or Streptomycin, or a pharmaceutically acceptable salt thereof.

In some embodiments, the antibiotic agent causes a decrease in the pH gradient across the microorganism's cytoplasmic membrane.

In some embodiments, the antibiotic agent causes an increase in the microorganism's cytoplasmic membrane potential.

In some embodiments, the antibiotic agent is a cationic antibiotic agent, an antibiotic agent that is an energy dependent efflux substrate, an antibiotic agent for which entry depends on membrane potential, or an antibiotic agent that disrupts membrane potential as a primary mechanism of action.

Also provided herein are methods for treating a bacterial infection, or a disease, disorder or condition arising from a bacterial infection, comprising administering to a subject in need thereof an effective amount of (i) bicarbonate and (ii) an antibiotic.

Innate Immunity Factors

In some embodiments, the antimicrobial agent is an innate immunity factor.

Innate immunity factors are components of the innate immune system including several classes of soluble molecules present in blood, extracellular fluid and epithelial secretions that are intrinsically biologically active and affect pathogen survival. Examples include antimicrobial peptides such as defensins, antimicrobial enzymes, such as lysozyme and antimicrobial secretions, such as hyaluronic acid.

Accordingly, in some embodiments, an antimicrobial agent is an innate immunity factor such as an antimicrobial peptide, an antimicrobial enzyme, or an antimicrobial secretion. In some embodiments, the innate immunity factor is LL-37, indolicidin, bactenesin, defensin, alpha-defensin, a bile salt, lysozyme, protegrin, or hyaluronic acid, or a pharmaceutically acceptable salt thereof. In some embodiments, the innate immunity factor is a cathelicidin peptide. In some embodiments, the innate immunity factor is not a cathelicidin peptide. In some embodiments, the innate immunity factor is not LL-37.

Also provided herein are methods for treating a microbial infection, or a disease, disorder or condition arising from a microbial infection, comprising administering to a subject in need thereof an effective amount of (i) bicarbonate and (ii) an innate immunity factor.

Antiviral Agents

In some embodiments, the antimicrobial agent is an antiviral agent.

In some embodiments, an antiviral agent is Abacavir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nitazoxanide, Nucleoside analogues, Norvir, Oseltamivir, Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer (antiretroviral), Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir or Zidovudine, or a pharmaceutically acceptable salt thereof.

Also provided herein are methods for treating a viral infection, or a disease, disorder or condition arising from a viral infection, comprising administering to a subject in need thereof an effective amount of (i) bicarbonate and (ii) an antiviral agent.

Anti-Fungal Agents

In some embodiments, the antimicrobial agent is an anti-fungal agent.

In some embodiments, an anti-fungal agent is Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Efinaconazole, Epoxiconazole, Fluconazole, Isavuconazole, Itraconazole, Posaconazole, Propiconazole, Ravuconazole, Terconazole, Voriconazole, Abafungin, Amorolfin, Butenafine, Naftifine, and Terbinafine, Anidulafungin, Caspofungin, Micafungin, Aurones, Benzoic acid, Ciclopirox, Flucytosine, Griseofulvin, Haloprogin, Tolnaftate, Undecylenic acid, Crystal violet, Orotomide or Miltefosine, or a pharmaceutically acceptable salt thereof.

Also provided herein are methods for treating a fungal infection, or a disease, disorder or condition arising from a fungal infection, comprising administering to a subject in need thereof an effective amount of (i) bicarbonate and (ii) an anti-fungal agent.

Anti-Parasitic Agents

In some embodiments, the antimicrobial agent is an anti-parasitic agent.

In some embodiments, an anti-parasitic agent is Nitazoxanide, Melarsoprol, Eflornithine, Metronidazole, Tinidazole, Miltefosine, Ancylostoma caninum, Mebendazole, Pyrantel pamoate, Thiabendazole, Diethylcarbamazine, Ivermectin, Niclosamide, Praziquantel, Albendazole, Antitrematodes, Praziquantel, Rifampin, Amphotericin B or Fumagillin, or a pharmaceutically acceptable salt thereof.

Also provided herein are methods for treating a parasitic infection, or a disease, disorder or condition arising from a parasitic infection, comprising administering to a subject in need thereof an effective amount of (i) bicarbonate and (ii) an anti-parasitic agent.

Pentamidine and Analogs Thereof

In some embodiments, an antimicrobial agent is diamidine or a pharmaceutically acceptable salt thereof. In some embodiments, an antimicrobial agent is propamidine or a pharmaceutically acceptable salt thereof. In some embodiments, an antimicrobial agent is pentamidine or a pharmaceutically acceptable salt thereof. In some embodiments, an antimicrobial agent is not a diamidine, or a pharmaceutically acceptable salt thereof. In one embodiment, an antimicrobial agent is not pentamidine, or a pharmaceutically acceptable salt thereof.

Pentamidines include analogs thereof, including pharmaceutically acceptable salts and solvates thereof. Various analogs of pentamidine are known in the art. In some embodiments, the analogs of pentamidine can have an alkylene linker that ranges from 2 to 10 carbon atoms.

Pentamidine is provided in Formula I:

(Formula I)

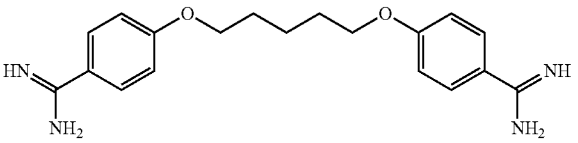

In some embodiments the analogs of pentamidine are compounds of Formula II or a pharmaceutically acceptable salt thereof.

(Formula II)

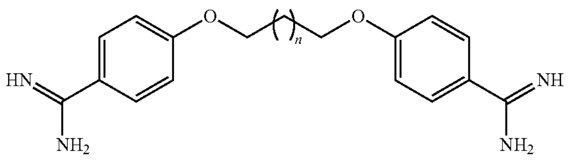

wherein n is 0, 1, 2, 3, 4, 5, 6, 7 or 8. In some embodiments, n is 1. In some embodiments, n is an integer from 2 to 4.

Microorganisms

The methods provided herein comprise contacting a microorganism with an antimicrobial agent in the presence of bicarbonate. In some embodiments, the presence of bicarbonate modulates the microorganism's growth in response to the antimicrobial agent.

In some embodiments, the presence of bicarbonate decreases the microorganism's growth in response to antimicrobial agent. In some embodiments, the presence of bicarbonate decreases the microorganism's growth in response to the antimicrobial agent by at least 10-fold. In some embodiments, the presence of bicarbonate decreases the microorganism's growth in response to the antimicrobial agent by at least 20-fold. In some embodiments, the presence of bicarbonate decreases the microorganism's growth in response to the antimicrobial agent by at least 30-fold.

In some embodiments, the presence of bicarbonate increases the microorganism's growth response to the antimicrobial agent. In some embodiments, the presence of bicarbonate increases the microorganism's growth in response to the antimicrobial agent by at least 10-fold.

In some embodiments, a method described herein inhibits the growth of a microorganism.

In some embodiments of the methods described herein, a microorganism is present on a substrate. In some examples, a substrate is glass, metal, plastic, latex, ceramic, cement, wood, grout or stone.

In some embodiments, a subject is infected with the microorganism. In some embodiments, the subject is a mammal. In some embodiments, the subject is a human. In some embodiments, the subject has a microbial infection. In some embodiments, the microbial infection is a pulmonary, lung, otic, oral, nasal, sinus, ophthalmic, intraocular, dermal, cardiovascular, kidney, urinary, gastrointestinal, rectal, vaginal or neurological infection.

In some embodiments of the methods described herein, a microorganism is a bacterium. In some embodiments, a bacterium is a Gram negative bacterium. In some embodiments, a bacterium is a Gram positive bacterium. In some embodiments, a bacterium is a spiral-shaped bacterium, a filamentous bacterium, a pleomorphic bacterium or a rectangular bacterium. In other embodiments, a bacterium is a sphere-shaped bacterium, a rod-shaped bacterium, a spiral-shaped bacterium, a filamentous bacterium, a pleomorphic bacterium or a rectangular bacterium. In one embodiment, a bacterium is a Gram positive rod-shaped bacterium. In another embodiment, a bacterium is a Gram negative rod-shaped bacterium. In yet another embodiment, a bacterium is a Gram positive sphere-shaped bacterium. In a further embodiment, a bacterium is a Gram negative sphere-shaped bacterium.

In some aspects of the methods described herein, a bacterium is an obligate aerobe or an obligate anaerobe. In other aspects of the methods described herein, a bacterium is a facultative anaerobe.

In some embodiments of the methods described herein, a bacterium is a species of *Acinetobacter, Actinomyces, Aerococcus, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Lactococcus, Legionella, Listeria, Methanobacterium, Microbacterium, Micrococcus, Moraxella, Mycobacterium, Mycoplasma, Neisseria, Pasteurella, Pediococcus, Peptostreptococcus, Porphyromonas, Prevotella, Pseudomonas, Rhizobium, Rickettsia, Rochalimaea, Rothia, Salmonella, Serratia, Shigella, Sarcina, Spirillum, Spirochaetes, Staphylococcus, Stenotrophomonas, Streptobacillus, Streptococcus, Tetragenococcus, Treponema, Vibrio, Viridans, Wolbachia* or *Yersinia*.

In some embodiments of the methods described herein, a bacterium is *Acetobacter aurantius, Acinetobacter baumannii, Actinomyces israelii, Agrobacterium radiobacter, Agrobacterium tumefaciens, Anaplasma phagocytophilum, Azorhizobium caulinodans, Azotobacter vinelandii, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacillus Thuringiensis, Bacteroides fragilis, Bacteroides gingivalis, Bacteroides melaninogenicus, Bartonella henselae, Bartonella Quintana, Bordetella bronchiseptica, Bordetella pertussis, Borrelia burgdorferi. Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae, Chlamydophila psittaci, Clostridium botulinum, Clostridium difficile, Clostridium perfringens, Clostridium tetani, Corynebacterium diphtheriae, Corynebacterium fusiforme, Coxiella burnetii, Ehrlichia chaffeensis, Enterobacter cloacae, Enterococcus avium, Enterococcus durans, Enterococcus faecalis, Enterococcus faecium, Enterococcus gallinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Peptostreptococcus, Porphyromonas gingivalis, Prevotella melaninogenica, Pseudomonas aeruginosa, Rhizobium radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Spirillum volutans, Staphylococcus aureus, Staphylococcus epidermidis, Stenotrophomonas maltophilia, Streptococcus agalactiae, Streptococcus avium, Streptococcus bovis, Streptococcus cricetus, Streptococcus faceium, Streptococcus faecalis, Streptococcus ferns, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Viridans streptococci, Wolbachia, Yersinia enterocolitica, Yersinia pestis* or *Yersinia pseudotuberculosis.*

In some embodiments of the methods described herein, the bacterium is *Escherichia coli, Acinetobacter baumannii, Klebsiella pneumoniae, Pseudomonas aeruginosa, Burkhloderia cenocepacia, Burkhloderia multivorans, Enterococcus faecalis* or *Staphylococcus aureus*. In some embodiments, the bacterium is *Escherichia coli*. In some embodiments, the bacterium is *Staphylococcus aureus*. In some embodiments of the methods described herein, the bacterium is methicillin-resistant *Staphylococcus aureus* (MRSA) or methicillin-sensitive *Staphylococcus aureus* (MSSA).

In some embodiments of the methods described herein, the bacterium is not *Escherichia coli, Acinetobacter baumannii, Klebsiella pneumoniae, Pseudomonas aeruginosa, Burkhloderia cenocepacia, Burkhloderia multivorans, Enterococcus faecalis* or *Staphylococcus aureus*. In some embodiments, the bacterium is not *Escherichia coli*. In some embodiments, the bacterium is not *Staphylococcus aureus*. In some embodiments of the methods described herein, the bacterium is not methicillin-resistant *Staphylococcus aureus* (MRSA) or methicillin-sensitive *Staphylococcus aureus* (MSSA).

In some embodiments, a bacterial infection is an infection by *Escherichia coli, Acinetobacter baumannii, Klebsiella pneumoniae, Pseudomonas aeruginosa, Burkhloderia ceno-*

*cepacia, Burkhloderia multivorans, Enterococcus faecalis* or *Staphylococcus aureus* (e.g., MRSA or MSSA).

In some embodiments, the microbial infection treated by the methods and compositions described herein is a bacterial infection and the antimicrobial agent is an antibiotic. In some embodiments, the antimicrobial agent is an antibiotic, anti-fungal agent, or innate immunity factor. In some embodiments, the antibiotic is a macrolide, tetracycline, peptide, glycopeptide, penicillin, cephalosporin, quinolone, or fluoroquinolone. In some embodiments, the antibiotic is pentamidine, erythromycin, dirithromycin, levofloxacin, norfloxacin, ciprofloxacin, enoxacin, moxifloxacin, besifloxacin or polymyxin B, or a pharmaceutically acceptable salt thereof.

In some embodiments of the methods described herein, a microorganism is a virus. In some examples, a virus is an Adenoviridae, Herpesviridae, Poxviridae, Papillomaviridae, Polyomaviridae, Parvoviridae, Reoviridae, Astroviridae, Caliciviridae, Picornaviridae, Coronaviridae, Hepeviridae, Flaviviridae, Togaviridae, Arenaviridae, Bunyaviridae, Filoviridae, Paramyxoviridae, Rhabdoviridae, Orthomyxoviridae, Retroviridae or Hepadnaviridae family member. In some embodiments, a virus is Adenovirus, Herpes simplex virus type 1, Herpes simplex virus type 2, Varicella-zoster virus, Epstein-Barr virus, Human cytomegalovirus, Human herpesvirus type 8, Smallpox, Human papillomavirus, BK virus, JC virus, Parvovirus B19, Rotavirus, Orbivirus, Coltivirus, Banna virus, Human astrovirus, Norwalk virus, coxsackievirus, Hepatitis A virus, Hepatitis B virus, Hepatitis C virus, Hepatitis D virus, Hepatitis E virus, poliovirus, rhinovirus, Severe acute respiratory syndrome virus, yellow fever virus, dengue virus, West Nile virus, TBE virus, Rubella virus, Lassa virus, Crimean-Congo hemorrhagic fever virus, Hantaan virus, Ebola virus, Marburg virus, Measles virus, Mumps virus, Parainfluenza virus, Respiratory syncytial virus, Rabies virus, Influenza virus or Human immunodeficiency virus (HIV).

In some embodiments, the microbial infection treated by the methods and compositions described herein is a viral infection and the antimicrobial agent is an antiviral agent.

In some embodiments of the methods provided herein, a microorganism is a fungus. In some embodiments, a fungus is a yeast. In an illustrative embodiment, the fungus is *Pneumocystis carinii*. In some aspects, methods are provided to treat or prevent *Pneumocystis carinii* pneumonia, comprising administering to a subject in need thereof an effective amount of (i) bicarbonate and (ii) an antimicrobial agent. In some embodiments, the microbial infection treated by the methods and compositions described herein is a fungal or yeast infection and the antimicrobial agent is an anti-fungal agent. In some embodiments, the fungal infection is a *Pneumocystis carinii* infection and the disease, disorder or condition arising from the fungal infection is *Pneumocystis carinii* pneumonia.

In some embodiments of the methods disclosed herein, a fungus is an *Agaricus* species, *Amanita* species, *Armillaria* species, *Aspergillus* species, *Boletus* species, *Caloplaca* species, *Candida* species, *Cladonia* species, *Coprinellus* species, *Coprinopsis* species, *Cortinarius* species, *Cyathus* species, Deadly fungus species, *Entoloma* species, *Fusarium* species, *Gymnopilus* species, *Gymnopus* species, *Hebeloma* species, *Hygrocybe* species, *Hygrophorus* species, *Inocybe* species, *Lactarius* species, *Lactifluus* species, *Lecanora* species, *Lepiota* species, *Leucoagaricus* species, *Lichen* species of Montana, *Leccinum* species, *Marasmius* species, *Pleurotus* species, *Mycosphaerella* species, *Panaeolus* species, *Penicillium* species, *Peniophora* species, *Pertusaria* species, *Phaeocollybia* species, *Pholiota* species, *Pholiotina* species, *Pluteus* species, Poisonous fungus species, *Psathyrella* species, *Psilocybe* species, Psilocybin mushroom species, *Puccinia* species, *Russula* species, *Scleroderma* species, *Serpula* species, *Trametes* species, *Tricholoma* species, *Tuber* species, or *Tulostoma* species.

In some embodiments of the methods disclosed herein, a microorganism is a parasite. In some embodiments, a parasite is a protozoan.

In some embodiments of the methods provided herein, a parasite is an *Acanthamoeba* species, *Balamuthia mandrillaris, B. divergens, B. bigemina, B. equi, B. microfti, B. duncani, Balantidium coli*, a *Blastocystis* species, a *Cryptosporidium* species, *Cyclospora cayetanensis, Dientamoeba fragilis, Entamoeba histolytica, Giardia lamblia, Isospora belli*, a *Leishmania* species, *Naegleria fowleri, Plasmodium falciparum, Plasmodium vivax, Plasmodium ovale curtisi, Plasmodium ovale wallikeri, Plasmodium malariae, Plasmodium knowlesi, Rhinosporidium seeberi, Sarcocystis bovihominis, Sarcocystis suihominis, Toxoplasma gondii, Trichomonas vaginalis, Trypanosoma brucei, Trypanosoma cruzi, Cestoda, Taenia multiceps, Diphyllobothrium latum, Echinococcus granulosus, Echinococcus multilocularis, E. vogeli, E. oligarthrus, Hymenolepis nana, Hymenolepis diminuta, Taenia saginata, Taenia solium, Bertiella mucronata, Bertiella studeri, Spirometra erinaceieuropaei, Echinostoma echinatum, Schistosoma mekongi, Opisthorchis viverrini, Opisthorchis felineus, Clonorchis sinensis, Clonorchis sinensis; Clonorchis viverrini, Fasciolopsis buski, Schistosoma mansoni, Schistosoma intercalatum, Dicrocoelium dendriticum, Fasciola hepatica, Fasciola gigantica, Metagonimus yokogawai, Metorchis conjunctus, Paragonimus westermani, Paragonimus africanus, Paragonimus caliensis, Paragonimus kellicotti, Paragonimus skrjabini, Paragonimus uterobilateralis, Schistosoma japonicum, a Schistosoma species, Trichobilharzia regenti, Schistosomatidae, Schistosoma haematobium, Ancylostoma duodenale, Necator americanus, Angiostrongylus costaricensis*, an Anisakis *Ascaris* species, *Ascaris lumbricoides, Baylisascaris procyonis, Brugia malayi, Brugia timori, Dioctophyme renale, Dracunculus medinensis, Enterobius vermicularis, Enterobius gregorii, Gnathostoma spinigerum, Gnathostoma hispidum, Halicephalobus gingivali, Loa loa filarial, Mansonella streptocerca, Onchocerca volvulus, Strongyloides stercoralis, Thelazia californiensis, Thelazia callipaeda, Toxocara canis, Toxocara cati, Trichinella spiralis, Trichinella britovi, Trichinella nelsoni, Trichinella native, Trichuris trichiura, Trichuris vulpis, Wuchereria bancrofti, Archiacanthocephala, Moniliformis moniliformis, Linguatula serrate, Oestroidea, Calliphoridae, Sarcophagidae, Cochliomyia hominivorax, Tunga penetrans, Dermatobia hominis, Pediculus humanus capitis, Pediculus humanus humanus, Pthirus pubis, Demodex folliculorum/brevis/canis, Sarcoptes scabiei*, an Arachnida class member, Trombiculidae, Pulex irritans, Cimicidae, Cimex lectularius, an Ixodidae family member or an Argasidae family member.

In another aspect, provided herein are methods of treating a microbial infection, or a disease, disorder or condition arising from a microbial infection, comprising administering, to a subject in need thereof, an effective amount of (i) bicarbonate and (ii) an antimicrobial agent, wherein the antimicrobial agent is an antimicrobial agent whose concentration in a cell of the microorganism is increased by one or both of (1) decrease in pH gradient across the microorganism's cytoplasmic membrane; and (2) increase in the microorganism's cytoplasmic membrane potential and wherein the antimicrobial agent is not an aminoglycoside.

In another aspect, provided herein are methods of treating a microbial infection, or a disease, disorder or condition arising from a microbial infection, comprising administering to a subject in need thereof an effective amount of (i) bicarbonate and (ii) an antimicrobial agent, wherein the microbial infection is caused by a microorganism, and wherein the antimicrobial agent is a cationic antimicrobial agent, antimicrobial agent that is an energy dependent efflux substrate, antimicrobial agent for which entry depends on membrane potential, or an antimicrobial agent that disrupts membrane potential as a primary mechanism of action.

Bicarbonate

Bicarbonate forms the dominant buffering system in the human body, which plays an important role in maintaining the pH of blood around 7.4.

The methods provided herein comprise contacting a microorganism with an antimicrobial agent in the presence of bicarbonate.

In some embodiments, the bicarbonate potentiates antimicrobial activity by increasing the effective intracellular levels of various antimicrobial agents or enhancing their ability to collapse PMF.

In some embodiments, the bicarbonate is potassium, lithium, calcium, magnesium, sodium, ammonium or zinc bicarbonate. In some embodiments, the bicarbonate is sodium bicarbonate or ammonium bicarbonate. In some embodiments, the bicarbonate is sodium bicarbonate.

In some embodiments, the dosage or amount of the bicarbonate is an amount that provides a physiological concentration of bicarbonate. In some embodiments, the dosage or amount of the bicarbonate is about 25 mM of bicarbonate. In some embodiments, the bicarbonate is present in a composition. In some embodiments, the composition is an aqueous composition. In some embodiments, the composition comprises bicarbonate at a concentration of about 1 mM to about 900 mM. In some embodiments, the composition comprises bicarbonate at a concentration of about 1 mM to about 150 mM bicarbonate, about 25 mM to about 100 mM bicarbonate, about 30 mM to about 100 mM bicarbonate, or about 20 mM to about 50 mM bicarbonate. In some embodiments, the composition comprises bicarbonate at a concentration of about 1 mM, about 5 mM, about 10 mM, about 15 mM, about 20 mM, about 25 mM, about 30 mM, about 35 mM, about 40 mM, about mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM or about 150 mM. In some embodiments, the composition comprises bicarbonate at a concentration of greater than 150 mM, such as about 175 mM to about 900 mM. In some embodiments, the composition comprises bicarbonate at a concentration of about 175 mM to about 225 mM, about 200 mM to about 300 mM, about 300 mM to about 400 mM, about 400 mM to about 500 mM, about 500 mM to about 600 mM, about 600 mM to about 700 mM, about 700 mM to about 800 mM or about 800 mM to about 900 mM. Where the composition comprises bicarbonate at a particular M or mM concentration, the M or mM concentration is moles or milimoles, respectively, of bicarbonate per liter of water. In some embodiments, the composition comprises bicarbonate in an amount of about 0.01 wt % to about 8.4 wt % of the composition. In some embodiments, the composition comprises bicarbonate in an amount of about 0.01 wt % to about 1.0 wt %, or about 0.20 wt % to about 0.5 wt % of the composition. In some embodiments, the composition comprises bicarbonate in a composition in an amount of about 1.75 wt % to about 8.4 wt % of the composition.

In some embodiments, bicarbonate useful in the methods and compositions described herein is a component of a buffer. As with any buffer system, bicarbonate acts as a buffer in solution at neutral pH due to the presence of both a weak acid (carbonic acid; $H_2CO_3$) and its conjugate base ($HCO_3^-$) where these species have the capacity to buffer the added base or acid, respectively. As shown below, in a bicarbonate buffer system, dissolved carbon dioxide and bicarbonate ion are at equilibrium.

$$CO_2 + H_2O \rightleftharpoons H_2CO_3 \rightleftharpoons HCO_3^- + H^+$$

The pKa of carbonate is 6.1 and thus at neutral pH typically used in microbiological testing or that of the human body (e.g., pH 7.4), the vast majority of the carbonate-bicarbonate buffer system is present as the conjugate base bicarbonate ion. Thus, the active species is likely the bicarbonate ion, consistent with its ability to buffer protons that figure in the proton gradient of the proton motive force. Although carbonate is present in this system, the system may be described as a bicarbonate buffer because bicarbonate is the dominant species.

Methods of Use

The invention provides methods for inhibiting the growth of a microorganism, comprising contacting the microorganism with an effective amount of (i) bicarbonate and (ii) an antimicrobial agent. In some examples, an antimicrobial agent is pentamidine, an antibiotic agent, an innate immunity factor, an antiviral agent, an anti-fungal agent or an anti-parasitic agent.

In some embodiments, invention provides methods for inhibiting the growth of a virus, a bacterium, a fungus or a parasite, comprising contacting the virus, the bacterium, the fungus or the parasite with an effective amount of (i) bicarbonate and (ii) an antimicrobial agent;

wherein the bacterium is:

(a) a spiral-shaped bacterium, a filamentous bacterium, a pleomorphic bacterium or a rectangular bacterium;

(b) an obligate aerobe or an obligate anaerobe;

(c) a Gram positive rod-shaped bacterium;

(d) a Gram negative sphere-shaped bacterium;

(e) a species of *Acinetobacter, Actinomyces, Aerococcus, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Clostridium, Corynebacterium, Coxiella, Ehrlichia, Enterobacter, Enterococcus, Francisella, Fusobacterium, Gardnerella, Haemophilus, Helicobacter, Klebsiella, Lactobacillus, Lactococcus, Legionella, Listeria, Methanobacterium, Microbacterium, Micrococcus, Moraxella, Mycobacterium, Mycoplasma, Neisseria, Pasteurella, Pediococcus, Peptostreptococcus, Porphyromonas, Prevotella, Pseudomonas, Rhizobium, Rickettsia, Rochalimaea, Rothia, Salmonella, Serratia, Shigella, Sarcina, Spirillum, Spirochaetes, Stenotrophomonas, Streptobacillus, Streptococcus, Tetragenococcus, Treponema, Vibrio, Viridans, Wolbachia* or *Yersinia*; or f) *Staphylococcus epidermidis.*

Provided herein are methods for inhibiting the growth of *Staphylococcus aureus*, comprising contacting the *Staphylococcus aureus* with an effective amount of (i) bicarbonate and (ii) pentamidine or a pharmaceutically acceptable salt thereof.

Additionally provided herein are methods for treating or preventing a microbial infection, comprising administering to a subject in need thereof an effective amount of (i) bicarbonate and (ii) an antimicrobial agent;

wherein the microbial infection is an infection by a virus, a bacterium, a fungus or a parasite; and wherein the bacterium is:

(a) a spiral-shaped bacterium, a filamentous bacterium, a pleomorphic bacterium or a rectangular bacterium;

(b) an obligate aerobe or an obligate anaerobe;

(c) a Gram positive rod-shaped bacterium;

(d) a Gram negative sphere-shaped bacterium;

(e) a species of *Acinetobacter, Actinomyces, Aerococcus, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Clostridium, Corynebacterium, Coxiella, Ehrlichia, Enterobacter, Enterococcus, Francisella, Fusobacterium, Gardnerella, Haemophilus, Helicobacter, Klebsiella, Lactobacillus, Lactococcus, Legionella, Listeria, Methanobacterium, Microbacterium, Micrococcus, Moraxella, Mycobacterium, Mycoplasma, Neisseria, Pasteurella, Pediococcus, Peptostreptococcus, Porphyromonas, Prevotella, Pseudomonas, Rhizobium, Rickettsia, Rochalimaea, Rothia, Salmonella, Serratia, Shigella, Sarcina, Spirillum, Spirochaetes, Stenotrophomonas, Streptobacillus, Streptococcus, Tetragenococcus, Treponema, Vibrio, Viridans, Wolbachia* or *Yersinia*; or (f) *Staphylococcus epidermidis.*

In some embodiments, disclosed herein is a method for inhibiting the growth of a virus, a bacterium, a fungus or a parasite, comprising contacting the virus, the bacterium, the fungus or the parasite with an effective amount of (i) bicarbonate and (ii) an antimicrobial agent;

wherein the antimicrobial agent is an antiviral agent, an anti-fungal agent, an anti-parasitic agent, an antibiotic agent, or an innate immunity factor; and wherein the antibiotic agent is (a) a macrolide, a tetracycline, a cephalosporin, a quinolone, a rifampin or a fluoroquinolone; or (b) Amoxicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin or Ticarcillin, or a pharmaceutically acceptable salt thereof.

In other embodiments, disclosed herein is a method of treating or preventing a microbial infection, comprising administering to a subject in need thereof an effective amount of (i) bicarbonate and (ii) an antimicrobial agent;

wherein the microbial infection is an infection by a virus, a bacterium, a fungus or a parasite;

wherein the antimicrobial agent is an antiviral agent, an anti-fungal agent, an anti-parasitic agent, an antibiotic agent, or an innate immunity factor; and wherein the antibiotic agent is (a) a macrolide, a tetracycline, a cephalosporin, a quinolone, a rifampin or a fluoroquinolone; or (b) Amoxicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin or Ticarcillin, or a pharmaceutically acceptable salt thereof.

In other embodiments, disclosed herein is a method of treating or preventing a microbial infection, comprising administering to a subject in need thereof an effective amount of (i) bicarbonate and (ii) an antimicrobial agent;

wherein the microbial infection is an infection by a bacterium, and wherein the bacterium is *Acetobacter aurantius, Acinetobacter baumannii, Actinomyces israelii, Agrobacterium radiobacter, Agrobacterium tumefaciens, Anaplasma phagocytophilum, Azorhizobium caulinodans, Azotobacter vinelandii, Bacillus anthracia, Bacillus brevis, Bacillus cereus, Bacillus fusiformis, Bacillus licheniformis, Bacillus megaterium, Bacillus mycoides, Bacillus stearothermophilus, Bacillus subtilis, Bacillus Thuringiensis, Bacteroides fragilis, Bacteroides gingivalis, Bacteroides melaninogenicus, Bartonella henselae, Bartonella Quintana, Bordetella bronchiseptica, Bordetella pertussis, Borrelia burgdorferi. Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae, Chlamydophila psittaci, Clostridium botulinum, Clostridium difficile, Clostridium perfringens, Clostridium tetani, Corynebacterium diphtheriae, Corynebacterium fusiforme, Coxiella burnetii, Ehrlichia chaffeensis, Enterobacter cloacae, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Peptostreptococcus, Porphyromonas gingivalis, Prevotella melaninogenica, Pseudomonas aeruginosa, Rhizobium radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Spirillum volutans, Staphylococcus aureus, Staphylococcus epidermidis, Stenotrophomonas maltophilia, Streptococcus agalactiae, Streptococcus avium, Streptococcus bovis, Streptococcus cricetus, Streptococcus faceium, Streptococcus faecalis, Streptococcus ferns, Streptococcus gallinarum, Streptococcus lactis, Streptococcus mitior, Streptococcus mitis, Streptococcus mutans, Streptococcus oralis, Streptococcus pneumoniae, Streptococcus*

*pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Viridans streptococci, Wolbachia, Yersinia enterocolitica, Yersinia pestis* or *Yersinia pseudotuberculosis.*

Provided herein are methods of modulating a microorganism's response to an antimicrobial agent. The methods comprise contacting a microorganism with an antimicrobial agent in the presence of bicarbonate, whereby the bicarbonate modulates the microorganism's response to the antimicrobial agent. In some embodiments, the bicarbonate potentiates the microorganism's response to the antimicrobial agent, resulting in an increased response. In some embodiments, the bicarbonate lessens the microorganism's response to the antimicrobial agent, resulting in a decreased response. In some embodiments, the antimicrobial agent is an innate immunity factor or a macrolide, tetracycline, peptide, glycopeptide, penicillin, cephalosporin, quinolone, rifampin, fluoroquinolone, an antifungal agent or aminoglycoside antibiotic. In some embodiments, the antimicrobial agent is not an aminoglycoside.

In some embodiments, the presence of bicarbonate decreases the microorganism's growth in response to the antimicrobial agent. In some embodiments, the presence of bicarbonate decreases the microorganism's growth in response to the antimicrobial agent by at least 2-fold, 4-fold, 5-fold, 8-fold, 10-fold, 15-fold, 20-fold, or 30-fold.

In some embodiments, the presence of bicarbonate increases the microorganism's growth response to the antimicrobial agent. In some embodiments, the presence of bicarbonate increases the microorganism's growth in response to the antimicrobial agent by at least 2-fold, 4-fold, 5-fold, 8-fold, 10-fold, 15-fold, 20-fold, or 30-fold.

In some embodiments, the presence of bicarbonate changes the MIC of the antimicrobial agent by at least 2-fold, 4-fold, 5-fold, 8-fold, 10-fold, 15-fold, 20-fold, or 30-fold.

Also provided herein are methods for treating a microbial infection, or a disease, disorder or condition arising from a microbial infection. The methods comprise administering to a subject in need thereof an effective amount of (i) bicarbonate and (ii) an antimicrobial agent, wherein the antimicrobial agent targets the membrane potential of a cell and/or is subject to an increase in intracellular concentration by one or both of (1) decrease in pH gradient across the microorganism's cytoplasmic membrane; and (2) increase in the microorganism's cytoplasmic membrane potential. In some embodiments, the antimicrobial agent is a macrolide, tetracycline, peptide, glycopeptide, penicillin, cephalosporin, quinolone, fluoroquinolone, rifampin, innate immunity factor, or combinations thereof. In some embodiments, the antimicrobial agent is not an aminoglycoside.

In one embodiment, disclosed herein is a method of treating or preventing an *Staphylococcus aureus* infection, comprising administering to a subject in need thereof an effective amount of (i) bicarbonate and (ii) pentamidine or a pharmaceutically acceptable salt thereof.

In some embodiments, the methods described herein comprise administering to a subject in need thereof an effective amount of (i) bicarbonate and (ii) indolicidin, bactenesin, defensin, alpha-defensin, a bile salt, lysozyme, protegrin, or hyaluronic acid.

The present invention provides methods for potentiating an antimicrobial agent comprising administering to a subject in need thereof an effective amount of (i) bicarbonate and (ii) the antimicrobial agent, wherein the antimicrobial agent is an antimicrobial agent whose concentration in a cell of the microorganism is increased by one or both of (1) decrease in pH gradient across the microorganism's cytoplasmic membrane; and (2) increase in the microorganism's cytoplasmic membrane potential. In some embodiments, the antimicrobial agent is a macrolide, tetracycline, peptide, glycopeptide, penicillin, cephalosporin, quinolone, fluoroquinolone, rifampin, innate immunity factor, or combinations thereof. In some embodiments, the antimicrobial agent is not an aminoglycoside.

Also provided herein is a use of bicarbonate and an antimicrobial agent to treat a microbial infection, or a disease, disorder or condition arising from a microbial infection. In one embodiment, the invention provides a use of bicarbonate and an antimicrobial agent for the preparation of a medicament to treat a microbial infection, or a disease, disorder or condition arising from a microbial infection, wherein the antimicrobial agent is an antimicrobial agent whose concentration in a cell of the microorganism is increased by one or both of (1) decrease in pH gradient across the microorganism's cytoplasmic membrane; and (2) increase in the microorganism's cytoplasmic membrane potential. In some embodiments, the antimicrobial agent is an aminoglycoside, macrolide, tetracycline, peptide, glycopeptide, penicillin, cephalosporin, quinolone, fluoroquinolone, rifampin, innate immunity factor, or combinations thereof. In some embodiments, the antimicrobial agent is not an aminoglycoside.

In some embodiments, the methods described herein may spare the natural or beneficial microbiota of a host.

In one embodiment, the invention provides bicarbonate and an antimicrobial agent for use in therapy. In another embodiment, the invention provides bicarbonate and an antimicrobial agent for use in a method of treating a microbial infection, or a disease, disorder or condition arising from a microbial infection.

Also included is bicarbonate for use with an antimicrobial agent to treat a microbial infection, or a disease, disorder or condition arising from a microbial infection. Further provided is bicarbonate for use with an antimicrobial agent to treat a microbial infection, or a disease, disorder or condition arising from a microbial infection, wherein the antimicrobial agent's concentration in a cell of the microorganism is increased by one or both of (1) decrease in pH gradient across the microorganism's cytoplasmic membrane; and (2) increase in the microorganism's cytoplasmic membrane potential. In some embodiments, the antimicrobial agent is a macrolide, tetracycline, peptide, glycopeptide, penicillin, cephalosporin, quinolone, fluoroquinolone, rifampin, innate immunity factor, or combinations thereof. In some embodiments, the antimicrobial agent is not an aminoglycoside.

Provided herein are methods of treating a topical microbial infection, or a disease, disorder or condition arising from a topical microbial infection, comprising administering to a subject in need thereof an effective amount of (i) bicarbonate and (ii) the antimicrobial agent, wherein the antimicrobial agent's concentration in a cell of the microorganism is increased by one or both of (1) decrease in pH gradient across the microorganism's cytoplasmic membrane; and (2) increase in the microorganism's cytoplasmic membrane potential. In some embodiments, the antimicrobial agent is a macrolide, tetracycline, peptide, glycopeptide, penicillin, cephalosporin, quinolone, fluoroquinolone, rifampin, innate immunity factor, or combinations thereof. In some embodiments, the antimicrobial agent is not an aminoglycoside.

Also provided herein is a use of bicarbonate and an antimicrobial agent to treat a topical microbial infection, or a disease, disorder or condition arising from a topical microbial infection, and a use of bicarbonate and an antimicrobial agent to prepare a medicament to treat a topical microbial infection, or a disease, disorder or condition arising from a microbial infection, wherein the antimicrobial agent's concentration in a cell of the microorganism is increased by one or both of (1) decrease in pH gradient across the microorganism's cytoplasmic membrane; and (2) increase in the microorganism's cytoplasmic membrane potential. Also included is bicarbonate for use and an antimicrobial agent to treat a topical microbial infection, or a disease, disorder or condition arising from a microbial infection, wherein the antimicrobial agent's concentration in a cell of the microorganism is increased by one or both of (1) decrease in pH gradient across the microorganism's cytoplasmic membrane; and (2) increase in the microorganism's cytoplasmic membrane potential. In some embodiments, the antimicrobial agent is a macrolide, tetracycline, peptide, glycopeptide, penicillin, cephalosporin, quinolone, fluoroquinolone, rifampin, innate immunity factor, or combinations thereof. In some embodiments, the antimicrobial agent is not an aminoglycoside.

Compositions, Pharmaceutical Uses and Routes of Administration

In some embodiments, provided herein is a composition comprising: an effective amount of (i) bicarbonate and (ii) an antimicrobial agent. In some aspects, a composition described herein further comprises a pharmaceutically acceptable carrier, diluent or excipient.

In some embodiments, a composition disclosed herein comprises:

an effective amount of (i) bicarbonate and (ii) an antimicrobial agent;

wherein the antimicrobial agent is an antiviral agent, an antibiotic agent, an anti-fungal agent, an anti-parasitic agent or an innate immunity factor; and wherein the antibiotic agent is a macrolide, a tetracycline, a cephalosporin, a quinolone, a rifampin or a fluoroquinolone.

In some embodiments, a composition disclosed herein comprises:

an effective amount of (i) bicarbonate and (ii) an antimicrobial agent;

wherein the antimicrobial agent is an antiviral agent, an antibiotic agent, an anti-fungal agent, an anti-parasitic agent or an innate immunity factor; and wherein the antibiotic agent is Amikacin, Neomycin, Tobramycin, Paromomycin, Streptomycin, Spectinomycin, Ertapenem, Doripenem, Imipenem/Cilastatin, Meropenem, Cefadroxil, Cefazolin, Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Teicoplanin, Vancomycin, Telavancin, Clindamycin, Lincomycin, Lipopeptide, Daptomycin, Azithromycin, Clarithromycin, Dirithromycin, Erythromycin, Roxithromycin, Troleandomycin, Telithromycin, Spiramycin, Aztreonam, Linezolid, Posizolid, Radezolid, Torezolid, Amoxicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Bacitracin, Colistin, Polymyxin B, Besifloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Sulfonamidochrysoidine, Demeclocycline, Doxycycline, Minocycline, Oxytetracycline, Tetracycline, Arsphenamine, Chloramphenicol, Fosfomycin, Fusidic acid, Metronidazole, Mupirocin, Platensimycin, Quinupristin/Dalfopristin, Thiamphenicol, Tigecycline, Tinidazole, Trimethoprim, Clofazimine, Dapsone, Capreomycin, Cycloserine, Ethambutol, Ethionamide, Isoniazid, Pyrazinamide, Rifampicin, Rifabutin, Rifapentine or Streptomycin, or a pharmaceutically acceptable salt thereof.

In some embodiments, the antimicrobial agent in a composition described herein is erythromycin, dirithromycin, levofloxacin, norfloxacin, ciprofloxacin, enoxacin, moxifloxacin, besifloxacin or polymyxin B, or a pharmaceutical salt thereof.

In some embodiments, the composition comprises sodium bicarbonate and indolicidin, bactenesin, alpha-defensin, bile salts, lysozyme, protegrin, or hyaluronic acid.

In some embodiments, the composition comprises about 1 mM to about 150 mM bicarbonate.

In some embodiments, the antimicrobial agent is pentamidine, or a pharmaceutically acceptable salt or analog thereof. In one embodiment, a composition comprises an effective amount of (i) bicarbonate and (ii) pentamidine or a pharmaceutically acceptable salt thereof. In some embodiments, the composition comprises about 0.1 wt % to about 1.0 wt % pentamidine and about 0.01 wt % to about 1.0 wt % bicarbonate.

In some embodiments, the composition is suitable for administration intraocularly. In some embodiments, the composition is useful as an ophthalmic topical solution or gel, or is for topical, subconjunctival, periocular, retrobulbar, sub-tenon, intracameral, intravitreal, intraocular, subretinal, juxtascleral or suprachoroidal administration.

The bicarbonate and an antimicrobial agent can be administered to a subject, or used, in a variety of forms depending on the selected route of administration, as will be understood by those skilled in the art.

In some embodiments, the bicarbonate and/or an antimicrobial agent can be administered to the subject, or used, by oral (including sublingual and buccal) or parenteral (including, intravenous, intraperitoneal, subcutaneous, intramuscular, transepithelial, nasal, intrapulmonary, intrathecal, rectal, topical, patch, pump, intraocular and transdermal) administration and the compound(s) formulated accordingly. In some embodiments, both the bicarbonate and the antimicrobial agent are administered orally. In some embodiments, both the bicarbonate and the antimicrobial agent are administered parenterally. In some embodiments, the bicarbonate and the antimicrobial agent are administrated via different modes of administration. In some embodiments, the bicarbonate is administered parenterally and the antimicrobial agent is administered orally. In some embodiments, the bicarbonate is administered orally and the antimicrobial agent is administered parenterally.

In one embodiment, the bicarbonate and an antimicrobial agent are administered to the subject orally. In another embodiment, the bicarbonate and an antimicrobial agent are administered to the subject intravenously.

Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999. In general, the bicarbonate and an antimicrobial agent can be used in the forms in which they are available and administered to subjects. Such forms, include, for example in the form of their pharmaceutically acceptable salts, in the form of fine particles of the zwitterionic form and in an injectable or infusable suspensions.

In some embodiments, the bicarbonate and/or the antimicrobial agent is administered to a subject as an ophthalmic topical solution or gel, or by topical, dermal, transdermal, subconjunctival, periocular, retrobulbar, sub-tenon, intracameral, intravitreal, intraocular, subretinal, juxtascleral or suprachoroidal administration.

The pharmaceutical forms suitable for injectable use can include sterile aqueous solutions or dispersions and sterile powders for the extemporaneous preparation of sterile injectable solutions or dispersions. In some embodiments, the form is sterile and fluid to the extent that easy syringability exists.

In some embodiments, parenteral administration can be by continuous infusion over a selected period of time. Solutions suitable for parenteral administration can be prepared by known methods by a person skilled in the art. For example, the bicarbonate and/or an antimicrobial agent can be prepared in water optionally mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations can contain a preservative to prevent the growth of microorganisms.

Compositions for nasal administration can be conveniently formulated as aerosols, drops, gels or powders. Aerosol formulations typically comprise a solution or fine suspension of the active substance in a physiologically acceptable aqueous or non-aqueous solvent and are can be prepared in single or multidose quantities in sterile form in a sealed container, which take the form of a cartridge or refill for use with an atomising device. Alternatively, the sealed container can be a unitary dispensing device such as a single dose nasal inhaler or an aerosol dispenser fitted with a metering valve which is intended for disposal after use. Where the dosage form comprises an aerosol dispenser, it can contain a propellant which is, for example, a compressed gas such as compressed air or an organic propellant such as fluorochlorohydrocarbon. In some embodiments, the aerosol dosage forms can take the form of a pump-atomizer.

Compositions suitable for buccal or sublingual administration can include tablets, lozenges, and pastilles, wherein the active ingredient is formulated with a carrier such as sugar, acacia, tragacanth, gelatin and/or glycerine. Compositions for rectal administration can conveniently be in the form of suppositories containing a conventional suppository base such as cocoa butter.

In some embodiments provided herein, a composition useful for treating an ophthalmic infection is provided. In some embodiments, the composition contains an effective amount (i) bicarbonate and (ii) an antimicrobial agent as provided herein and a pharmaceutical excipient suitable for ocular administration. In some embodiments, pharmaceutical compositions suitable for ocular administration can be presented as discrete dosage forms, such as drops or sprays each containing a predetermined amount of the active ingredient(s) in a solution, or a suspension in an aqueous or non-aqueous liquid, an oil-in-water emulsion, or a water-in-oil liquid emulsion. Other administration forms can include intraocular injection, intravitreal injection, topically, or through the use of a drug eluting device, microcapsule, implant, or microfluidic device. In some embodiments, the compounds as provided herein can be administered with a carrier or excipient that increases the intraocular penetrance of the compound such as an oil and water emulsion with colloid particles having an oily core surrounded by an interfacial film. The compositions of the invention can be administered to the eye via topical, subconjunctival, periocular, retrobulbar, subtenon, intracameral, intravitreal, intraocular, subretinal, juxtascleral and suprachoroidal administration.

In some embodiments, eye drops can be prepared by dissolving the active ingredient(s) in a sterile aqueous solution such as physiological saline, buffering solution, etc., or by combining powder compositions to be dissolved before use. Other vehicles can be chosen, as is known in the art, including, but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives can include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

In another embodiment, bicarbonate and/or an antimicrobial agent can be orally administered, for example, with an inert diluent or with an assimilable edible carrier, or they can be enclosed in hard or soft shell gelatin capsules, or compressed into tablets, or incorporated directly with the food of a diet. For oral administration, the bicarbonate and an antimicrobial agent can be incorporated with excipients and used in the form of, for example, ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., molecular sieving type particles, or, a fine hollow permeable fiber bundle, or chopped hollow permeable fibers, agglomerated or held in a fibrous packet. In some embodiments, timed-release compositions can be, formulated, as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of lipids, such as cholesterol, stearylamine or phosphatidylcholines.

It is also possible to freeze-dry the bicarbonate and/or an antimicrobial agent and use the lyophilizate obtained, for example, for the preparation of products for injection In some embodiments, the bicarbonate and/or an antimicrobial agent can be coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. In a further embodiment, the bicarbonate and antimicrobial agent can be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In some embodiments, the bicarbonate and an antimicrobial agent are effective for treating a pulmonary, lung, otic, oral, nasal, sinus, ophthalmic, intraocular, dermal, cardiovascular, kidney, urinary, gastrointestinal, rectal, vaginal or neurological infection, and the compounds formulated accordingly. In some embodiments, the methods and compositions described herein are useful to treat a pulmonary, lung, otic, oral, nasal, sinus, ophthalmic, intraocular, dermal, cardiovascular, kidney, urinary, gastrointestinal, rectal, vaginal or neurological infection.

In some embodiments, the bicarbonate and/or an antimicrobial agent can be administered as a topical composition, such as a solution, gel, cream, lotion, liquid suspension, aerosol, nebulized spray, ointment, drops or patch.

Accordingly, in some embodiments, the bicarbonate and/or an antimicrobial agent can be administered intraocularly, for example, as an ophthalmic topical solution or gel (pulsed or sustained released delivery), or by topical, subconjunctival, periocular, retrobulbar, sub-tenon, intracameral, intravitreal, intraocular, subretinal, juxtascleral or suprachoroidal administration.

In some embodiments, the bicarboniate and/or the antimicrobial agent are found on a substrate. For example, a substrate may be glass, metal, plastic, latex or ceramic. In some aspects the bicarbonate and/or the microbial agent may be present on or in a surgical instrument. In some embodiments, the bicarbonate and/or the antimicrobial agent may be present on or in a catheter, an implant, a stent or a surgical mesh.

The bicarbonate and an antimicrobial agent can be used with each other. The bicarbonate and an antimicrobial agent can be either used or administered separately in time and/or in mode of administration (i.e., different administration routes) or they can be administered together in the same pharmaceutical preparation.

In some embodiments, bicarbonate and an antimicrobial agent can be used or administered separately in time and/or in mode of administration. For example, the bicarbonate can be administered by injection and the antimicrobial agent can be administered orally. In another example, the bicarbonate can be administered orally and the antimicrobial agent can be administered by injection. In a further example, both the bicarbonate and the antimicrobial agent can be administered by injection. In yet a further example, the bicarbonate is administered topically, e.g. as an aerosol or nebulized spray, and the antimicrobial agent is administered orally. When the bicarbonate and the antimicrobial agent are used or administered separately in time and/or in mode of administration, the bicarbonate can be administered, or used, either before or after administration, or use, of the antimicrobial agent.

In some embodiments, bicarbonate and an antimicrobial agent can be present in same pharmaceutical composition or each can be present in a separate composition. In one embodiment, bicarbonate and an antimicrobial agent are not present in the same composition.

The exact details of the administration will depend on the pharmacokinetics of the bicarbonate and the antimicrobial agent in the presence of each other, and can include administering bicarbonate and the antimicrobial agent within a few hours of each other, or even administering the bicarbonate and the antimicrobial agent within 24 hours or greater of administration of the other, if the pharmacokinetics are suitable. Design of suitable dosing regimens is routine for one skilled in the art.

In some embodiments, bicarbonate and an antimicrobial agent are administered to a subject in a single composition or formulation. In some embodiments, a single composition or formulation may comprise bicarbonate and one, two, three or more antimicrobial agents.

In some embodiments, bicarbonate and an antimicrobial agent are each administered to a subject in a separate composition or formulation.

Treatment methods can comprise administering to a subject, the bicarbonate and an antimicrobial agent, and optionally consists of a single administration, or alternatively comprises a series of administrations. The length of the treatment period can depend on a variety of factors, such as the severity of the infection, disease, disorder or condition, the age of the subject, the dosage of the bicarbonate and an antimicrobial agent, the activity of the bicarbonate and an antimicrobial agent and/or a combination thereof.

In some embodiments, the antimicrobial agent can be administered or used according to treatment protocol that is known for the antimicrobial agent in the treatment in microbial infections.

In some embodiments, the bicarbonate and an antimicrobial agent can be administered or used as soon as practicable after exposure to the microorganism. In some embodiments, the bicarbonate and an antimicrobial agent can be administered or used until treatment of the microbial infection is achieved. For example, until complete elimination of the microorganism is achieved, or until the number of microorganisms has been reduced to the point where the subject's defenses are no longer overwhelmed and can kill any remaining microorganisms.

The dosage of the bicarbonate and an antimicrobial agent can vary depending on many factors such as the pharmacodynamic properties thereof, the mode of administration, the age, health and weight of the subject, the nature and extent of the symptoms, the frequency of the treatment and the type of concurrent treatment, if any, and the clearance rate in the subject to be treated. One of skill in the art can determine the appropriate dosage based on the above factors. In some embodiments, the bicarbonate and an antimicrobial agent are administered initially in a suitable dosage that may be adjusted as required, depending on the clinical response.

In some embodiments, the dosage, or effective amount, of the antimicrobial agent can be equal to or less than the dosage of such agents when used alone. Such dosages are known to or readily determined by those skilled in the art.

In some embodiments, the dosage or amount of the bicarbonate can be an amount to provide physiological concentrations of bicarbonate, or about 25 mM of bicarbonate In some embodiments, the bicarbonate can be administered in a composition comprising about 1 mM to about 75 mM bicarbonate, or about 20 mM to about 50 mM bicarbonate. In some embodiments, the bicarbonate can be administered in a composition comprising about 0.01 wt % to about 1.0 wt % bicarbonate, or about 0.20 wt % to about 0.5 wt % bicarbonate. In some embodiments, the effective amount or dosage of bicarbonate can be about 0.01 mg to about 1 mg. In other embodiments, the effective amount or dosage of bicarbonate is in an amount of about 1.75 wt % to about 8.4 wt % of the composition.

In some embodiments, provided herein is a pharmaceutical composition comprising sodium bicarbonate and an antimicrobial agent wherein the antimicrobial agent's concentration in a cell of the microorganism is increased by one or both of (1) decrease in pH gradient across the microorganism's cytoplasmic membrane; and (2) increase in the microorganism's cytoplasmic membrane potential. In some embodiments, the composition comprises about 1 mM to about 150 mM bicarbonate, or about 20 mM to about 50 mM bicarbonate. In other embodiments, the effective amount or dosage of bicarbonate is in an amount of greater than 150 mM, for example, about 175 mM to about 900 mM.

In illustrative embodiments, the antimicrobial agent is pentamidine, erythromycin, dirithromycin, levofloxacin, norfloxacin, ciprofloxacin, enoxacin, moxifloxacin, besifloxacin or polymyxin B, combination thereof, analogs thereof, or a pharmaceutically acceptable salt of, and the composition comprises about 0.1 wt % to about 1.0 wt %, or about 0.5 wt %, pentamidine and about 0.01 wt % to about 1.0 wt % bicarbonate, or about 0.20 wt % to about 0.5 wt % bicarbonate.

In other illustrative embodiments, a kit is provided comprising an orally administrable composition comprising the antimicrobial agent azithromycin, an analog thereof, or a pharmaceutically acceptable salt of, and a topical composition comprising bicarbonate in an amount of greater than 150 mM, such as an amount of about 175 mM to about 900 mM, or an amount of about 1.75 wt % to about 8.4 wt % of the composition.

Screening for Antimicrobial Agents

Provided herein are methods of screening for antimicrobial agents or compounds.

In one embodiment, the method of screening for an antimicrobial agent comprises (1) contacting a microorganism with a test compound in the presence of bicarbonate; and (2) observing growth of the microorganism, wherein a decrease in the growth of the microorganism in the presence of the test compound compared to in the absence of the test compound indicates that the test compound is an antimicrobial agent.

In another embodiment, provided herein are methods of screening for antimicrobial compounds that can be modulated by bicarbonate comprising: (1) contacting a microorganism with either (i) a test compound not in the presence of bicarbonate or (ii) a test compound in the presence of bicarbonate; and (2) observing growth of the microorganism, wherein a greater change in the growth of the microorganism with the test compound in the presence of bicarbonate compared to the growth of the microorganism with the test compound not in the presence of bicarbonate indicates that the test compound is an antimicrobial compound that can be modulated by bicarbonate.

In some embodiments, a microorganism is a virus, a bacterium, a fungus or a parasite.

In some embodiments, the concentration of bicarbonate is about 20 mM to about 75 mM, or about 25 mM to about 50 mM, or about 20 mM to about 100 mM, or about 20 mM to about 150 mM, or about 50 to about 150 mM, or about 50 mM to about 100 mM.

In some embodiments a plurality of test compounds may be tested. In some embodiments, a plurality of microorganisms may be tested.

In some embodiments, the method of screening can be performed at different concentrations of the test compound and a minimum concentration for inhibition (MIC) of the microorganism is determined. In some embodiments, the MIC is the lowest concentration of a compound that prevents visible growth of the microorganism after overnight incubation.

In some embodiments, a FIC index calculation (shown below) is used to screen for an antimicrobial agent. In some embodiments, a FIC index value of less than or equal to 0.5 indicates synergy between a test compound and bicarbonate.

$$FIC\ \text{index} = FIC_{bicarbonate\,salt} + FIC_{test\ compound}$$

Fractional Inhibitory Concentration (FIC)=[X]/$MIC_X$, where [X] is the lowest inhibitory concentration of drug in the presence of the co-drug.

EXAMPLES

The following examples illustrate the scope of the application. Specific elements of the example are for descriptive purposes only and are not intended to limit the scope of the invention. Those skilled in the art could develop equivalent methods and utilize comparable materials that are within the scope of the application.

Example 1: Methods

In the following experiments, bacterial cells were cultured in 96-well microtiter plates in cation-adjusted Mueller-Hinton Broth (MHB) for 18 h at 37° C. The main strains used in this study were *E. coli* (K-12 BW25113) (placed in stationary incubator) and *S. aureus* (Strain Newman) (incubated at 250 r.p.m). Knockout strains (ΔtolcC and ΔychM) were used from the Keio knockout collection (Baba, T. et al. Construction of *Escherichia coli* K-12 in-frame, single-gene knockout mutants: the Keio collection. Mol Syst Biol 2, 2006 0008, doi:10.1038/msb4100050 (2006)). For minimum concentration for inhibition (MIC) determination and checkerboard analyses, Clinical & Laboratory Standards Institute (CLSI) protocol was used. Tetracycline uptake was assayed as previously described (Ejim, L. et al. Combinations of antibiotics and nonantibiotic drugs enhance antimicrobial efficacy. *Nature chemical biology* 7, 348-350, doi:10.1038/nchembio.559 (2011)). $DiSC_3$ loading of *S. aureus* cells was performed as previously described (Farha, M. A., Verschoor, C. P., Bowdish, D. & Brown, E. D. Collapsing the proton motive force to identify synergistic combinations against *Staphylococcus aureus*. *Chemistry & biology* 20, 1168-1178, doi:10.1016/j.chembiol.2013.07.006 (2013)). CCCP concentration of 20 μM was used. pH adjustments were made by addition of HCl or NaOH. INT assay and ATP bioluminescence assays were performed as previously described (Farha, M. A., Verschoor, C. P., Bowdish, D. &

Brown, E. D. Collapsing the proton motive force to identify synergistic combinations against *Staphylococcus aureus. Chemistry & biology* 20, 1168-1178, doi:10.1016/j.chembiol.2013.07.006 (2013)). For chemical-genomic studies, the Keio library was grown overnight in cation-adjusted MHB broth, in 384-well plates. From these, treatment plates (25 mM sodium bicarbonate, or a sterile water control) were inoculated and grown for 15 hours at 37° C., in a stationary incubator. Data was normalized according to Mangat et al (Mangat, C. S., Bharat, A., Gehrke, S. S. & Brown, E. D. Rank ordering plate data facilitates data visualization and normalization in high-throughput screening. *J Biomol Screen* 19, 1314-1320, doi:10.1177/1087057114534298 (2014)), with gene products and GO terms mined from EcoCyc. The GFP promoter library (Keseler, I. M. et al. EcoCyc: fusing model organism databases with systems biology. Nucleic Acids Res 41, D605-612, doi:10.1093/nar/gks1027 (2013)) was grown for 18 hours at ambient temperature with the same inoculation strategy as with the Keio collection. The analysis pipeline of Zaslaver et al (Zaslaver, A. et al. A comprehensive library of fluorescent transcriptional reporters for *Escherichia coli. Nat Methods* 3, 623-628, doi:10.1038/nmeth895 (2006)) was used to generate maps of promoter activity, from which lists of promoters with increased or decreased activity were compiled.

Example 2: Pentamidine Monotherapy in a Murine Model of Systemic *A. baumannii* Infection Pentamidine (Formula I) has been recognized as having antibacterial activity for approximately 70 years but has not yet been pursued as an antibacterial in the clinic. Knowledge that the concentrations of pentamidine required for inhibiting the growth of bacteria in vitro are high.

A screen of a collection of previously-approved non-antibiotic drugs to identify small molecule perturbants of outer membrane architecture uncovered the antiprotozoal/antifungal drug pentamidine (I). The screen was devised based on observations that *E. coli* grown during periods of cold stress is rendered susceptible to glycopeptide antibiotics, a phenomenon that can be reversed by inactivating genes involved in outer membrane biosynthesis (Stokes, J M., et al., Cell Chem. Biol., Feb. 18, 2016, 23(2), 267-277).

Using atomic force microscopy (AFM), the direct effect of pentamidine on the outer membrane of *E. coli* has been observed for the first time. Severe surface defects were observed upon incubation with pentamidine that are similar to those seen with the membrane-damaging agent, polymyxin B. Structure-activity relationship studies have provided further support for these observations and suggested that the cationic properties of pentamidine may promote its interaction with the anionic head groups of the bacterial membrane lipids, and enable integration into the hydrophobic core of the membrane. This indicated that membrane perturbation is the principal mechanism of action of pentamidine.

Here, *A. baumannii* was injected into mice intraperitoneally ($1.5\times10^6$ CFU *A. baumannii*) and after two-hours mice were treated intraperitoneally with a single dose of PBS (n=10), novobiocin at 5 mg/kg (n=10), pentamidine isethionate at 10 mg/kg (n=10), pentamidine at 50 mg/kg (n=10) or a combination of both molecules where pentamidine is at 10 mg/kg and novobiocin, (n=10). Mice were treated two-hours post-infection to allow complete organ occupancy by the injected cells.

Figure 1B:
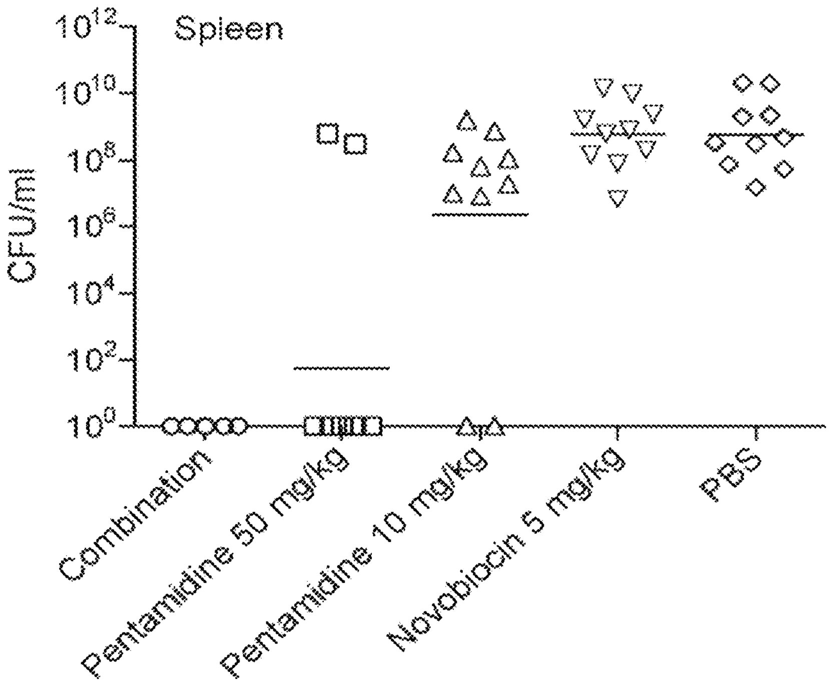
FIG. 1B shows graphically that pentamidine alone and in the presence of novobiocin causes clearance of bacteria from the spleen.

FIG. 1A shows that when mice were treated IP with 50 mg/kg pentamidine alone, rescue in 80% of the animals was observed. FIG. 1B shows that *A. baumannii* organ load (e.g. spleen) was found to decrease seven logs as a result of pentamidine alone, and total clearance as a result of the combination.

Example 3: Pentamidine Activity in Different Culture Media

While pentamidine had relatively little or no in vitro activity in standard microbiological media against the Gram-negative organisms, *E. coli, A. baumannii, K pneumoniae, P. aeruginosa* and *B. cenocepacia*, these bacteria were highly susceptible to pentamidine when grown in a tissue culture media formulated to mimic the natural environment (Table 1). For instance, the minimum inhibitory concentration (MIC) of pentamidine against *E. coli* in the standard microbiological media Mueller Hinton Broth (MHB) of 200 μg/mL was significantly reduced in the tissue culture media formulated to mimic the natural environment to 1 μg/mL. Against *A. baumannii*, a >50-fold enhanced potency in tissue culture media formulated to mimic the natural environment was observed. Potent activity was also observed against Gram-positive organisms, such as *S. aureus*.

TABLE 1

Effects of pentamidine

| | MHB (μg/mL) | Tissue culture media formulated to mimic the natural environment (μg/mL) |
|---|---|---|
| *Escherichia coli* | 200 | 1.5 |
| *Acinetobacter baumannii* | 100 | 12.5 |
| *Klebsiella pneumoniae* | >200 | 12.5 |
| *Pseudomonas aeruginosa* | >200 | 12.5 |
| *Burkhloderia cenocepacia* | >200 | 12.5 |
| *Burkhloderia multivorans* | >200 | 12.5 |
| *Enterococcus faecalis* | 25 | 3.1 |
| *Staphylococcus aureus* | 12.5 | <0.1 |

Example 4: Sodium Bicarbonate Potentiated the Activity of Pentamidine Against *E. coli*

Figure 2:
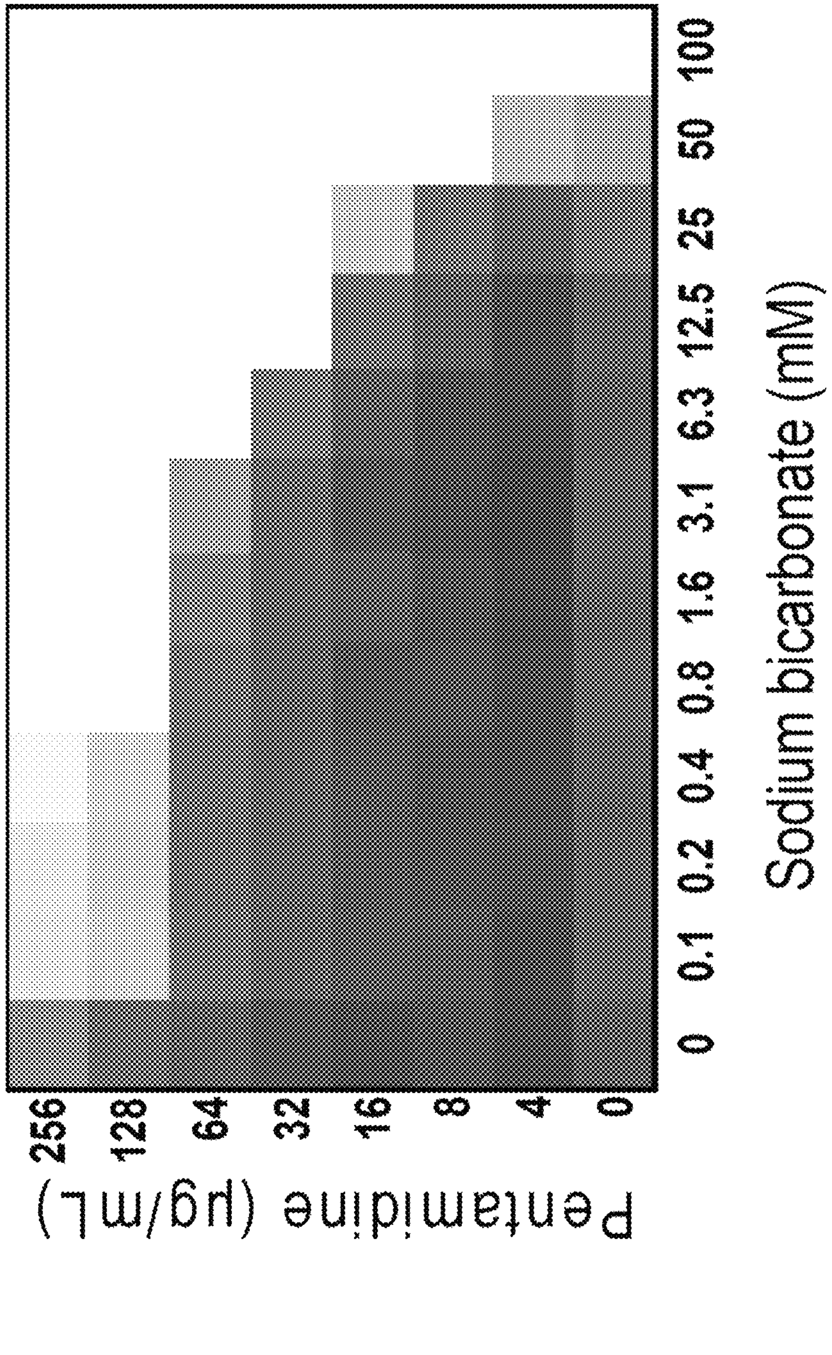
FIG. 2 shows checkerboard microdilution assays and demonstrates, in an illustrative embodiment, the effect of added sodium bicarbonate on pentamidine activity against *E. coli*, where dark regions represent higher growth. A synergistic interaction is observed.

The components of the tissue culture media formulated to mimic the natural environment were deconvoluted and tested at varying concentrations to assess their individual effects on the antibacterial activity of pentamidine. Most notably, sodium bicarbonate, which is present at physiological concentrations (25 mM) in the tissue culture media formulated to mimic the natural environment, and absent in standard microbiological media, greatly potentiated the activity of pentamidine, in a dose-dependent manner, against *E. coli* (FIG. 2). The ability of bicarbonate to potentiate the activity of pentamidine largely reconciled the paradox between the lack of activity observed in standard media in vitro and the significant in vivo activity of pentamidine as a single agent. Importantly, bicarbonate plays a central position in mammalian physiology and is ubiquitously present in the body.

Table 2 shows the effect of various salts on the antibacterial activity of pentamidine against *S. aureus*. Shown are the Fractional Inhibitory Concentration (FIC) indexes from the combination of pentamidine with each salt where FICI≤0.5 represents synergy, =1-2 additivity and >4 antagonism. Through the testing of various salts, with differing ionic strengths and other differing properties, on the activity of pentamidine, it was observed that sodium bicarbonate, was unique and provided the greatest influence on the activity of pentamidine. The sodium counterion did not contribute to the potentiation of pentamidine, as equally potent synergy was observed with varying salts of bicarbonate.

TABLE 2

Effects of various salts on the antibacterial activity of pentamidine against *S. aureus*

| | FIC Index (with pentamidine in *S. aureus*) |
|---|---|
| Sodium bicarbonate ($NaHCO_3$) | 0.31 |
| Ammonium bicarbonate ($NH_4HCO_3$) | 0.28 |
| Sodium bromide (NaBr) | 2 |
| Sodium fluoride (NaF) | 1 |
| Sodium acetate ($C_2H_3NaO_2$) | 2 |
| Sodium sulfate ($Na_2SO_4$) | 2 |
| Sodium chloride (NaCl) | 2 |
| Isethionic acid ($C_2H_6O_4S$ ) | 2 |
| Boric acid ($H_3BO_3$) | 1 |
| Sodium nitrate ($NaNO_3$) | 2 |
| Sodium phosphate ($NaH_2PO_4$) | >8 |
| Potassium phosphate ($KH_2PO_4$) | >8 |

FIC index = $FIC_{salt}$ + $FIC_{pentamidine}$
Fractional Inhibitory Concentration (FIC) = [X]/$MIC_X$, where [X] is the lowest inhibitory concentration of drug in the presence of the co-drug.

Example 5: The Impact of Pentamidine on the Proton Motive Force of *E. coli* MC1061

Fluorescence spectroscopy using the membrane-potential sensitive dye 3,3'-dipropylthiadicarbocyanine iodide was used to measure pentamidine's ability to dissipate transmembrane potential. *E. coli* MC1061 cells were washed twice and suspended in a buffer containing 20 mM glucose and 5 mM HEPES (pH 7.2). Final resuspension was diluted to an optical density at 600 nm of 0.085. $DiSC_3(5)$ was added at a final concentration of 1 μM, and the dye was left to stabilize (1 hr at 37° C.). Compounds were then injected at concentrations equivalent to their MIC. Fluorescent traces were measured in a fluorimeter (Photon Technology International) at the excitation and emission wavelengths of 622 and 660 nm, respectively.

Figures 3A, 3B:
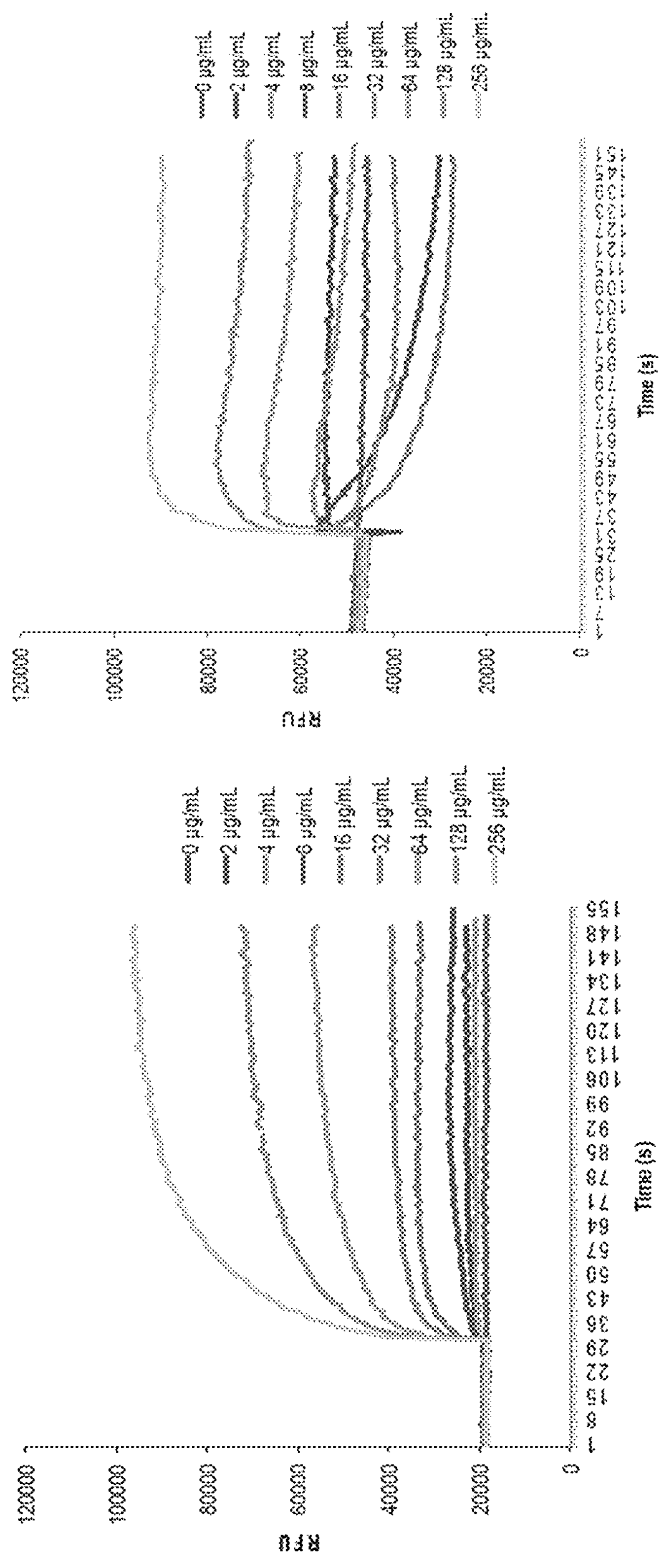
FIG. 3A and FIG. 3B show the dissipation of the bacterial membrane potential by pentamidine without (A) or with (B) the addition of sodium bicarbonate, in an illustrative embodiment of the invention.

It was reasoned that the much-reduced MIC of pentamidine in the presence of an ionic milieu reminiscent of the in vivo environment might indicate an alternate mode of action than observed in standard media. Recognizing that the ability of pentamidine to perturb the outer membrane was retained in standard microbiological media, it was queried whether the ionic environment of the host might confer on pentamidine additional activity against the cytoplasmic membrane. To test this, the impact of pentamidine on the proton motive force (PMF) of *E. coli* was investigated. Fluorescence spectroscopy using the membrane-potential sensitive dye 3,3'-dipropylthiadicarbocyanine iodide revealed that pentamidine dissipates transmembrane potential. Briefly, due to the potential gradient, the dye is taken up by bacteria and accumulation in the membrane leads to a decrease in fluorescence intensity due to self-quenching. A subsequent increase in fluorescence intensity is observed only if the dye is displaced into the solution as a result of dissipation of the membrane potential. Pentamidine dissipated the membrane potential of *E. coli* whether grown in standard growth media or when supplemented with 25 mM sodium bicarbonate (FIG. 3A, FIG. 3B). While not wishing to be limited by theory, the observation that pentamidine is synergistic with sodium bicarbonate may be related to its ability to dissipate the psi component of PMF ($\Delta\psi$), whereas sodium bicarbonate can dissipate the pH gradient leading to a complete collapse of PMF.

Figures 4A, 4B:
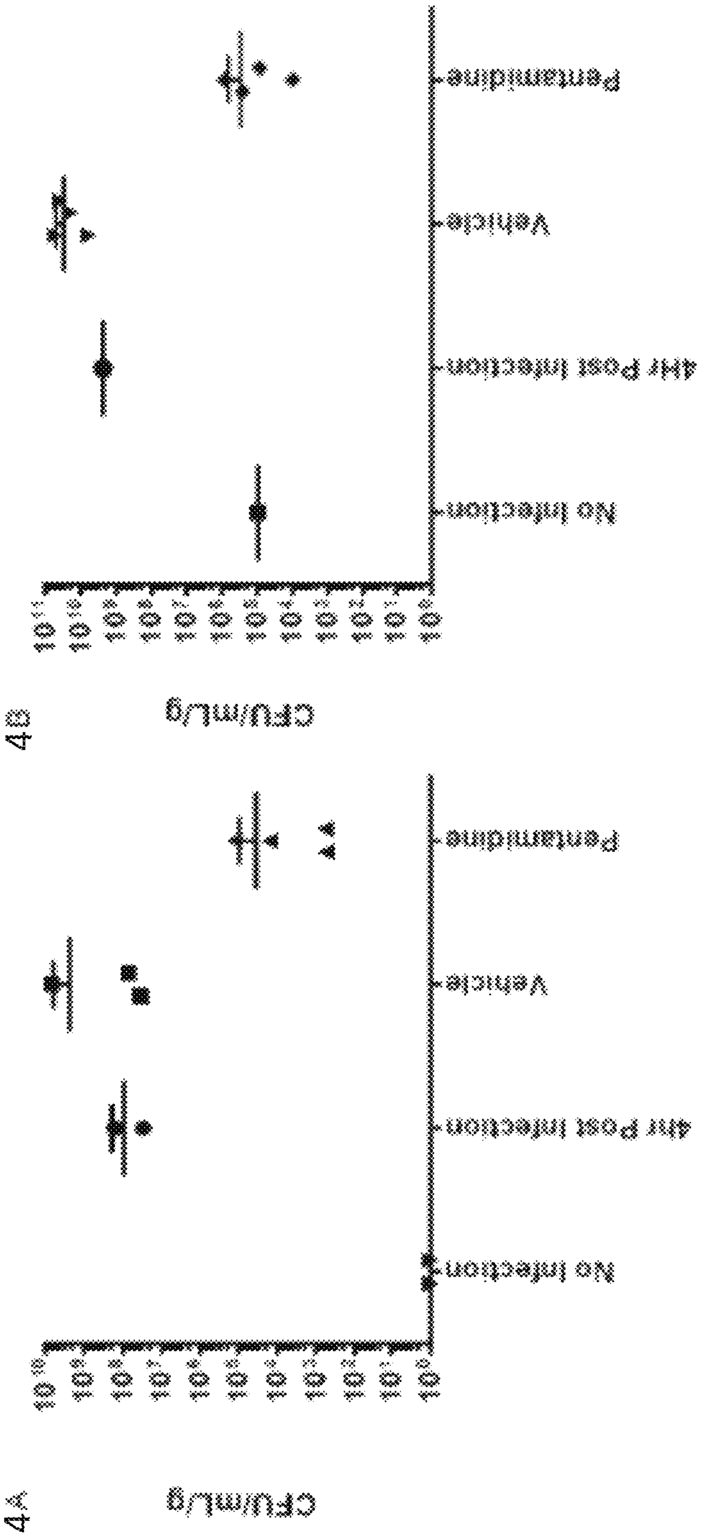
FIG. 4A and FIG. 4B graphically demonstrates the bacterial load following infection in tape-stripped mice, with and without pentamidine topical treatment, in an illustrative embodiment of the invention.
Figure 5:
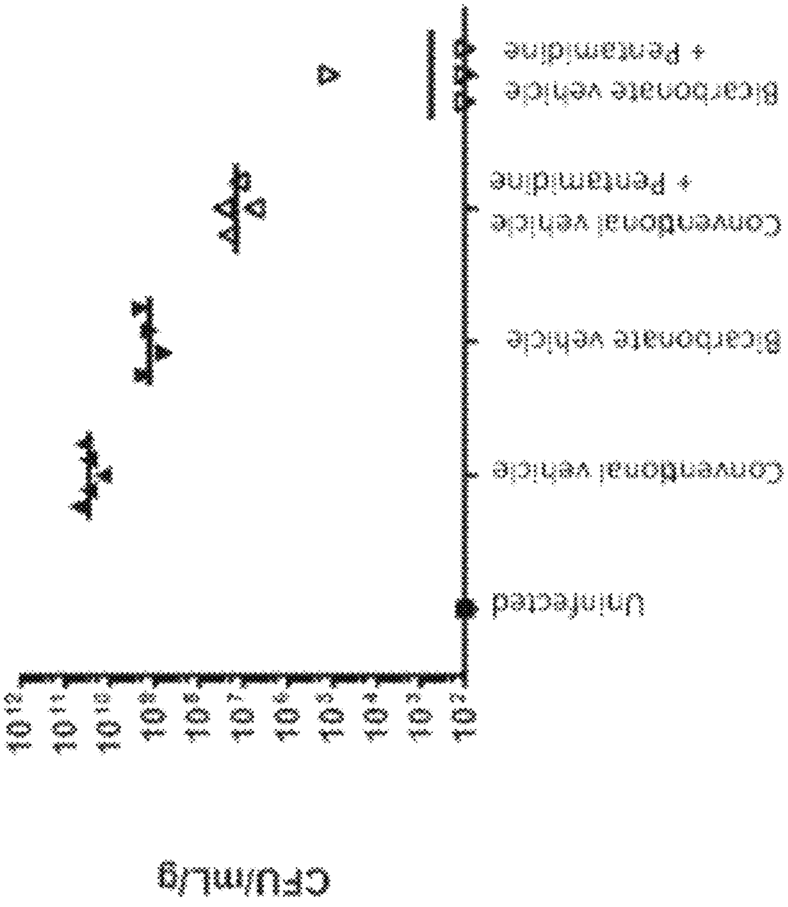
FIG. 5 shows the effect of a topical pentamidine-sodium bicarbonate formulation on bacterial load following infection in tape-stripped mice, in an illustrative embodiment of the invention.

Example 6: Efficacy of Pentamidine to Inhibit Growth of Gram-Negative and -Positive Pathogens The potential of pentamidine as a therapeutic agent was tested in a variety of superficial skin infection models. In this model, an infection is established by disrupting the skin barrier through partial removal of the epidermal layer by stripping with adhesive tape and with subsequent application of the pathogen. Tape-stripped mice infected with $4\times10^6$ CFU/mL *A. baumannii* (FIG. 4A) or 4×106 CFU/mL methicillin-resistance *Staphylococcus aureus* (MRSA) USA-300 (FIG. 4B). The No Infection group (n=1) shows the natural bacterial load after tape-stripping with no inoculum applied. Twenty μL of 0.5% Pentamidine in 1.9% Boric Acid, pH 7.0 was applied to the wound area 4, 5, 6, 7, 8, 9, and 19, 20, 21, 22, 23, 24 hours post infection (n=4). This treatment regime was also conducted for the Vehicle (1.9% Boric Acid, pH 7) as a control (n=4). Tissue samples were collected at 25 hr post-infection (FIG. 4A) and 28 hr post-infection (FIG. 4B). In the *A. baumannii* skin infection model, where mice were treated with 0.5% pentamidine, a 4-log reduction in CFU/mL compared to vehicle-treated mice was observed (FIG. 4A). In a *S. aureus* skin infection model, 0.5% pentamidine treatment caused a 5-log reduction in CFU/mL (FIG. 4B). Further, addition of bicarbonate in the solution increased the antibacterial efficacy of pentamidine in clearing an MRSA infection (pentamidine was applied as a topical 0.5% aqueous solution on skin with or without bicarbonate (50 mM)). (FIG. 5). Overall, pentamidine offers an effective, localized and well-tolerated topical approach for both Gram-negative and Gram-positive pathogens.

Figure 6A:
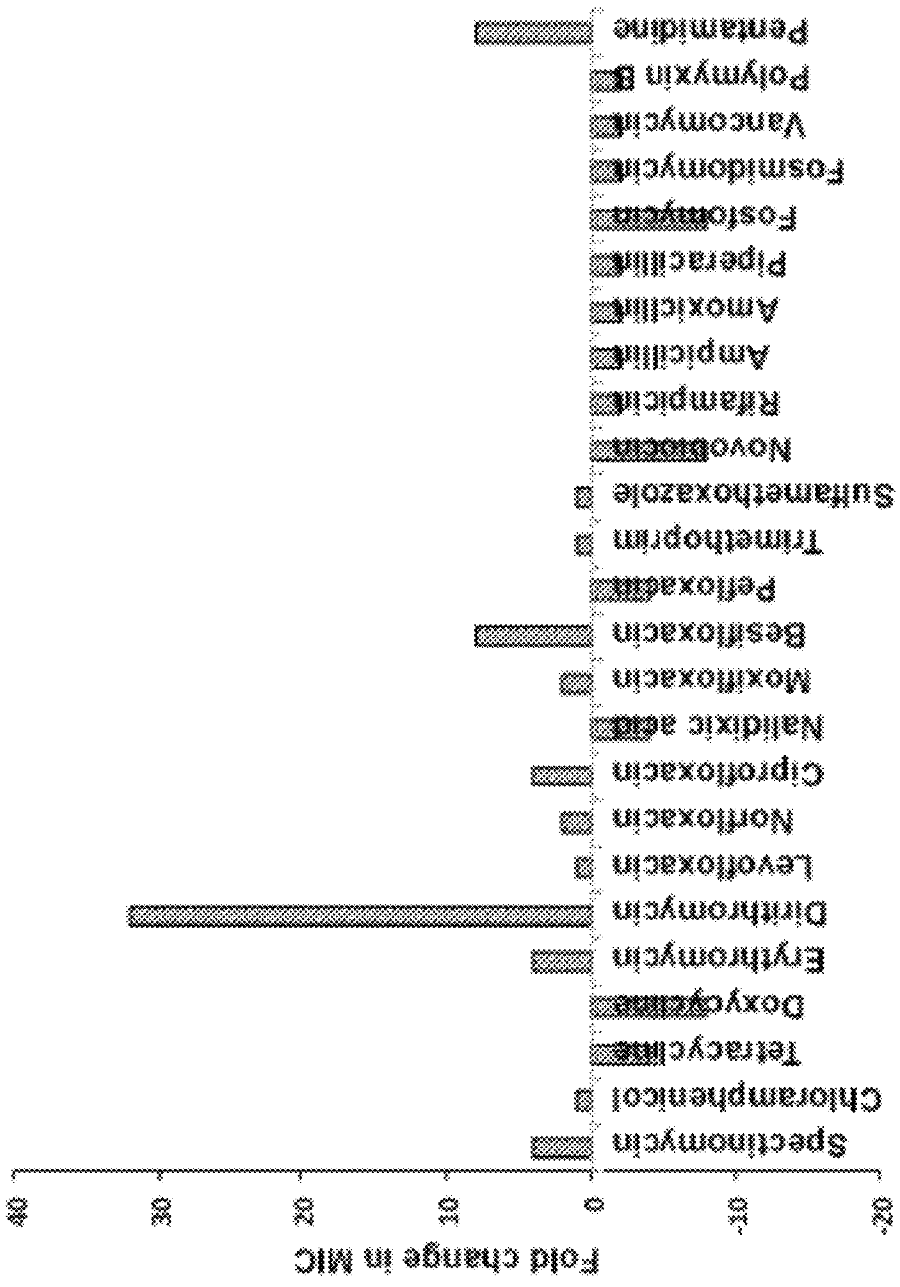
FIG. 6A shows the potentiation or suppression of antibiotics against *E. coli* in the presence of 25 mM sodium bicarbonate, an illustrative embodiment of the invention.
Figure 6B:
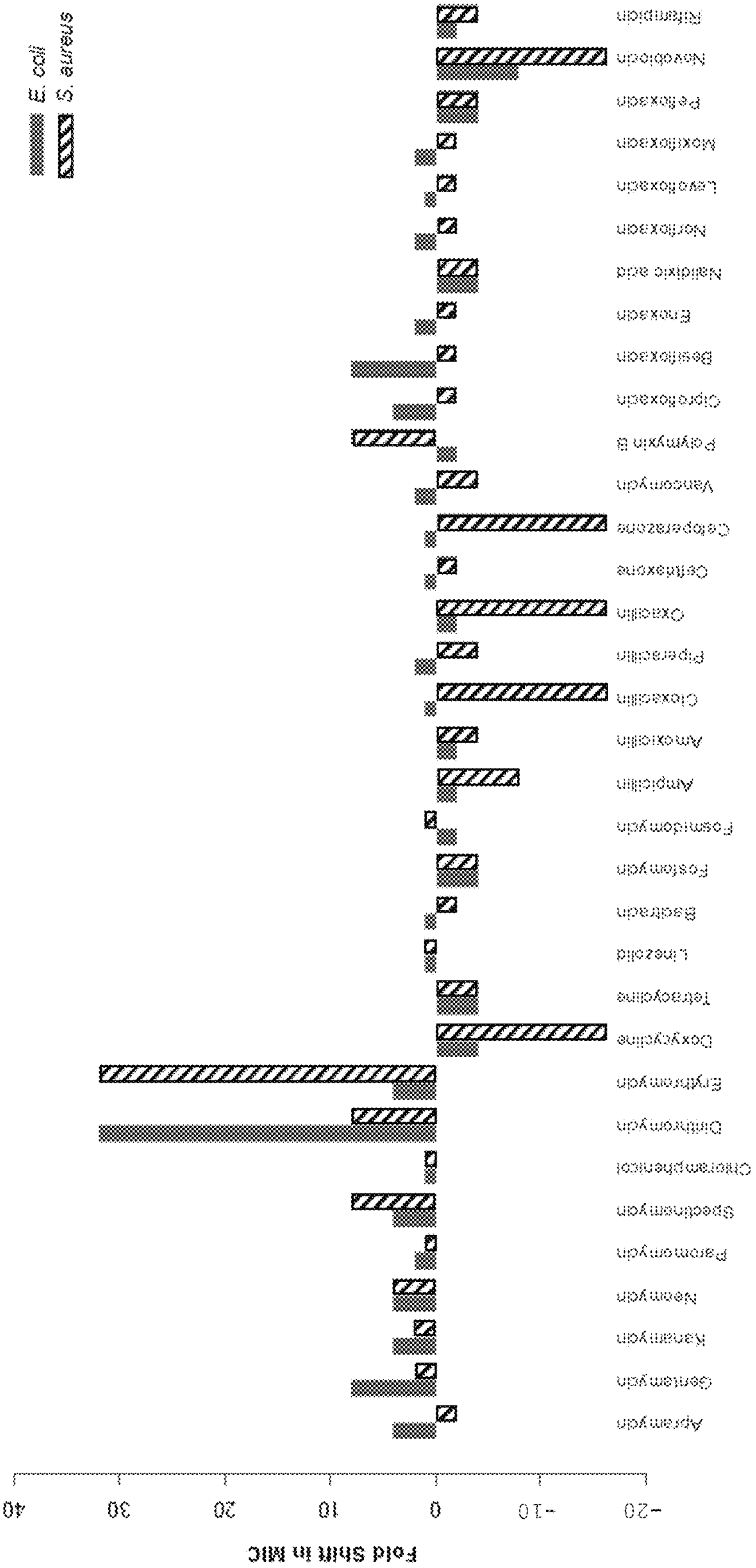
FIG. 6B shows similarly that bicarbonate affects the activity of various classes of antibiotics in *E. coli* and *S. aureus*.

Example 7: The Effect of Addition of Sodium Bicarbonate on Conventional Antibiotics The minimum inhibitory concentrations (MIC) of the antibiotics listed in FIG. 6A were determined in Mueller-Hinton broth (MHB) media and compared to the MIC in MHB supplemented with physiological concentrations of sodium bicarbonate (25 mM) (MHB+25 mM Sodium bicarbonate). Results of different experiments are shown in FIGS. 6A and 6B. Fold enhancement in MICs in the media supplemented with sodium bicarbonate is represented by a positive fold, whereas suppression of activity is represented by a negative fold.

FIG. 6A shows the fold changes in *Escherichia coli* in one experiment. The trends were similar in the Gram-positive *Staphylococcus aureus*. Additional data are shown in FIG. 6B and Table 3: the fold enhancement in the minimum inhibitory concentration (MIC) for a variety of antibiotics in standard microbiological media relative to media supplemented with 25 mM sodium bicarbonate is shown for *E. coli* and *S. aureus*. As shown in FIG. 6B, eight classes of antibiotics investigated had appreciably altered activities in the presence of 25 mM sodium bicarbonate. In FIG. 6B, the minimum inhibitory concentrations (MIC) of the listed antibiotics were determined in Mueller-Hinton broth (MHB) media and compared to the MIC in MHB supplemented with physiological concentrations of sodium bicarbonate (25 mM). Fold enhancement in MICs in the media supplemented with sodium bicarbonate is represented by a positive value, whereas suppression of activity is represented by a negative value. Shown are the fold changes in *E. coli* (solid) and fold changes in *S. aureus* (checkered).

With a few exceptions, these Gram-negative and Gram-positive bacteria behaved similarly. Of the antibiotics tested, the antibacterial activity of some fluoroquinolones, macrolides, and aminoglycosides was enhanced. The activity of polymyxin B was enhanced strictly in *S. aureus*. In contrast, the antibacterial activity of other fluoroquinolones, various cell wall active drugs, tetracyclines, fosfomycin and novobiocin was suppressed in the presence of bicarbonate. The antibacterial effect on other classes such as chloramphenicol, linezolid, the antifolate drugs, trimethoprim and sulfamethoxazole, remained largely unchanged.

Figure 7:
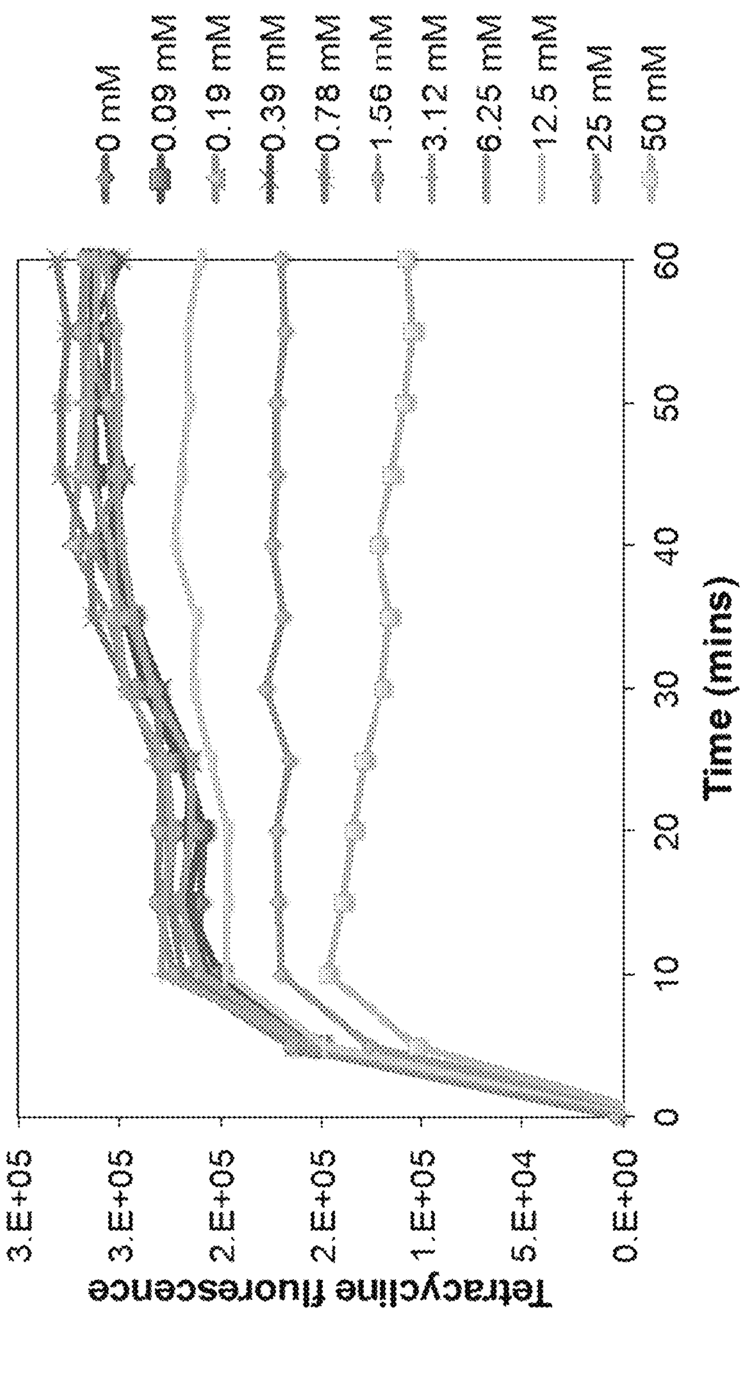
FIG. 7 shows the suppression of tetracycline entry in the presence of varying concentrations of sodium bicarbonate, in an illustrative embodiment of the invention.
Figure 11:
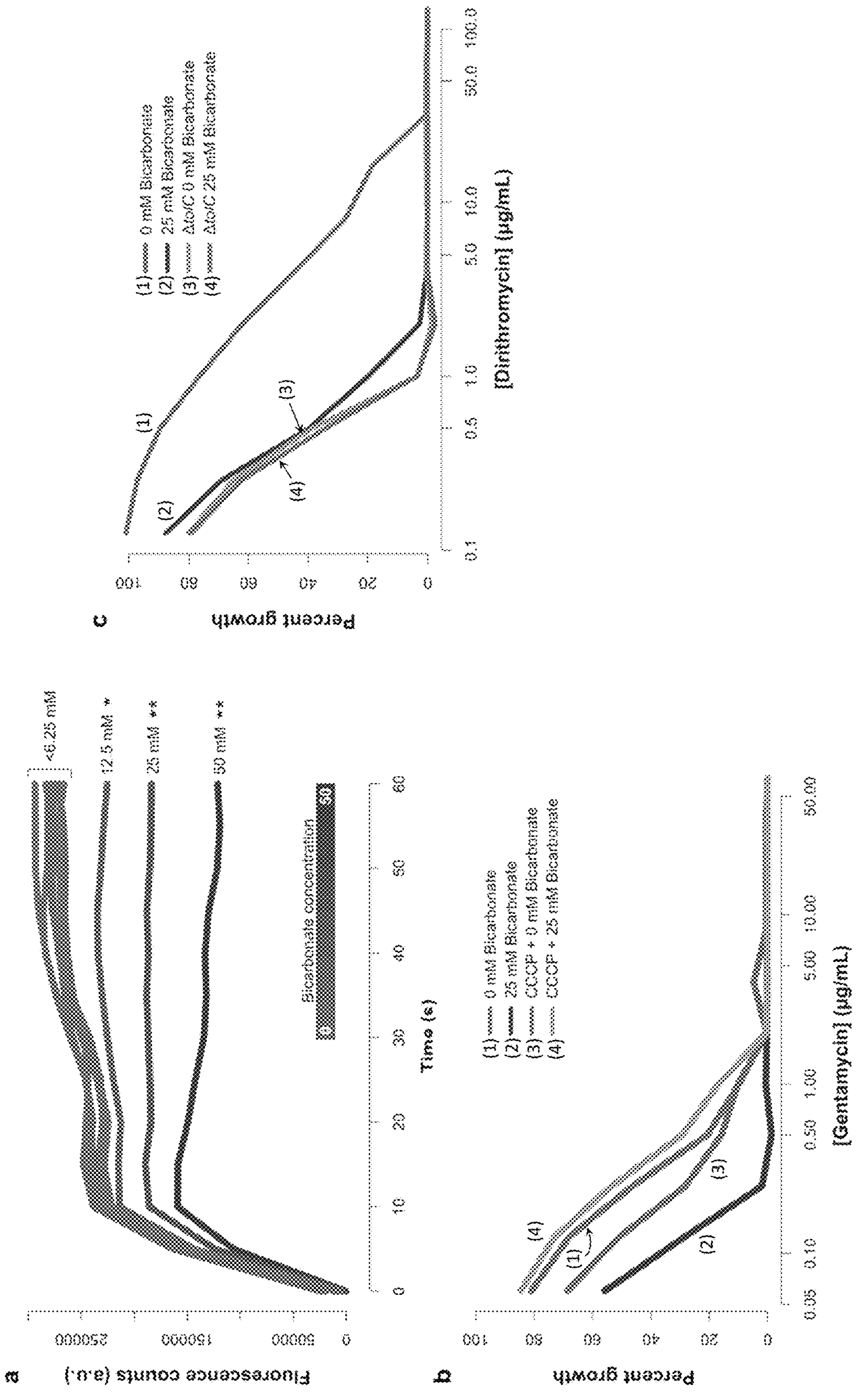
FIG. 11, Panels a-c show that bicarbonate dissipates the pH gradient across the cytoplasmic membrane affecting the activity of antibiotics.

FIG. 7. Tetracycline uptake was assayed by monitoring the fluorescence enhancement of tetracycline when it enters the cell. Averages of duplicate experiments are shown in FIG. 7. In a similar experiment, a direct test of the cellular uptake of tetracycline revealed that that suppression observed was due to inhibition of tetracycline uptake on addition of bicarbonate (FIG. 11, Panel a). In Panel a, sodium bicarbonate diminished the uptake of tetracycline in *E. coli*. Concentration of tetracycline was 125 μg/ml, and concentration of sodium bicarbonate was as indicated. Tetracycline uptake was assayed by monitoring the fluorescence enhancement of tetracycline when it enters the cell. Averages of triplicate experiments are shown.

TABLE 3

MIC of various antibiotics in MHB vs MHB + 25 mM sodium bicarbonate against *E. coli* and *S. aureus*.

Figure 6C:
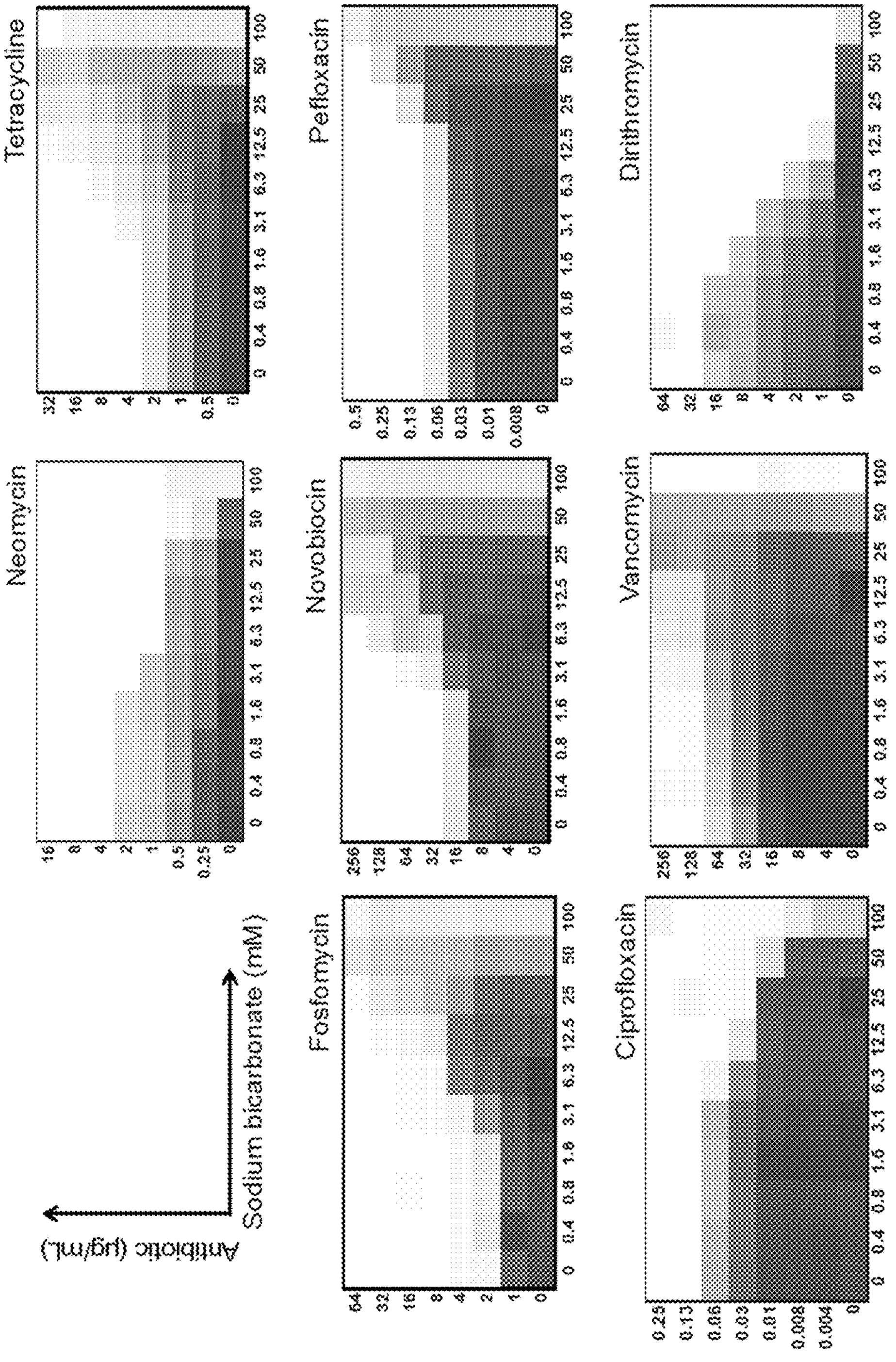
FIG. 6C shows a microdilution checkerboard analyses for antibiotics when used with sodium bicarbonate against *E. coli.*

| | *E. coli* | | | *S. aureus* | | |
|---|---|---|---|---|---|---|
| | MHB− | MHB+ | Fold | MHB− | MHB+ | Fold |
| Apramycin | 32 | 8 | 4 | 16 | 32 | 0.5 |
| Gentamicin | 2 | 0.25 | 8 | 2 | 1 | 2 |
| Kanamycin | 4 | 1 | 4 | 8 | 4 | 2 |
| Neomycin | 1 | 0.25 | 4 | 2 | 0.5 | 4 |
| Paromomycin | 2 | 1 | 2 | 2 | 2 | 1 |
| Spectinomycin | 16 | 4 | 4 | 64 | 8 | 8 |
| Chloramphenicol | 8 | 8 | 1 | 8 | 8 | 1 |
| Dirithromycin | 128 | 4 | 32 | 4 | 0.5 | 8 |
| Erythromycin | 128 | 32 | 4 | 32 | 1 | 32 |
| Doxycycline | 1 | 4 | −4 | 0.125 | 2 | −16 |
| Tetracycline | 1 | 4 | −4 | 0.5 | 2 | −4 |
| Linezolid | 256 | 256 | 1 | 0.625 | 0.625 | 1 |
| Bacitracin | >256 | >256 | 1 | 32 | 64 | −2 |
| Fosfomycin | 4 | 16 | −4 | 16 | 64 | −4 |
| Fosmidomycin | 16 | 32 | −2 | >64 | >64 | 1 |
| Ampicillin | 16 | 32 | −2 | 1 | 8 | −8 |
| Amoxicillin | 8 | 16 | −2 | 0.25 | 1 | −4 |
| Cloxacillin | 256 | 256 | 1 | 0.031 | 0.5 | −16 |
| Piperacillin | 2 | 1 | 2 | 0.25 | 1 | −4 |
| Oxacillin | 256 | >256 | −2 | 0.0625 | 1 | −16 |
| Ceftriaxone | 0.625 | 0.625 | 1 | 4 | 16 | −4 |
| Cefoperazone | 0.125 | 0.125 | 1 | 0.25 | 4 | −16 |
| Vancomycin | 256 | 256 | 1 | 1 | 4 | −4 |
| Polymyxin B | 0.25 | 0.5 | −2 | 256 | 32 | 8 |
| Ciprofloxacin | 0.0625 | 0.0156 | 4 | 0.5 | 1 | −2 |
| Besifloxacin | 0.25 | 0.0313 | 8 | 0.125 | 0.25 | −2 |
| Enoxacin | 0.25 | 0.125 | 2 | 1 | 2 | −2 |
| Nalidixic acid | 2 | 8 | −4 | >8 | 32 | −4 |
| Norfloxacin | 0.125 | 0.0625 | 2 | 0.5 | 1 | −2 |
| Levofloxacin | 0.0313 | 0.0313 | 1 | 0.5 | 1 | −2 |
| Moxifloxacin | 0.0313 | 0.0156 | 2 | 0.125 | 0.0625 | 2 |
| Pefloxacin | 0.125 | 0.5 | −4 | 0.5 | 2 | −4 |
| Novobiocin | 32 | >256 | −8 | 0.031 | 0.5 | −16 |
| Rifampicin | 32 | 64 | −2 | 0.0078 | 0.031 | −4 |

Where antibiotics were potentiated or suppressed, follow-up studies using systematic microbroth checkerboard techniques were completed to assess the dose-dependence of the interaction (FIG. 6C). Indeed, in all cases, enhancement or suppression was further pronounced with increasing concentrations of sodium bicarbonate. FIG. 6C shows representative antibiotics whose activity was altered in the presence of 25 mM sodium bicarbonate. The extent of inhibition is shown as a heat plot, such that the darkest color represents full bacterial growth.

Example 8: Sodium Bicarbonate Diminishes the Uptake of Tetracycline in *E. coli*

The concentration of tetracycline was 125 μg/ml, and concentration of sodium bicarbonate was as indicated in

Example 9: Bicarbonate Potentiates the Action of Dirithromycin

Figure 8A:
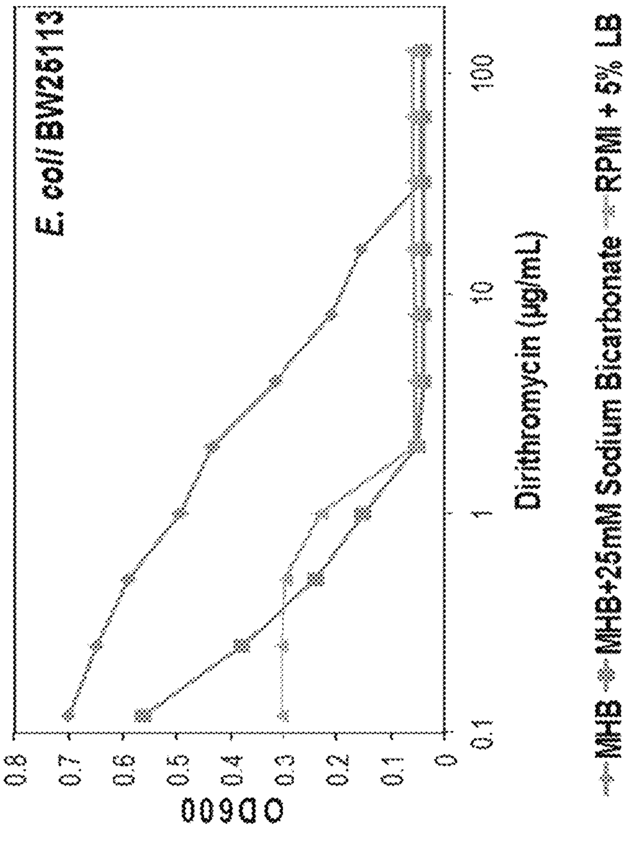
FIG. 8A shows the potentiation of the activity of dirithromycin in the presence of 25 mM sodium bicarbonate and FIG. 8B shows the disappearance of potentiation in a mutant of *E. coli* lacking the efflux pump tolC, an illustrative embodiment of the invention.
Figure 8B:
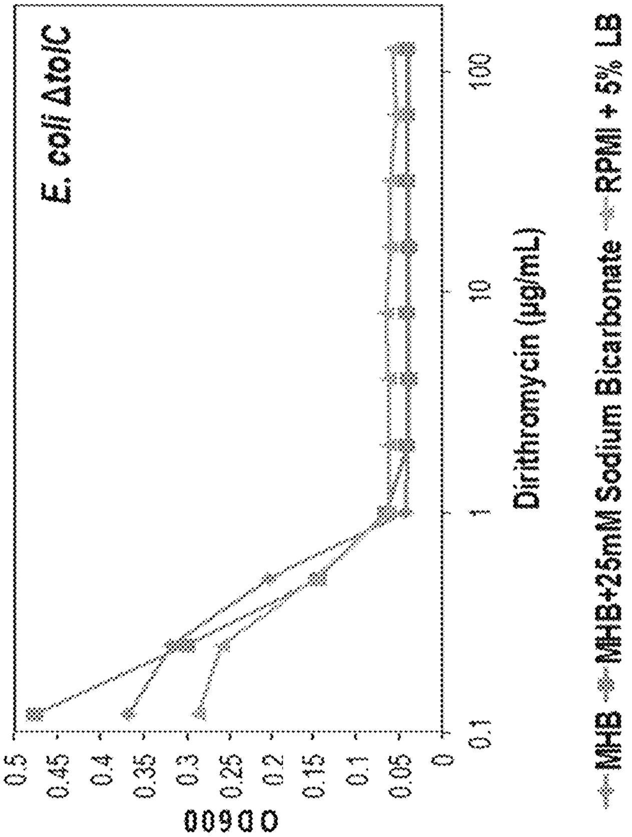

Results shown in FIG. 8A show that a growth inhibitory concentration of the macrolide dirithromycin is potentiated in the presence of sodium bicarbonate in wild-type *E. coli* and in FIG. 8B, show potentiation by sodium bicarbonate disappears in a strain deficient for the main efflux pumps *E. coli* ΔtolC.

The enhancement of dirithromycin by sodium bicarbonate was further assessed for the pathogens *Acinetobacter baumannii, Klebsiella pneumoniae* and *Pseudomonas aeruginosa* (FIG. 8C, Panels a-c). FIG. 8C, Panels a-c show the combination of the macrolide, dirithromycin, and sodium bicarbonate against multi-drug resistant clinical isolates of (a) *Acinetobacter baumannii* (b) *Klebsiella pneumoniae* and (c) *Pseudomonas aeruginosa*. In all cases, bicarbonate was a potentiator of the action of this macrolide antibiotic.

Example 10: Bicarbonate is Responsible for the Enhancements Observed

Whether the chemical bicarbonate was responsible for the enhancements observed in the above examples was assessed. It was observed that the activity was not due to simply an effect on pH. Test media were pH-adjusted upon addition of sodium bicarbonate for all studies reported herein. Of note, sodium bicarbonate at physiological concentration (25 mM) produced media with a pH typical of standard susceptibility testing conditions (Table 4).

TABLE 4 pH of MHB media amended with various concentrations of sodium bicarbonate, prior to pH-adjusting to 7.4.

| Concentration (mM) | pH |
|---|---|
| 0 | 7.42 |
| 1.56 | 7.42 |
| 3.12 | 7.42 |
| 6.25 | 7.43 |
| 12.5 | 7.47 |
| 25 | 7.53 |
| 50 | 7.61 |
| 100 | 7.71 |

Further, using dirithromycin, many equimolar organic salts were tested, with differing ionic strengths and steric properties, and none had impact on antibacterial activity, ruling out osmotic-mediated mechanisms (Table 5). Lastly, sodium did not contribute to the potentiation of dirithromycin, as equally potent synergy was observed with other salts of bicarbonate (Table 5).

TABLE 5

Minimum inhibitory concentration of dirithromycin in the presence of various salts at 25 mM against *E. coli*. In all cases, pH was adjusted to 7.4.

| Salt | Formula | MIC (μg/mL) |
|---|---|---|
| Control | — | 128 |
| Sodium bicarbonate | $NaHCO_3$ | 4 |
| Sodium bromide | NaBr | 128 |
| Sodium chloride | NaCl | 128 |
| Sodium fluoride | NaF | 128 |
| Sodium nitrate | $NaNO_3$ | 128 |
| Sodium acetate | $C_2H_3NaO_2$ | 64 |
| Sodium sulfate | $Na_2SO_4$ | 128 |
| Isethionic acid | $C_2H_6O_4S$ | 128 |
| Boric acid | $H_3BO_3$ | 128 |
| Sodium phosphate | $NaH_2PO_4$ | >128 |
| Potassium phosphate | $KH_2PO_4$ | >128 |
| Ammonium bicarbonate | $KHCO_3$ | 8 |
| Potassium bicarbonate | $NH_4HCO_3$ | 4 |

Example 11: Minimum Inhibitory Concentration of Pentamidine Against *S. cerevisiae*

Figure 9:
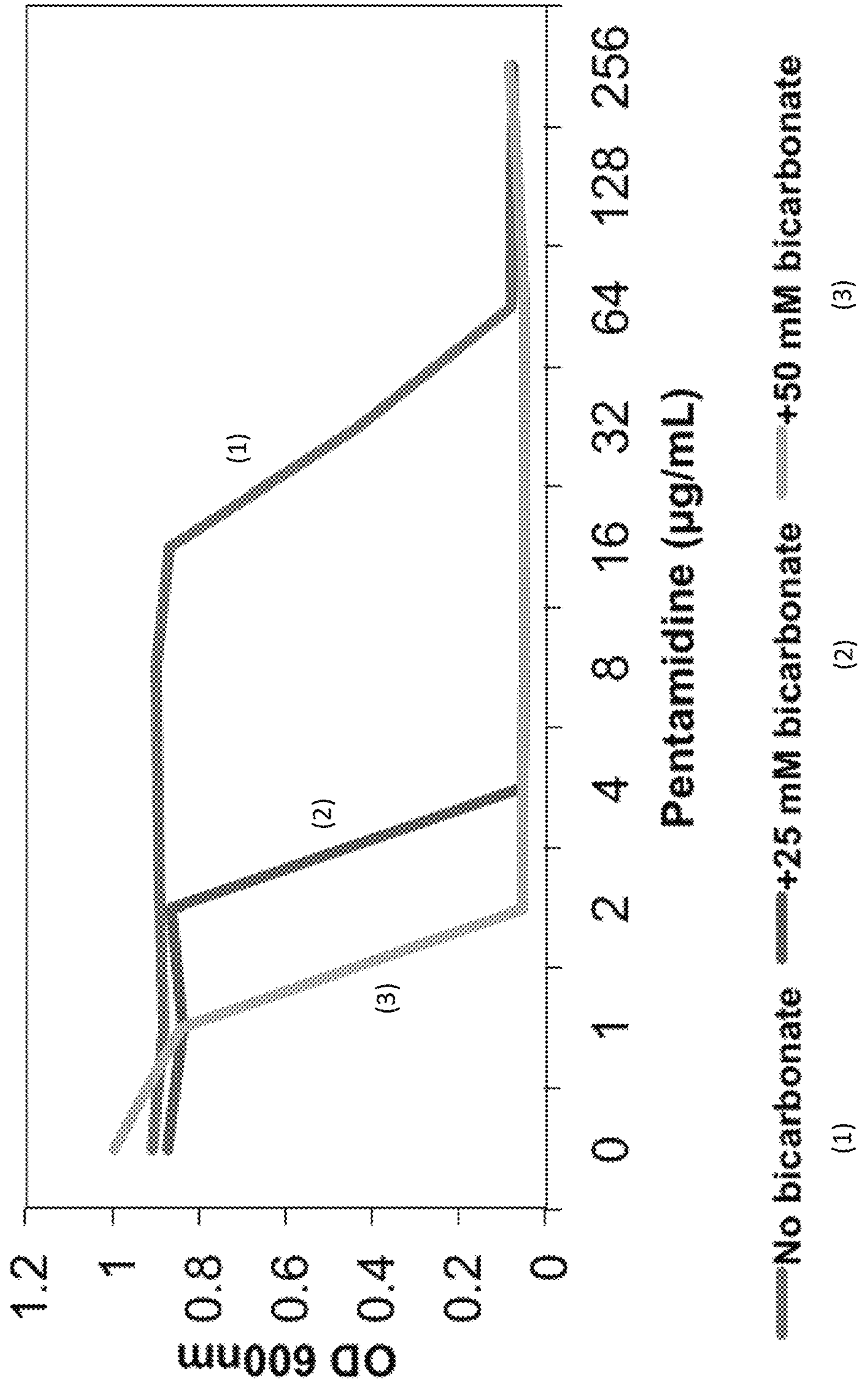
FIG. 9 shows a graph showing that the MIC of pentamidine used against Saccharomyces cerevisiae is reduced from 256 μg/mL to 4 μg/mL in the presence of 25 mM sodium bicarbonate and to 2 μg/mL in the presence of 50 mM sodium bicarbonate in an illustrative embodiment of the invention.

An overnight culture of Saccharomyces cerevisiae was diluted 1:5,000 into fresh YPD medium, supplemented with 0, 25 mM or 50 mM sodium bicarbonate and tested against two-fold serial dilutions of pentamidine. Plates were incubated 24 hours and optical density read at 600 nm FIG. 9 shows that the MIC of pentamidine is reduced from 256 μg/mL to 4 μg/mL in the presence of 25 mM sodium bicarbonate and to 2 μg/mL in the presence of 50 mM sodium bicarbonate.

Example 12: Physiological Concentrations of Bicarbonate Enhance the Antibacterial Activity of Various Chemical Factors Involved in Innate Immunity The influence of sodium bicarbonate (pH 7.4) on the in vitro antibacterial activity of various secretory molecules and cellular components that make up innate immunity against bacterial pathogens was investigated. Specifically, the ability of sodium bicarbonate, at the sub-MIC but physiological concentration of 25 mM, to potentiate the activity of various mediators of host defense, including defensins and cathelicidins, whose family members make up the principal components of innate immunity in vertebrates (Zasloff, M. N Engl J Med 2002, 347: 1199-1200), was assessed.

Sodium bicarbonate itself exhibited antibacterial activity against *E. coli, Staphylococcus aureus*, and other clinically relevant pathogens, with minimum inhibitory concentration (MIC) values ranging from 50-100 mM (Table 6).

TABLE 6

MIC of sodium bicarbonate against various pathogens.

| Organism | MIC (mM) |
|---|---|
| *Escherichia coli* | 100 |
| *Staphylococcus aureus* | 50-100 |
| *Klebsiella pneumoniae* | 100 |
| *Acinetobacter baumannii* | 50 |
| *Pseudomonas aeruginosa* | >100 |
| *Enterococcus faecium* | 50-100 |

Figure 10:
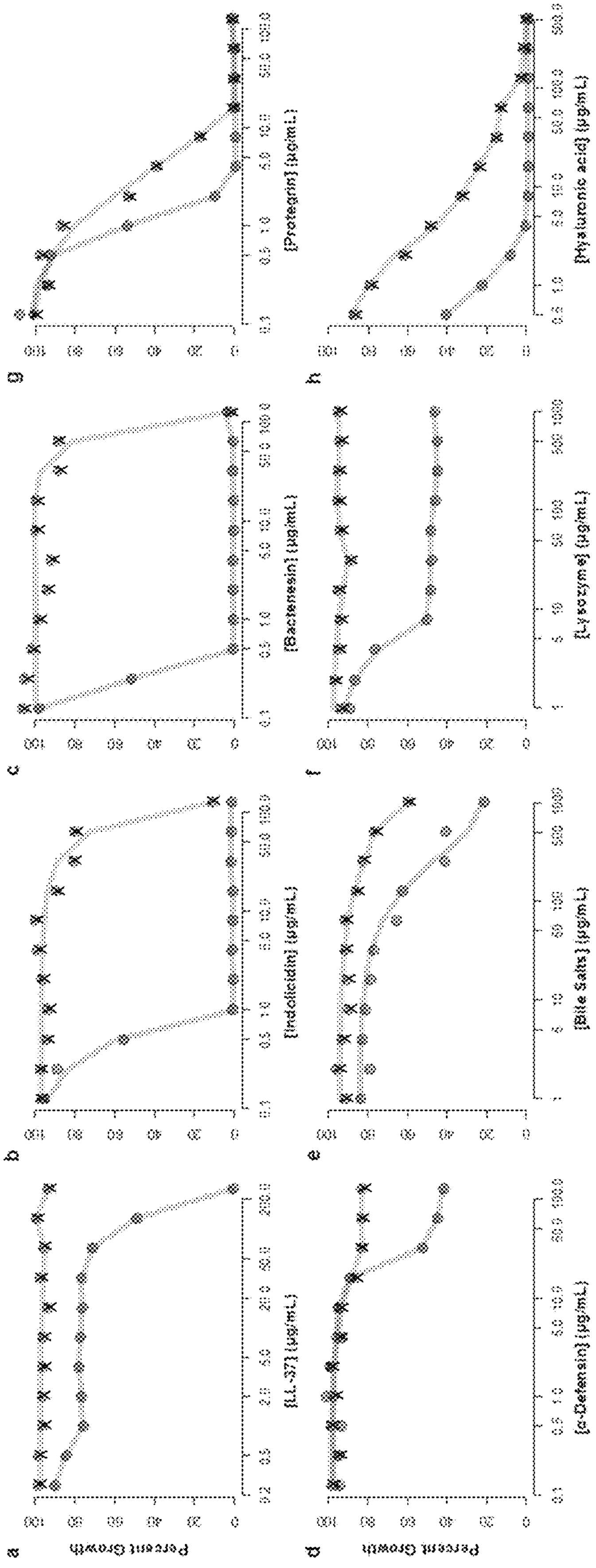
FIG. 10 shows that physiological concentrations of bicarbonate enhance the antibacterial activity of various chemical factors involved in innate immunity. Shown are potency analyses of various components against *E. coli* in MHB (line with Xs) and MHB supplemented with 25 mM sodium bicarbonate (line with circles) for a, LL-37; b, indolicidin; c, bactenesin; d, alpha-defensin; e, bile salts; f, lysozyme; g, protegrin; and h, hyaluronic acid.

Shown in FIG. 10, Panels a-e are potency analyses of various components against *E. coli* in MHB (line with Xs) and MEM supplemented with 25 mM sodium bicarbonate (line with circles) for a, LL-37; b, indolicidin; c, bactenesin; d, alpha-defensin; e, bile salts; f, lysozyme; g, protegrin; and h, hyaluronic acid. Averages of triplicate experiments are shown.

The antimicrobial activity of alpha-defensin and LL-37 were enhanced on average 4 to 8-fold against *E. coli* (FIG. 10, Panels a,e) and *S. aureus* (Table 7). Other antimicrobial peptides, such as indolicidin and bactenesin, were also potentiated in the presence of bicarbonate, 128- and 256-fold, respectively against *E. coli* (FIG. 10, Panels b,c), and 16- and 256-fold, respectively against *S. aureus* (Table 7). Also enhanced in the presence of bicarbonate, was the activity of the porcrine leukocyte protegrin (8-fold in both *E. coli* and *S. aureus*) (FIG. 10, Panel d; Table 7). Additionally, a physiological concentration of sodium bicarbonate enhanced the inhibitory activity of other innate immunity chemical factors such as lysozyme and bile salts against *E. coli* (FIG. 1, Panels f,g). The innate immunity chemical barrier, hyaluronic acid, which is ubiquitously expressed in the extracellular matrix of all vertebrate tissues was also potentiated in the presence of sodium bicarbonate, 64-fold in both *E. coli* and *S. aureus* (FIG. 10, Panel h; Table 7). It is noted that common among these components of innate immunity is their ultimate action on the cytoplasmic membrane causing membrane depolarization.

TABLE 7

MIC of various components of innate immunity in MHB vs MHB + 25 mM sodium bicarbonate against *S. aureus* (strain Newman)

| Component | MIC (μg/mL) in MHB | MIC (μg/mL) in MHB + 25 mM bicarbonate |
|---|---|---|
| LL-37 | 128 | 32 |
| Indolicidin | 128 | 8 |
| Bactenesin | 128 | 0.5 |
| α-defensin | ND* | ND* |
| Protegrin | 32 | 4 |
| Lysozyme | >256 ** | >256 ** |
| Bile salts | 512 | 512 |
| Hyaluronic acid | 4 | 0.0625 |

*ND: not determined; ***S. aureus* is intrinsically resistant to lysozyme

Example 13: The Effects of Proton Motive Force (PMF) Perturbations on the Activity of Antibiotics The proton motive force (PMF) describes the electrochemical potential at the cytoplasmic membrane that is composed of an electrical potential (Δψ, negative inside) and a proton gradient (ΔpH, acidic outside). It is known that tetracyclines penetrate bacterial cells in a ΔpH-dependent manner, while positively charged aminoglycosides utilize the Δψ component for transport. Agents that selectively perturb either Δψ or ΔpH are known to prompt a compensatory increase in the other component in order to maintain PMF. The role of bicarbonate in perturbing PMF of bacteria was further assessed.

Figure 12:
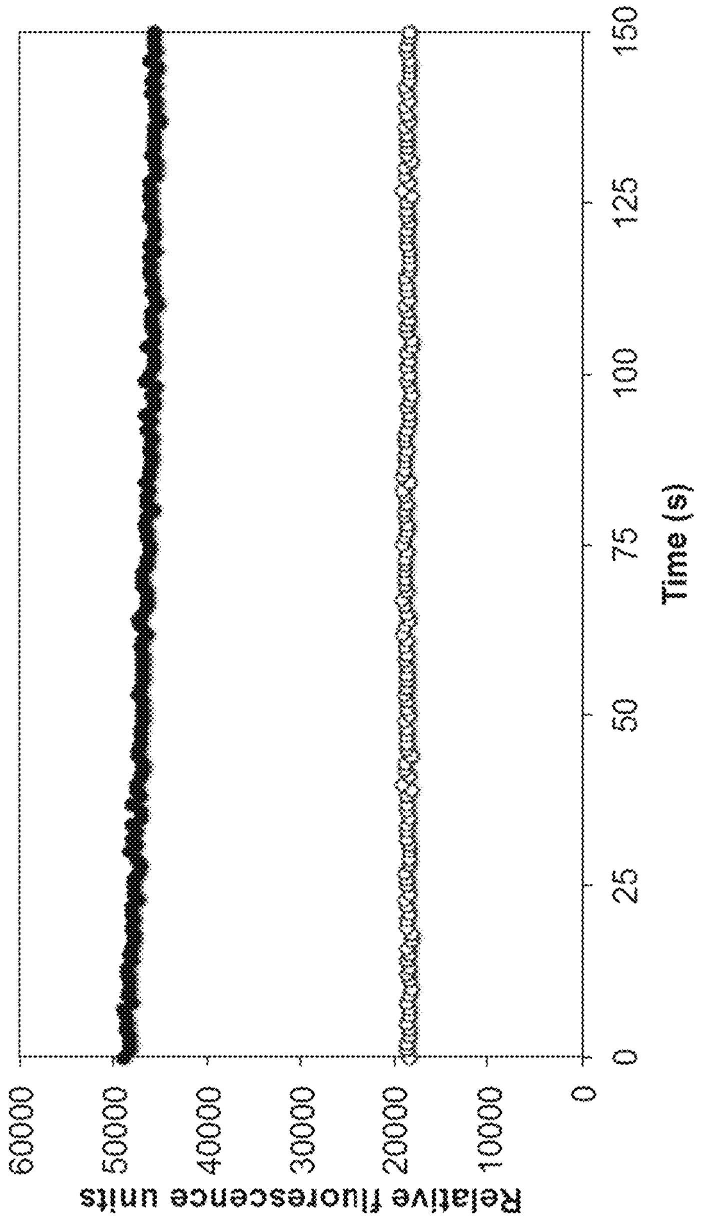
FIG. 12 shows uptake of 3,3'-Dipropylthiacarbocyanine iodide, a membrane-potential sensitive dye, in *S. aureus* cells in the absence (untreated, white circles) or presence of 25 mM sodium bicarbonate (treated, black circles).

Treatment of *E. coli* with 25 mM bicarbonate led to a higher transmembrane distribution of 3,3'-dipropylthiadicarbocyanine iodide ($DiSC_3(5)$), a fluorescent probe that exhibits Δψ-dependent membrane accumulation (FIG. 12). Without being bound to theory, this is consistent that with the observed increase in aminoglycoside activity, selective dissipation of ΔpH by sodium bicarbonate is compensated for by an increase in Δψ that in turn drives uptake of aminoglycosides.

Specifically, FIG. 12 shows uptake of 3,3'-Dipropylthiacarbocyanine iodide, a membrane-potential sensitive dye. *S. aureus* cells were grown to exponential phase in the absence (untreated) or presence of 25 mM sodium bicarbonate (treated), washed and loaded with 1 μM $DiSC_3(5)$. *S. aureus* treated with 25 mM sodium bicarbonate exhibited an increased uptake in the levels of $DiSC_3(5)$ as measured by fluorescence (black circles) and compared to uptake levels of untreated cells (white circles). Uptake and fluorescence was stable over time as shown in the graph.

Pre-incubation of *E. coli* with the proton ionophore, carbonyl cyanide m-chlorophenyl hydrazone (CCCP; selectively targets the pH gradient of cells), prior to treatment with sodium bicarbonate and gentamicin, reversed the potentiation observed (FIG. 11, Panel b). Panel b shows that pre-treatment with CCCP abolishes the potentiation of gentamicin by sodium bicarbonate. Shown are potency analyses of gentamicin in MHB against *E. coli* (1); MHB supplemented with 25 mM sodium bicarbonate (2); CCCP pre-treated cells in MHB (3); CCCP pre-treated cells in MHB supplemented with 25 mM sodium bicarbonate (4). Averages of triplicate experiments are shown.

Taken together, these data show that sodium bicarbonate influences the entry of antibacterial agents that are driven by PMF, suppressing those that require an intact pH gradient across the cytoplasmic membrane, and enhancing those that are driven by Δψ, such as the polycationic aminoglycosides.

Example 14: Effects of Bicarbonate on Bacterial Cellular Respiration in the Context of Antibiotics Other antibiotics that rely on cellular energetics for entry include fosfomycin and novobiocin. Fosfomycin is actively transported via a glycerol-3-phosphate permease where transport activity has been shown to be dependent on ΔpH. Uptake of novobiocin is similarly an active transport mechanism supported by ΔpH such that uncouplers and inhibitors of respiration have been shown to reduce its cellular accumulation. Sodium bicarbonate suppressed the activity of fosfomycin and novobiocin (FIG. 6C).

Figure 13:
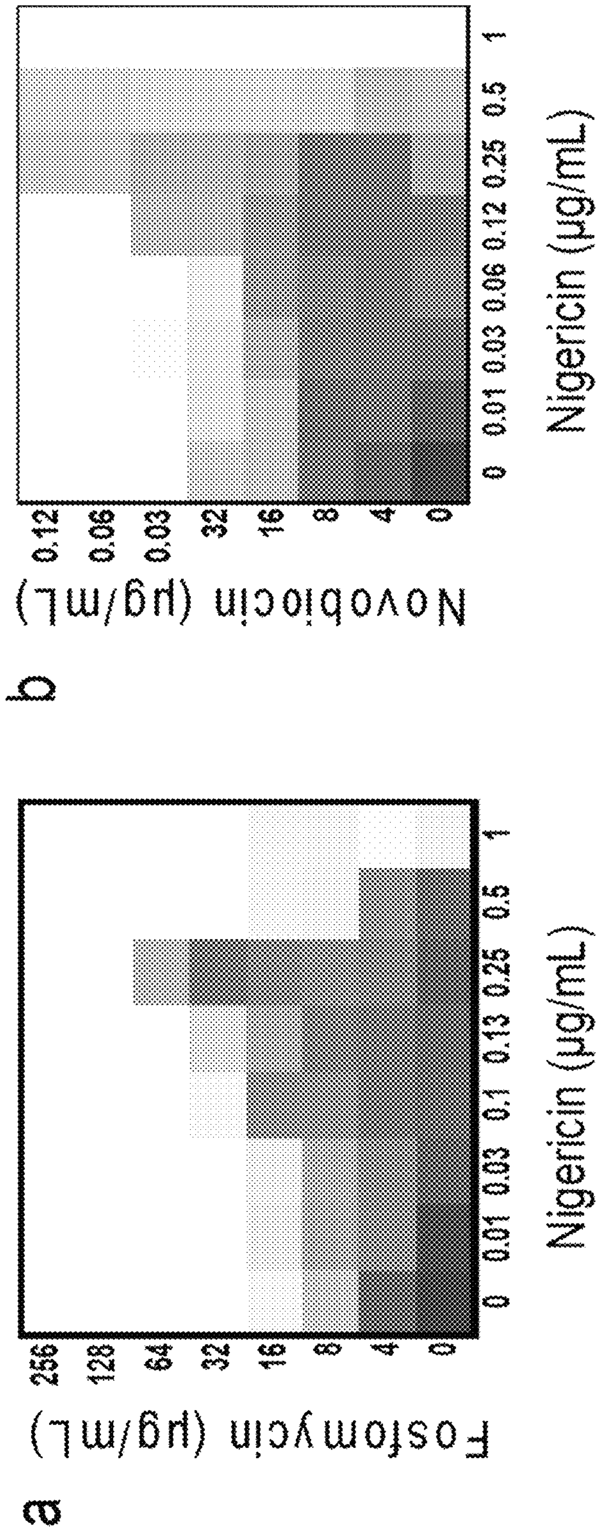
FIG. 13 shows that a combination of nigericin, a protonophore, with fosfomycin (Panel a) or novobiocin (Panel b) leads to antagonistic interactions against *S. aureus*. Shown are microdilution checkerboard analyses, where the extent of inhibition is shown as a heat plot, such that the darkest color represents full bacterial growth.

Nigericin, an ionophore that selectively dissipates the pH gradient, also suppressed the activity of fosfomycin and novobiocin (FIG. 13, Panels a-b). Specifically, FIG. 13, Panel a and FIG. 13, Panel b show that a combination of nigericin, a protonophore, with fosfomycin (Panel a) or novobiocin (Panel b) leads to antagonistic interactions against *S. aureus* (sensitive to nigericin). Shown are microdilution checkerboard analyses, where the extent of inhibition is shown as a heat plot, such that the darkest color represents full bacterial growth.

Fluoroquinolone (FQ) antibiotics show a variety of responses in the presence of 25 mM sodium bicarbonate depending on their physicochemical properties and the organism in question. While convention holds that FQ uptake is a passive process, previous studies have noted that the addition of the protonophore CCCP results in increased uptake of some FQs, suggesting a role for the Δψ component of the proton motive force (Piddock, L. J., Jin, Y. F., Ricci, V. & Asuquo, A. E. Quinolone accumulation by *Pseudomonas aeruginosa, Staphylococcus aureus* and *Escherichia coli*. J Antimicrob Chemother 43, 61-70 (1999); and Diver, J. M., Piddock, L. J. & Wise, R. The accumulation of five quinolone antibacterial agents by *Escherichia coli*. J Antimicrob Chemother 319-333 (1990)). Consistent with this, a potentiation of various FQs by bicarbonate was observed. The activity of FQs in the presence of bicarbonate against *E. coli* correlated with the nature of the substituents at the C-7 position of the quinolone nucleus (Table 8). The activities of FQs containing more basic substituents at C-7 (e.g. ciprofloxacin and besifloxacin) increased in the presence of bicarbonate, while those with more acidic substituents (e.g. nalidixic acid and pefloxacin) were suppressed (FIG. 6B, Table 8). These results indicate that the electrochemical component (Δψ) of the proton motive force has a role in FQ uptake. Compensatory increases in Δψ associated with dissipation of ΔpH by bicarbonate would favor the uptake of positively charged species. In *S. aureus*, however, there was no enhancement by bicarbonate of FQs; instead, a small suppression was observed for the antibacterial activity of this chemical class.

TABLE 8

Structural formula and physicochemical properties of fluoroquinolones. Listed are the pKa values for the acidic and basic functions of the fluoroquinolones, generated from ChemAxon, a physico-chemical property predictor.

| | Structure | pKa (Strongest Acidic) | pKa (Strongest Basic) |
|---|---|---|---|
| Besifloxacin | 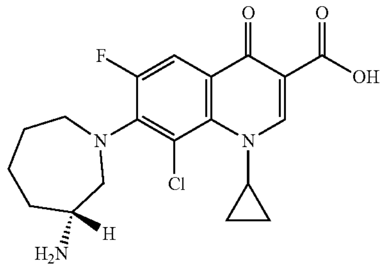 [SMILES: N[C@@H]1CCCCN(c2c(F)cc3c(=O)c(C(=O)O)cn(C4CC4)c3c2Cl)C1] | 5.64 | 9.67 |
| Ciprofloxacin | 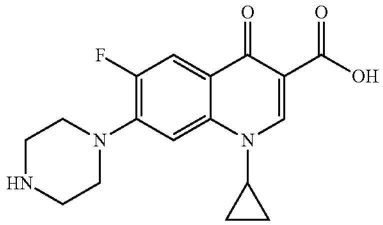 [SMILES: O=C(O)c1cn(C2CC2)c2cc(N3CCNCC3)c(F)cc2c1=O] | 5.76 | 8.68 |
| Enoxacin | 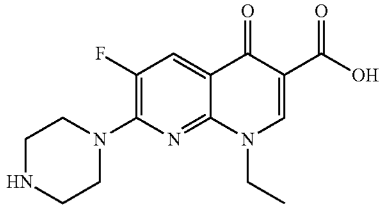 [SMILES: CCn1cc(C(=O)O)c(=O)c2cc(F)c(N3CCNCC3)nc21] | 5.5 | 8.59 |
| Levofloxacin | 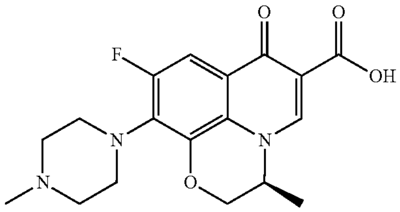 [SMILES: C[C@H]1COc2c(N3CCN(C)CC3)c(F)cc3c(=O)c(C(=O)O)cn1c23] | 5.45 | 6.2 |
| Moxifloxacin | 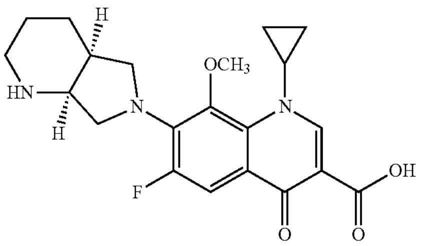 [SMILES: COc1c(N2C[C@@H]3CCCN[C@@H]3C2)c(F)cc2c(=O)c(C(=O)O)cn(C3CC3)c12] | 5.69 | 9.42 |
| Nalidixic acid | 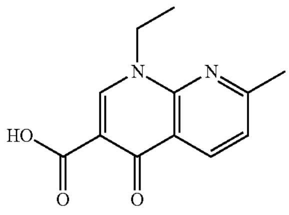 [SMILES: CCn1cc(C(=O)O)c(=O)c2ccc(C)nc21] | 5.95 | 4.68 |

TABLE 8-continued

Structural formula and physicochemical properties of fluoroquinolones. Listed are the pKa values for the acidic and basic functions of the fluoroquinolones, generated from ChemAxon, a physico-chemical property predictor.

| | Structure | pKa (Strongest Acidic) | pKa (Strongest Basic) |
|---|---|---|---|
| Norfloxacin | 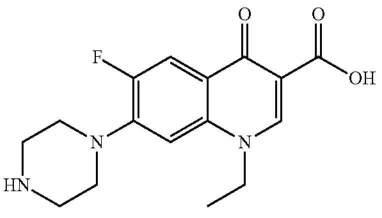 [SMILES: CCn1cc(C(=O)O)c(=O)c2cc(F)c(N3CCNCC3)cc21] | 5.77 | 8.68 |
| Pefloxacin | 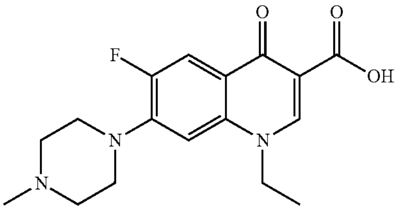 [SMILES: CCn1cc(C(=O)O)c(=O)c2cc(F)c(N3CCN(C)CC3)cc21] | 5.66 | 6.47 |

It is noted that antibiotic uptake is a complex function of permeability and efflux. The impact of bicarbonate on the pH gradient likely also impacts drug efflux, particularly in Gram-negative bacteria. Many multidrug efflux pumps depend on the PMF, where energy from the proton gradient is harnessed to expel drugs from the cell, such as the Resistance-Nodulation-Division (RND)-system AcrAB-TolC in *E. coli*. It was assessed whether consistent with a role in dissipating ΔpH, bicarbonate would reduce efflux activity. The potentiation of dirithromycin, for example, by bicarbonate was lost in a strain lacking the outer membrane channel of this tripartite efflux system (ΔtolC) (FIG. 11, Panel c), indicating it was inhibition of efflux by sodium bicarbonate that led to its enhanced activity. Although macrolide antibiotics are thought to be of little value for the treatment of Gram-negative bacteria due to their diminished accumulation these studies show that in the bicarbonate-rich environment of the host, energy-depended efflux systems may be less effective than predicted by conventional in vitro MIC determinations. Panel c shows that lack of the outer membrane tripartite pump, tolC, causes a loss of potentiation of sodium bicarbonate towards dirithromycin in *E. coli*. Shown are potency analyses of dirithromycin against: wild-type *E. coli* in MEM (1); wild-type *E. coli* in MHB supplemented with 25 mM sodium bicarbonate (2); ΔtolC in MEM (3); ΔtolC in MHB supplemented with 25 mM sodium bicarbonate (4). Averages of triplicate experiments are shown.

Figure 14:
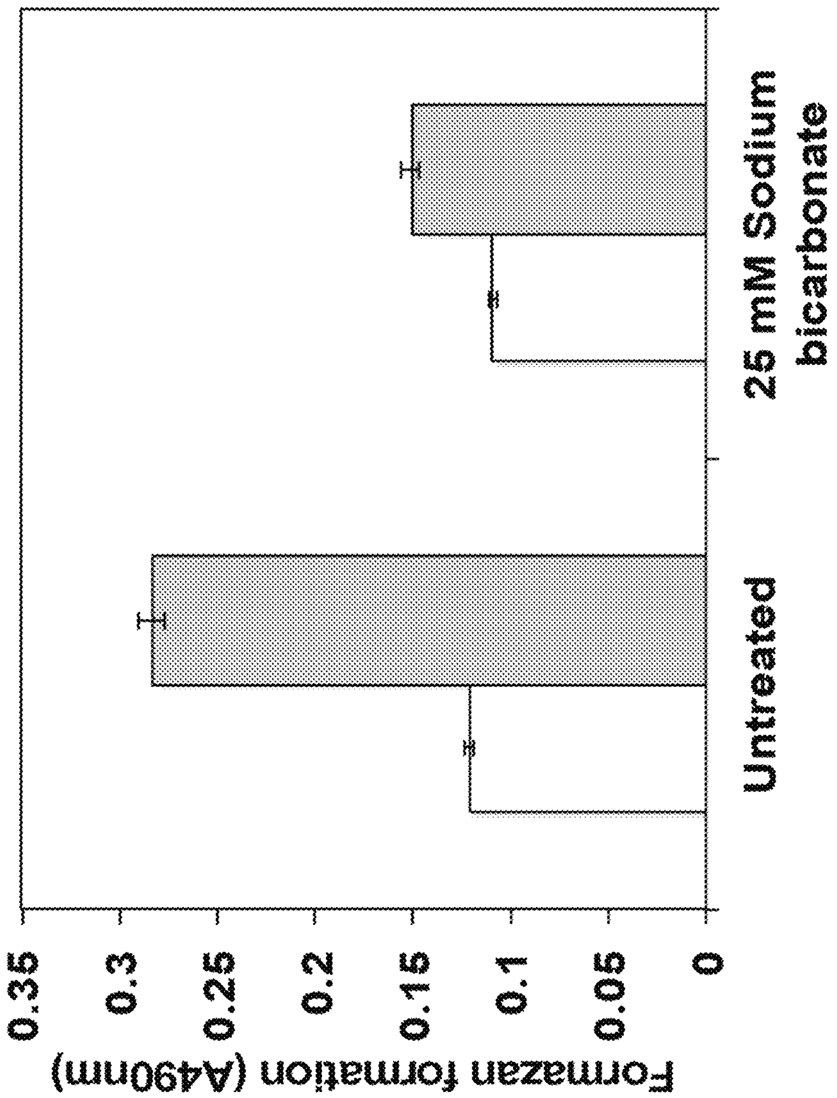
FIG. 14 shows that sodium bicarbonate inhibits cellular respiration in *E. coli.*

Inhibition of cell wall synthesis was attenuated in the presence of sodium bicarbonate in *E. coli* only 2-4 fold on average, but this suppression was more pronounced in *S. aureus*, which is generally more susceptible to cell wall synthesis inhibitors than Gram-negative bacteria. Where cell wall-active compounds are most effective on actively dividing bacteria, suppression of the action of the cidal antibiotics, β-lactams and cephalosporins, for example, may be due to reduced respiratory energy production to fuel growth in the presence of PMF-altering concentrations of bicarbonate (Lobritz, M. A. et al. Antibiotic efficacy is linked to bacterial cellular respiration. *Proc Natl Acad Sci USA* 112, 8173-8180, doi:10.1073/pnas.1509743112 (2015)). Accordingly, a significant effect on cellular respiration (70% reduction) in *E. coli* was observed, when treated with 25 mM sodium bicarbonate (FIG. 14). Specifically shown in FIG. 14 is the effect of 25 mM sodium bicarbonate on the reduction of 2-(p-iodophenyl)-3-(p-nitrophenyl)-5-phenyl tetrazolium chloride (INT) to INT-formazan. Open bars indicate the formation of formazan at t=0 as read at 490 nm. Grey bars represent the formation of formazan following 60 min incubation.

Figure 15:
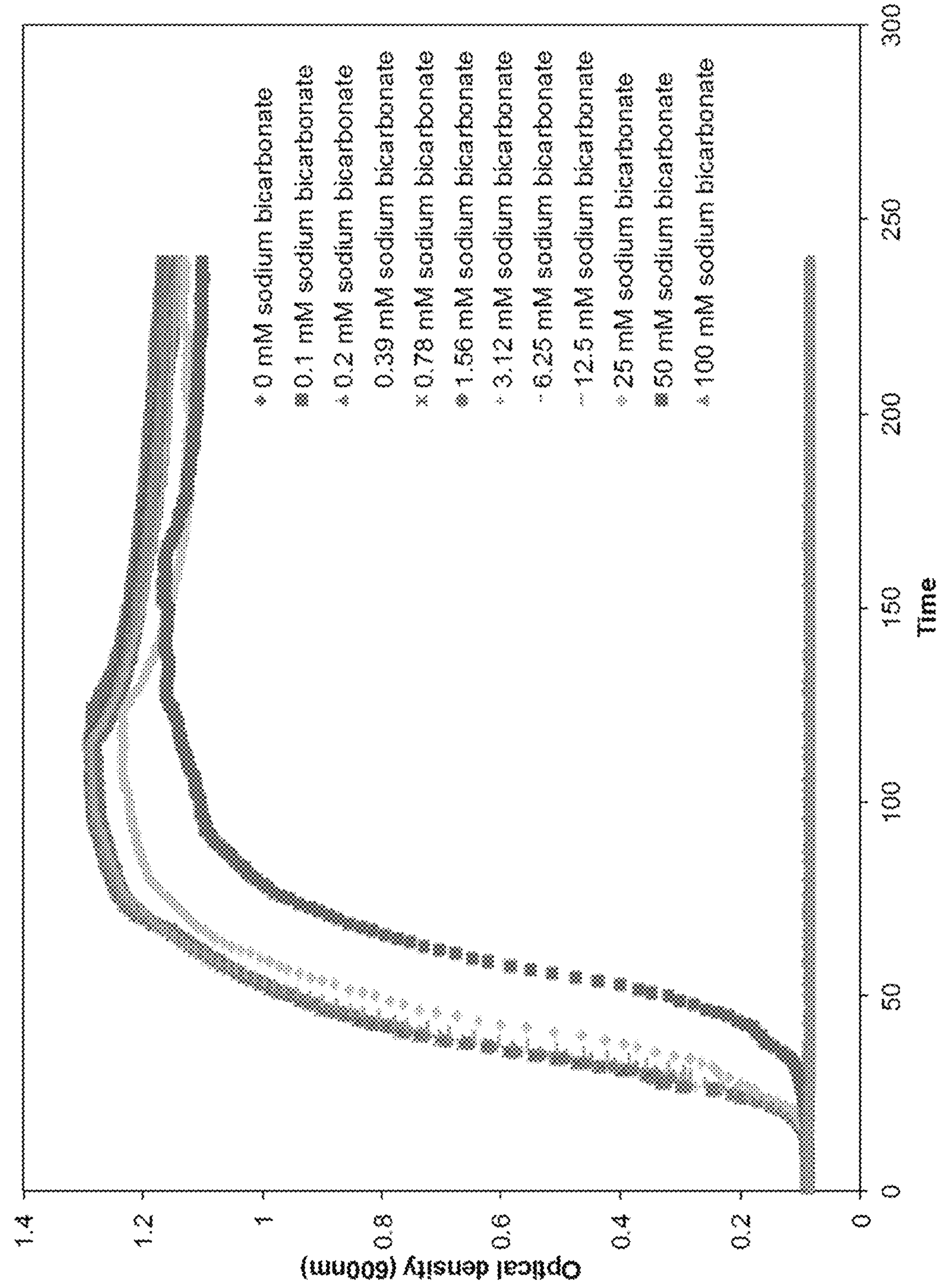
FIG. 15 shows the growth curve of *E. coli* grown in the presence of varying concentrations of sodium bicarbonate.

Consistent with this finding, *E. coli* grown in high concentrations of sodium bicarbonate exhibited a delayed lag phase, indicating lowered metabolic resources (FIG. 15). FIG. 15 shows the growth curve of *E. coli* grown in the presence of varying concentrations of sodium bicarbonate. Growth curve measurements were performed in a microtiter plate and optical density read every 10 mins in a Tecan infinite M1000 Pro with shaking intervals before readings.

Figure 16:
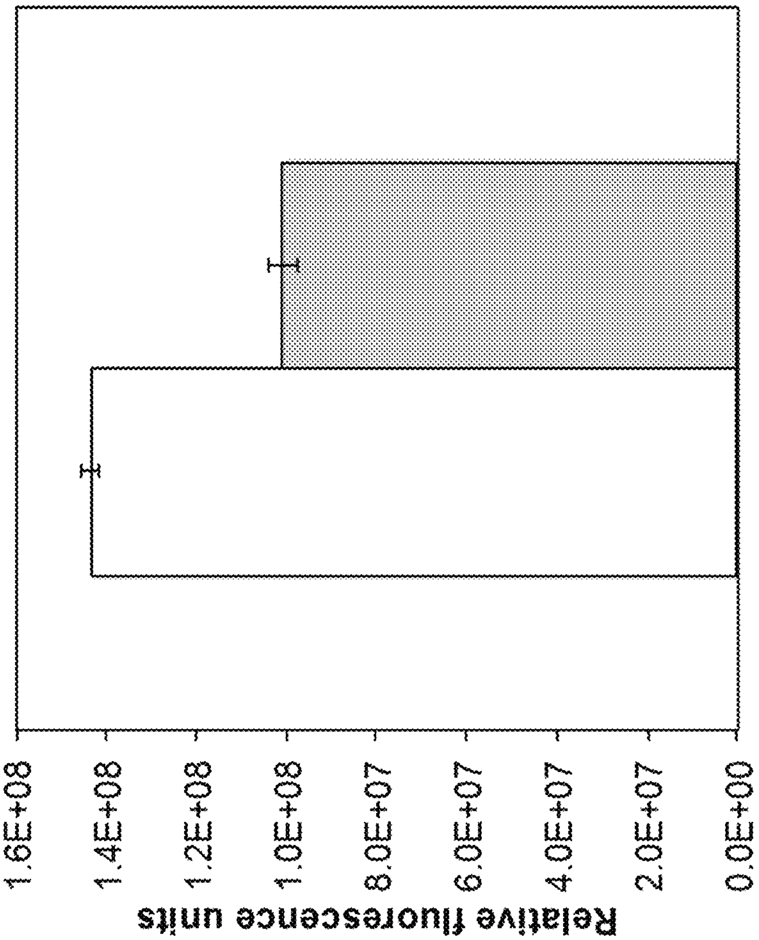
FIG. 16 shows the effect of 25 mM sodium bicarbonate on intracellular ATP levels, measured by a luciferin-luciferase bioluminescence assay.

Further, intracellular ATP levels, which are produced via the $F_0F_1$-ATPase utilizing PMF, were reduced by ~30% in sodium bicarbonate-treated *E. coli* compared to the untreated control (FIG. 16). FIG. 16 shows the effect of 25 mM sodium bicarbonate on intracellular ATP levels, measured by a luciferin-luciferase bioluminescence assay. Shown is the relative fluorescence units for untreated *S. aureus* cells (white bar) and for 25 mM bicarbonate treated *S. aureus* cells (grey).

Overall, these experiments indicate that bicarbonate is a bacteriostatic compound that perturbs cellular respiration and reduces the activity of bactericidal antibiotics that require actively growing bacteria for activity.

Figure 17:
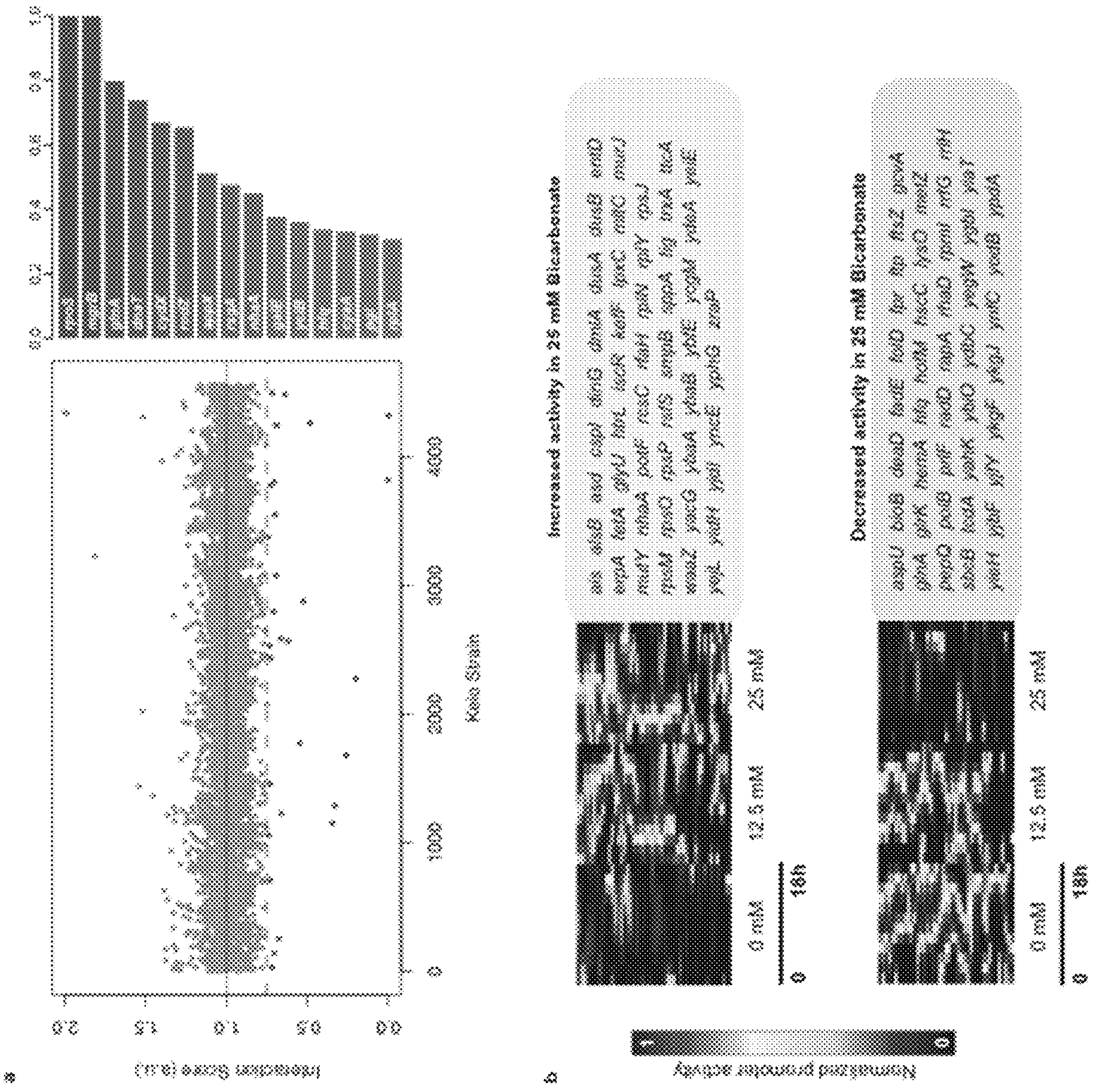
FIG. 17, Panels a-b show the chemical-genomic interactions with 25 mM bicarbonate in *E. coli* K12.

Example 15: Effects of Gene Deletions in *E. coli* on the Ability of Bicarbonate to Reduce Growth The mode of action of bicarbonate on *E. coli* physiology was further investigated. The impact of 25 mM sodium bicarbonate on an ordered *E. coli* gene-deletion collection of ~4,000 strains was assessed. Sodium bicarbonate reduced the growth of 28 deletion strains. The missing genes encoded proteins involved in redox reactions and oxidative stress responses (FIG. 17, Panel a, Table 9). Among them was dsbB, whose gene product is required to maintain disulfide bonds in periplasmic enzymes at extreme pHs, and the gene encoding the sigma factor RpoS that regulates several components of resistance to both acid and base. Deletion in the gene cydX, coding for a cytochrome oxidase, caused sensitization to bicarbonate. Deletion in the gene nhaA, which encodes a $Na^+$:$H^+$ antiporter that has a major role in sodium ion and alkaline pH homeostasis in *E. coli* and many enterobacteria, sensitized cells to bicarbonate. It was observed that a defect in proton expulsion enhanced the growth inhibition by bicarbonate. Deletion of cya was also sensitized to bicarbonate. Overall, it was observed that gene deletions sensitized to bicarbonate involved pH-related processes, through proton expulsion or stress responses, that when deleted amplify bicarbonate's action on the pH gradient across the inner membrane.

FIG. 17, Panel a: Keio collection was exposed to 25 mM bicarbonate for 15 hours at 37° C., and sick/lethal interactions were assessed using a multiplicative approach (French, S. et al. A robust platform for chemical genomics in bacterial systems. *Mol Biol Cell* 27, 1015-1025, doi:10.1091/mbc.E15-08-0573 (2016)). Shown alongside an index plot of the chemical-genetic interactions are the 15 mutations that most strongly enhanced the activity of bicarbonate (displayed as 1-interaction score).

TABLE 9

Genetic enhancers (Keio collection) of growth inhibition by 25 mM bicarbonate. Strains were exposed to bicarbonate for 15 hours in cation-adjusted MHB broth, and a multiplicative approach was used to determine the sick or lethal effects on each strain. Shown here are the outliers from FIG. 17, Panel a, alongside their gene products, as annotated from EcoCyc[5].

| Deletion strain | Gene description |
|---|---|
| appX | small outer membrane protein |
| cyaA | adenylate cyclase |
| cydX | cytochrome bd I terminal oxidase - CydX subunit |
| degP | serine protease Do |
| dnaT | primosomal protein DnaT |
| dsbB | protein disulfide oxidoreductase |
| envC | EnvC divisome associated factor, activator of peptidoglycan hydrolases |
| fur | Fur transcriptional dual regulator |
| galE | UDP-glucose 4-epimerase |
| glnA | adenylyl-[glutamine synthetase], glutamine synthetase |
| hfq | RNA-binding protein that affects many cellular processes; homolog of mammalian Sm/Sm-like proteins |
| lpoB | outer membrane lipoprotein - activator of MrcB activity |
| mgrB | negative feedback regulator of the PhoQP system |
| nhaA | $Na^+$:$H^+$ antiporter NhaA |
| pgi | phosphoglucose isomerase |
| recB | RecB |
| rodZ | transmembrane component of cytoskeleton |
| rplA | 50S ribosomal subunit protein L1 |
| rpmF | 50S ribosomal subunit protein L32 |
| rpoS | RNA polymerase, sigma S (sigma 38) factor |
| rpsT | 30S ribosomal subunit protein S20 |
| rsgA | ribosome small subunit-dependent GTPase A |
| sapA | periplasmic binding protein SapA of predicted ABC transporter |
| treA | periplasmic trehalase |
| ubiF | 2-octaprenyl-3-methyl-6-methoxy-1,4-benzoquinone hydroxylase |
| ubiH | 2-octaprenyl-6-methoxyphenol hydroxylase |
| ybbY | putative transport protein, nucleobase:cation symporter-2 (NCS2) family |
| ybcO | DLP12 prophage; predicted protein |
| yciB | inner membrane protein |

Example 16: Adaptive Strategies by *E. coli* in Response to Sodium Bicarbonate

The action of sodium bicarbonate on *E. coli* was further assessed by analyzing promoter activity in response to 25 mM sodium bicarbonate using a genome-scale, promoter-reporter library where nearly all of the promoters in *E. coli* have been transcriptionally fused to gfp (FIG. 17, Panel b, Table 10).

Shown in FIG. 17, Panel b are the responses of a genome-scale GFP promoter library (Zaslaver, A. et al. A comprehensive library of fluorescent transcriptional reporters for *Escherichia coli. Nat Methods* 3, 623-628, doi:10.1038/nmeth895 (2006)), to 25 mM bicarbonate. Highlighted are promoters with increased and decreased expression. Of note are the genes nhaA and hfq, that were strong enhancers of growth inhibition by bicarbonate and were differentially expressed in bicarbonate containing medium.

TABLE 10

List of promoters from the GFP promoter-fusion library that demonstrated increased or decreased promoter activity in the presence of 25 mM bicarbonate. Activity was assessed using the pipeline of Zaslaver et al[2]. Shown here are the promoters from FIG. 17, Panel b, alongside their gene products, as annotated from EcoCyc[5].

| Name | Product |
|---|---|
| | Increased promoter activity |
| ais | Predicted lipopolysaccharide core heptose(II)-phosphate phosphatase |
| alsB | D-allose ABC transporter - periplasmic binding protein |
| asd | Aspartate semialdehyde dehydrogenase |
| cspI | Qin prophage; cold shock protein |
| dinG | ATP-dependent helicase |
| dmlA | D-malate/3-isopropylmalate dehydrogenase (decarboxylating) |
| dusA | tRNA-dihydrouridine synthase A |
| dusB | tRNA-dihydrouridine synthase B |
| entD | Phosphopantetheinyl transferase |
| erpA | Essential respiratory protein A |
| fetA | ABC transporter with a role in iron homeostasis - ATP-binding subunit |
| glyU | tRNA-glyU |
| htrL | Involved in lipopolysaccharide biosynthesis |
| iscR | IscR DNA-binding transcriptional dual regulator |
| kefF | Regulator of KefC-mediated potassium transport and quinone oxidoreductase |
| lpxC | UDP-3-O-acyl-N-acetylglucosamine deacetylase |
| mltC | Membrane-bound lytic murein transglycosylase C |
| murJ | Lipid II flippase |
| mutY | Adenine glycosylase; G.C --> T.A transversions |
| nhaA | Na+:H+ antiporter NhaA |
| potF | Putrescine ABC transporter - periplasmic binding protein |
| rcsC | RcsC sensory histidine kinase - asp875 phosphorylated |
| rfaH | RfaH transcriptional antiterminator |
| rplN | 50S ribosomal subunit protein L14 |
| rplY | 50S ribosomal subunit protein L25 |
| rpsJ | 30S ribosomal subunit protein S10 |
| rpsM | 30S ribosomal subunit protein S13 |
| rpsO | 30S ribosomal subunit protein S15 |
| rpsP | 30S ribosomal subunit protein S16 |
| rsfS | Ribosomal silencing factor |
| smpB | Small protein B |
| sppA | Protease IV, a signal peptide peptidase |
| tig | Chaperone protein Tig; trigger factor |
| trxA | Oxidized thioredoxin, thioredoxin 1 |
| ttcA | tRNA C32 thiolase |
| waaZ | Protein involved in KdoIII attachment during lipopolysaccharide core biosynthesis |
| yacG | DNA gyrase inhibitor YacG |
| ybaA | Conserved protein |
| ybaB | Conserved DNA-binding protein |
| ybfE | LexA-regulated protein |
| ycgM | Predicted isomerase/hydrolase |
| ydeA | Arabinose exporter |

TABLE 10-continued

List of promoters from the GFP promoter-fusion library that demonstrated increased or decreased promoter activity in the presence of 25 mM bicarbonate. Activity was assessed using the pipeline of Zaslaver et al[2]. Shown here are the promoters from FIG. 17, Panel b, alongside their gene products, as annotated from EcoCyc[5].

| Name | Product |
|---|---|
| yeiE | LYSR-type transcriptional regulator |
| yejL | Conserved protein |
| yidH | Conserved inner membrane protein |
| yjdI | Conserved protein |
| yncE | Conserved protein |
| yphG | Conserved protein |
| zraP | Zinc responsive, periplasmic protein with chaperone activity |
| | Decreased promoter activity |
| aspU | tRNA-aspU |
| bioB | Biotin synthase |
| deaD | DeaD, DEAD-box RNA helicase |
| fadE | Acyl-CoA dehydrogenase |
| folD | Bifunctional 5,10-methylene-tetrahydrofolate dehydrogenase/ 5,10-methylene-tetrahydrofolate cyclohydrolase |
| fpr | Flavodoxin-NADP+ reductase/ferredoxin-NADP+ reductase |
| ftp | Flavin transferase |
| ftsZ | Essential cell division protein FtsZ |
| gcvA | GcvA DNA-binding transcriptional dual regulator |
| glnA | Adenylyl-[glutamine synthetase], glutamine synthetase |
| glrK | GlrK sensory histidine kinase - phosphorylated, GlrK sensory histidine kinase |
| hemA | Glutamyl-tRNA reductase |
| hfq | RNA-binding protein that affects many cellular processes; homolog of mammalian Sm/Sm-like proteins |
| hofM | Protein involved in utilization of DNA as a carbon source |
| hscC | Hsc62, Hsp70 family chaperone, binds to RpoD and inhibits transcription |
| lysO | L-lysine exporter |
| metZ | TRNA-fMet1 |
| pepQ | Xaa-Pro dipeptidase |
| polB | DNA polymerase II |
| prlF | PrlF antitoxin |
| radD | Predicted ATP-dependent helicase; implicated in DNA repair |
| rapA | RNA polymerase-binding ATPase and RNAP recycling factor |
| rhaD | Rhamnulose-1-phosphate aldolase |
| rpmI | 50S ribosomal subunit protein L35 |
| rrfG | rrfG 5S ribosomal RNA |
| rrlH | rrlH 23S ribosomal RNA |
| sbcB | Exonuclease I, 3' --> 5' specific; deoxyribophosphodiesterase |
| tcdA | tRNA threonylcarbamoyladenosine dehydratase |
| yahK | Aldehyde reductase, NADPH-dependent |
| ybiO | Mechanosensitive channel YbiO |
| ydbC | Predicted oxidoreductase, NAD(P)-binding |
| yegW | Predicted DNA-binding transcriptional regulator |
| ygbI | Predicted DNA-binding transcriptional regulator, DEOR-type |
| yiaT | Outer membrane protein YiaT |
| yieH | 6-Phosphogluconate phosphatase |
| yjbF | Predicted lipoprotein |
| yjfY | Putative protein |
| ykgF | Predicted amino acid dehydrogenase with NAD(P)-binding domain and ferridoxin-like domain |
| ykgJ | Predicted ferredoxin |
| ynfC | YnfC lipoprotein |
| yodB | Predicted cytochrome |
| ypdA | YbdA sensory histidine kinase - his371 phosphorylated |

Changes in promoter activity that reflected adaptive strategies by the bacterium to maintain pH homeostasis were observed. Promoter activity for a large number of substrate/proton antiporters was repressed in the presence of bicarbonate. Promoter activity for nhaA was enhanced in the presence of bicarbonate.

Figure 20:
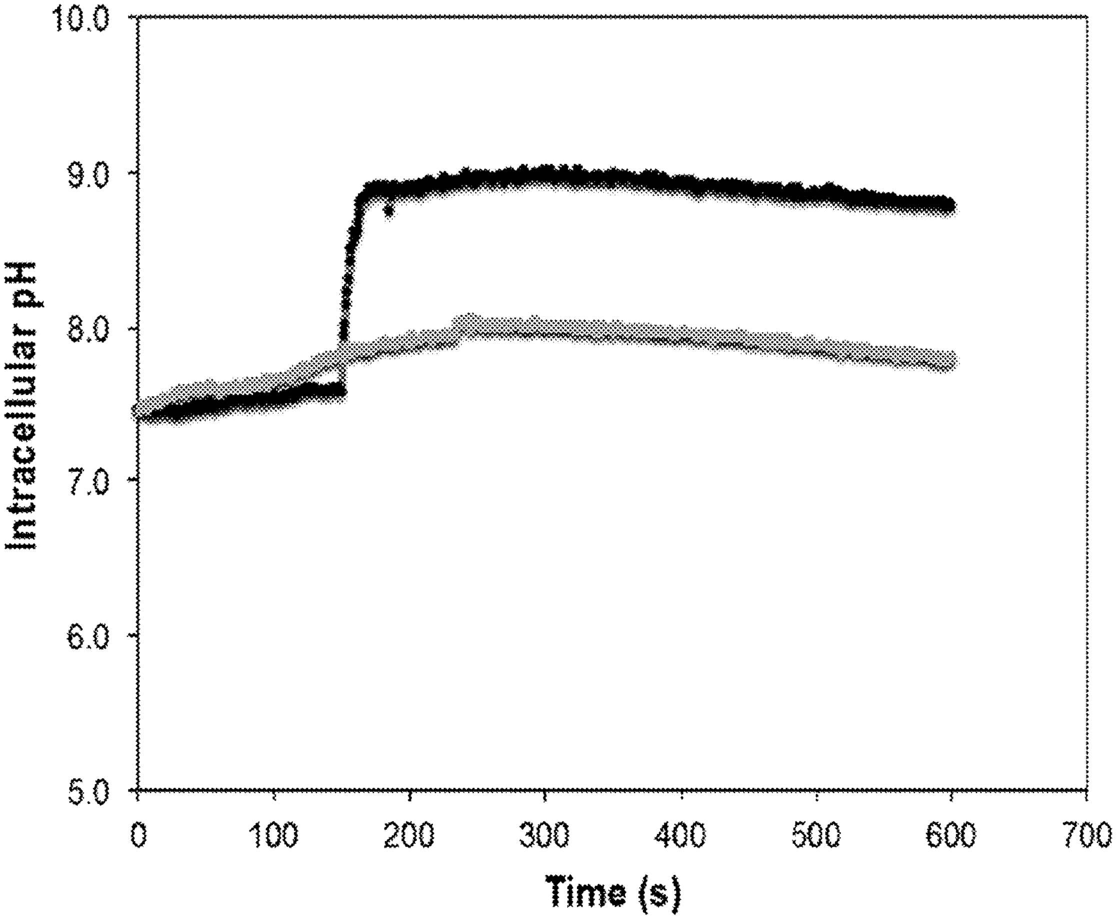
FIG. 20 shows changes in intracellular pH upon treatment with bicarbonate.

Upon treatment with bicarbonate, cytoplasmic pH, which began at ~7.5, endured a rapid cytoplasmic alkalinization, as measured by BCECF-AM (FIG. 20). FIG. 20 shows changes in intracellular pH upon treatment with bicarbonate. *S. aureus* cells were loaded with the pH sensitive dye BCECF-AM and were washed and resuspended in PBS. Following baseline readings, PBS (grey circles) or 25 mM sodium bicarbonate (black circles) were added at the arrow and fluorescence measured over time. A standard curve for intracellular pH calibration was used to calculate intracellular pH.

The expression of a number of inner membrane protein/transporters was differentially regulated in the presence of bicarbonate. Decreased promoter activity was also observed for many ATP-dependent processes, likely as an adaptive effort to conserve energy.

These data indicate that overall, *E. coli* adaptation to bicarbonate involved strategies to respond to periplasmic pH changes, increase membrane potential and preserve energy.

Example 17: The Effect of Bicarbonate on the Activity of Molecules That Selectively Perturb Δψ

It was assessed whether bicarbonate enhances the activity of molecules that selectively perturb Δψ. To test this, the following Δψ dissipaters were combined with sodium bicarbonate: valinomycin, a selective potassium ionophore, as well as compounds that have previously characterized as dissipaters of Δψ, namely I1, I2 and I3 (Farha, M. A., Verschoor, C. P., Bowdish, D. & Brown, E. D. Collapsing the proton motive force to identify synergistic combinations against *Staphylococcus aureus*. *Chemistry & biology* 20, 1168-1178, doi:10.1016/j.chembiol.2013.07.006 (2013)) and loperamide (Ejim, L. et al. Combinations of antibiotics and nonantibiotic drugs enhance antimicrobial efficacy. *Nature chemical biology* 7, 348-350, doi:10.1038/nchembio.559 (2011)).

Figure 18:
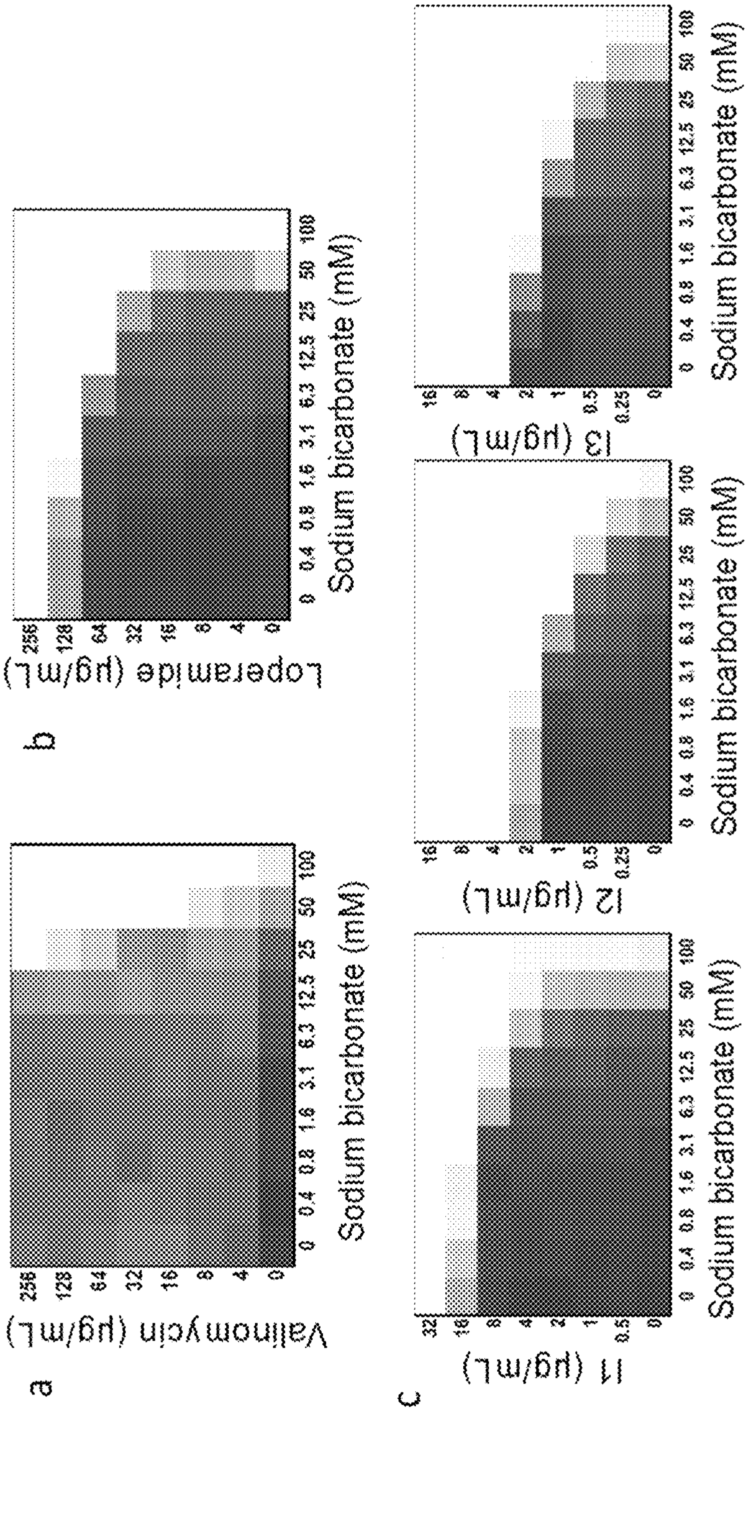
FIG. 18, Panels a-c show microdilution checkerboard analyses for sodium bicarbonate and molecules shown to dissipate $\Delta\Psi$.

All combinations yielded synergistic interactions, consistent with the role of bicarbonate as a selective dissipater of ΔpH (FIG. 18). FIG. 18, Panels a-c show a microdilution checkerboard analyses for sodium bicarbonate and molecules shown to dissipate ΔΨ; Panel a) valinomycin in *S. aureus*; Panel b) loperamide in *E. coli*; and Panel c) molecules 11-3 in *S. aureus*. All checkerboards display synergistic interactions.

This indicates that membrane active agents that target Δψ, while frequently eschewed in drug discovery efforts for potential cytotoxicity, can have superior activity in the bicarbonate-rich environment of the host.

Example 18: The Effect of Bicarbonate is Not an Effect of Changes in pH

Figure 19:
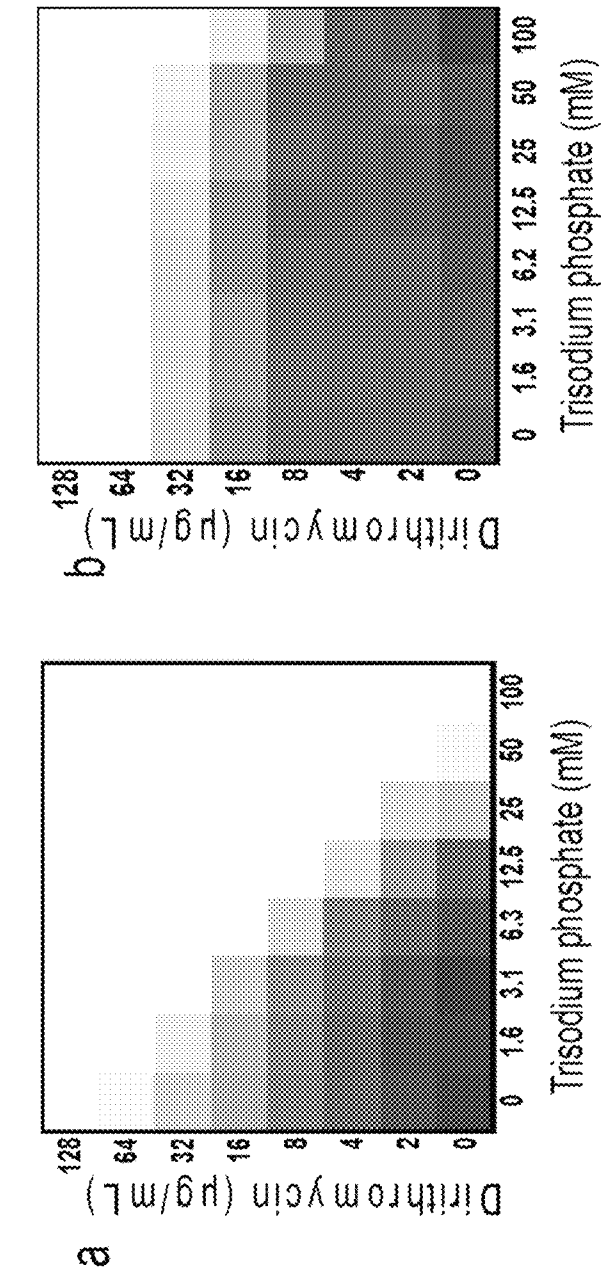
FIG. 19, Panels a-b show the effect of pH-adjusting media on the combination of dirithromycin with trisodium phosphate.

PMF is driven in part by a transmembrane gradient where the periplasmic side of the membrane has a greater concentration of protons. Thus, the addition of buffering agents to alter the external pH can have a significant effect on PMF. To assess the impact of such a perturbation, trisodium phosphate ($Na_3PO_4$) was added, which increased the pH of the media by 3 units and also potentiated the activity of dirithromycin. Adjusting the pH back to neutrality, however, led to a loss of synergy (FIG. 19). FIG. 19, Panels a-b show the effect of pH-adjusting media on the combination of dirithromycin with trisodium phosphate. Shown are microdilution checkerboard analyses for dirithromycin and trisodium phosphate when Panel a) pH is not adjusted to 7.2 (pH ~10) and when Panel b) pH of the medium is adjusted to 7.2. Conversely, supplementation with sodium bicarbonate has little impact on the pH. Steps were taken throughout the studies to confirm that bicarbonate supplemented media were at pH 7.4, and adjusted where necessary. The bicarbonate effect is not a trivial consequence of the pH of the media. Supplementation of the media with a variety of buffer systems indicated that potentiation was unique to bicarbonate.

Figure 21:
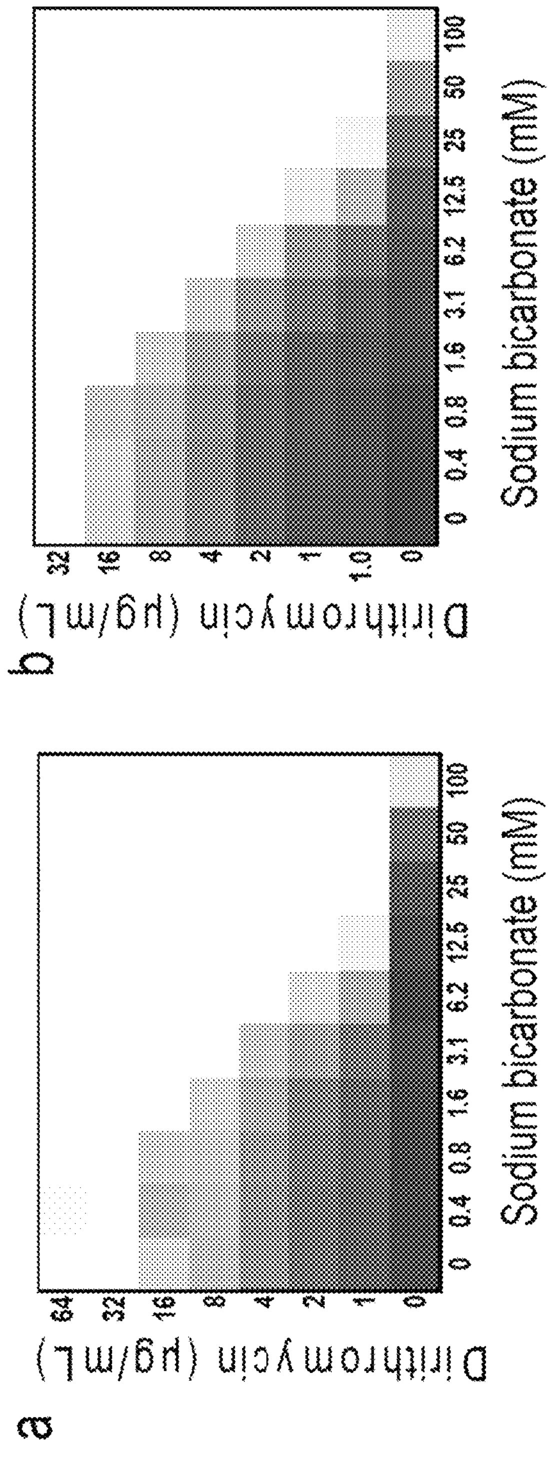
FIG. 21, Panels a-b show the growth inhibition by dirithromycin and sodium bicarbonate. Bacterial strains were wild type *E. coli* in Panel a; and ΔychM in Panel b.
Figure 22:
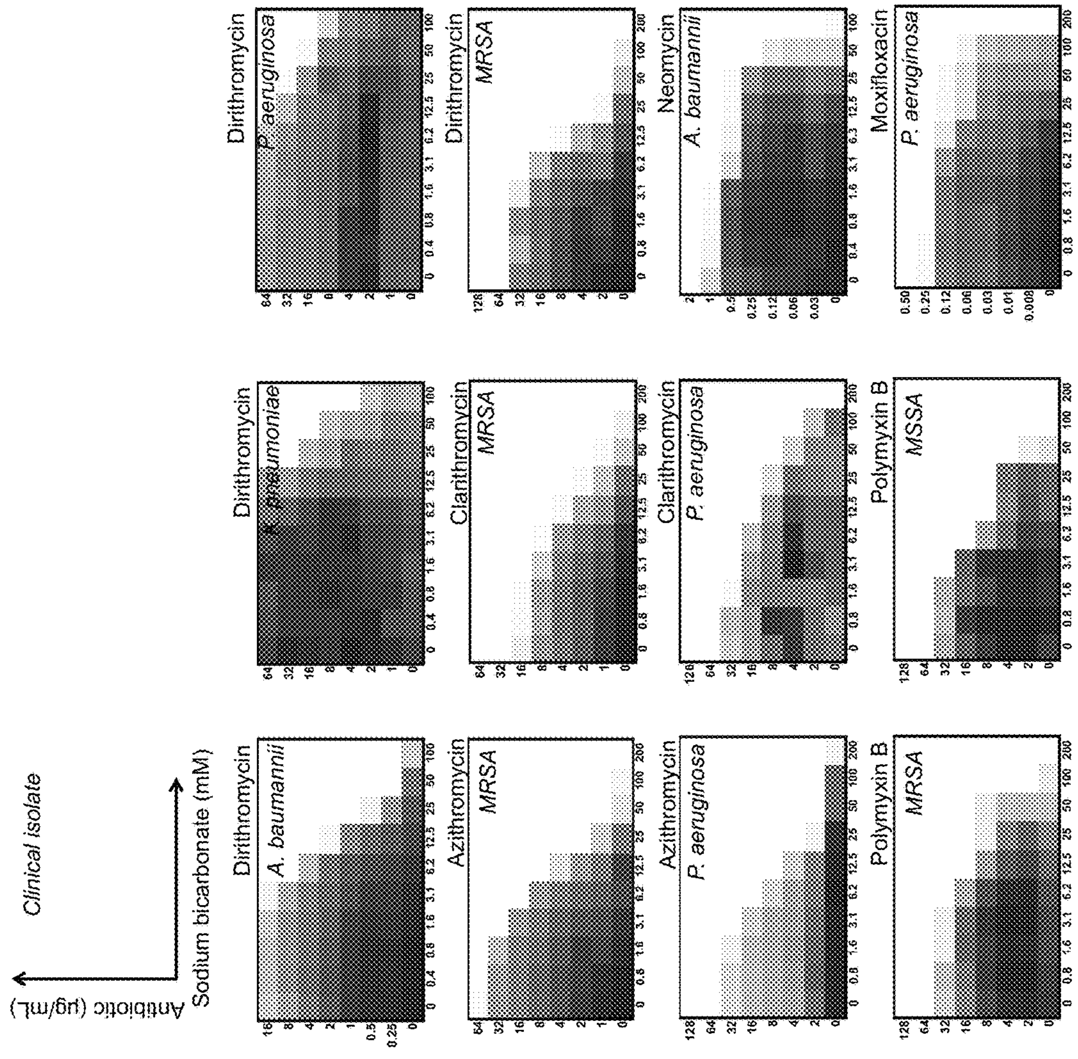
FIG. 22 shows microdilution checkerboard analyses for the effect of varied sodium bicarbonate concentrations on the activity of various antibiotics against clinical isolates of various bacteria. Dark regions represent higher growth of the microorganism. "MRSA" refers to methicillin-resistant *Staphylococcus aureus*. "MSSA" refers to methicillin-sensitive *Staphylococcus aureus.*
Figure 23:
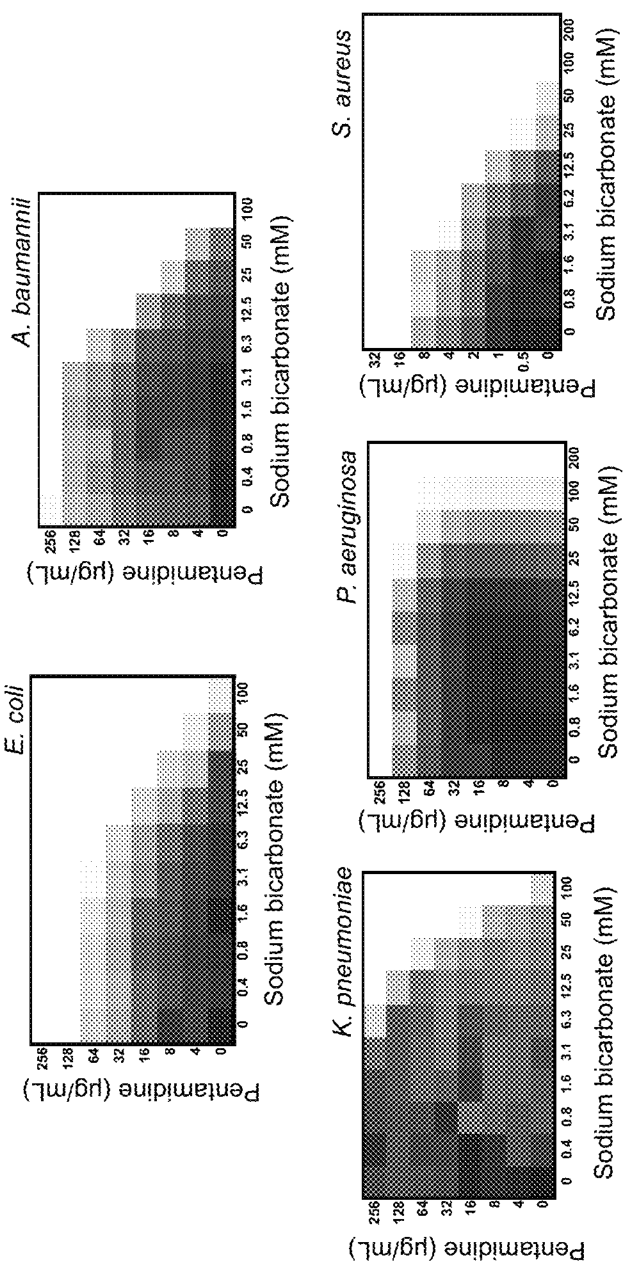
FIG. 23 shows microdilution checkerboard analyses for the effect of varied sodium bicarbonate concentrations on the activity of pentamidine against various bacteria. Dark regions represent higher growth of the microorganism.
Figure 24:
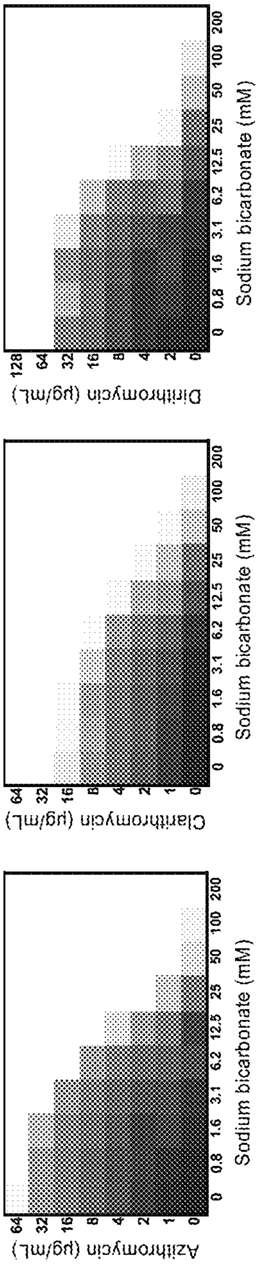
FIG. 24 shows microdilution checkerboard analyses for the effect of varied sodium bicarbonate concentrations on the activity of various macrolides against methicillin-resistant *Staphylococcus aureus* (MRSA). Dark regions represent higher growth of the microorganism.
Figure 25:
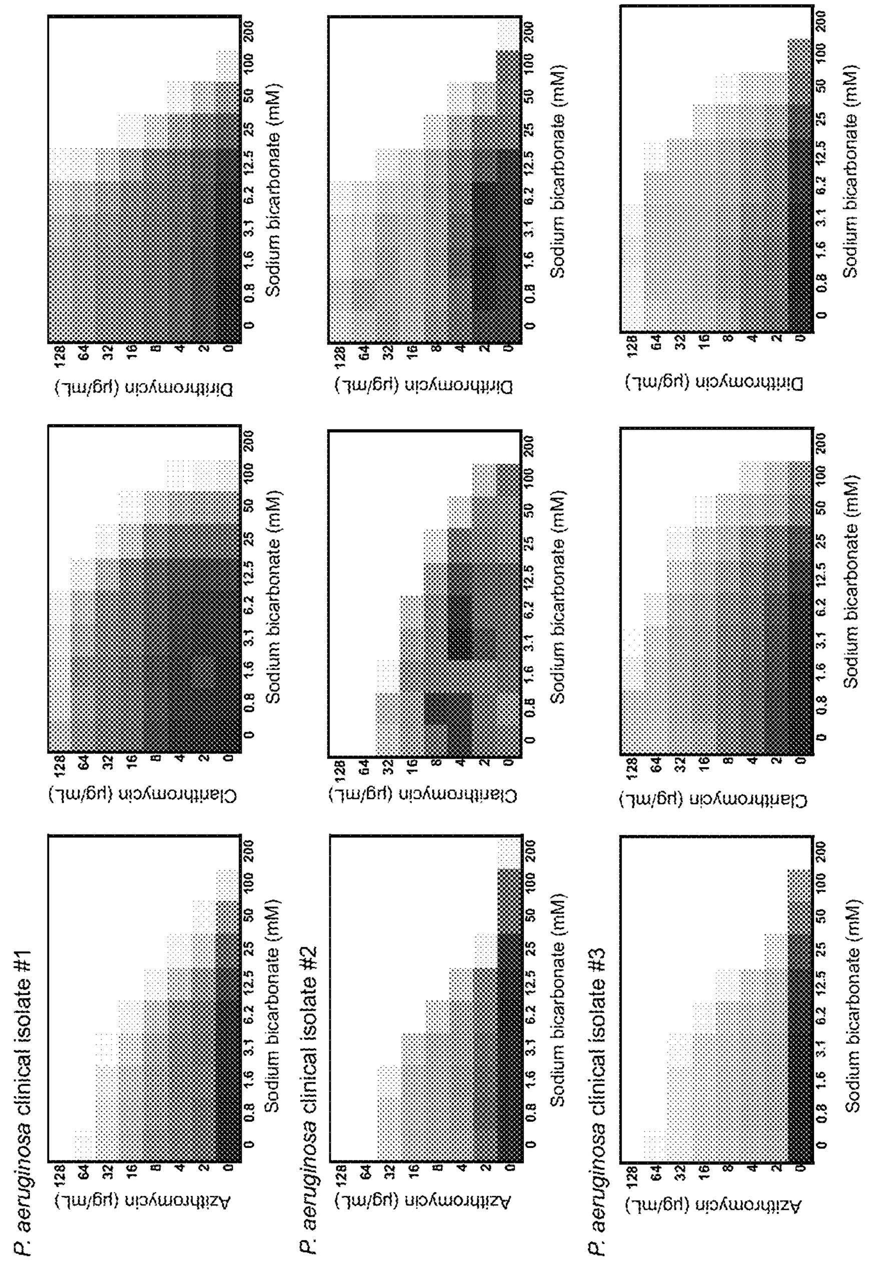
FIG. 25 shows microdilution checkerboard analyses for the effect of varied sodium bicarbonate concentrations on the activity of various macrolides against various clinical isolates of *P. aeruginosa*. Dark regions represent higher growth of the microorganism.

Consistent with the idea that bicarbonate is acting extracytoplasmic, presumably in the periplasmic space, no difference in bicarbonate's ability to potentiate dirithromycin in a bicarbonate transporter-deficient strain (ΔychM) and in a wild-type strain was observed (FIG. 21). FIG. 21, Panels a-b show the growth inhibition by dirithromycin and sodium bicarbonate. Bacterial strains were wild type *E. coli* in Panel a; and ΔychM in Panel b.

Example 19: Data

With respect to pentamidine, taken together these examples show that while pentamidine's in vitro MIC's in standard microbiological media, enforced by the Clinical & Laboratory Standards Institute, discourages its clinical utility, an unforeseen dependence on media conditions revealed an enhanced in vitro activity. The enhanced antibacterial activity of pentamidine depended on the presence of an ionic milieu that is comparable to the conditions found in mammalian tissues and specifically on the presence of bicarbonate. Indeed, the antibacterial activity of pentamidine was potentiated with increasing concentrations of sodium bicarbonate. Pentamidine activity was found to be antagonized in the presence of NaCl, which is present in high concentrations in standard microbiological media. In the presence of a counter ion such as bicarbonate, however, the antibacterial activity of pentamidine was potentiated on average 40-fold against Gram-negative organisms and 50-fold against Gram-positive organisms. Bicarbonate is ubiquitous in the mammalian body and present in high concentrations in various tissues.

Consistently, an unforeseeable efficacy for pentamidine in clearing an *A. baumannii* systemic infection in mice was observed for the first time. The consequence of secondary factors affecting pentamidine's antibacterial activity is consistent with the significant in vivo activity observed.

In addition to diamidines, like pentamidine, many conventional antibiotics also displayed an interaction with bicarbonate. Remarkably, varying classes of conventional antibiotics displayed significant potentiation (macrolides, and some fluoroquinolones) in the presence of physiological concentrations of bicarbonate (25 mM). Significantly, not all conventional antibiotics displayed a synergistic interaction with bicarbonate as some antibiotics resulted in significant suppression of activity (e.g. tetracyclines, some fluoroquinolones, cell wall active antibiotics, amino-coumarins) in the presence of physiological concentrations of bicarbonate (25 mM).

The investigations into the mode of action of bicarbonate revealed an ability to dissipate the pH gradient of the proton motive force across the cytoplasmic membrane. In doing so, bicarbonate suppresses the entry of antibiotics that are driven by the pH gradient and enhances the entry of antibiotics that are driven by the opposing and compensatory component, the membrane potential. Further, by disrupting the energetics across the membrane, bicarbonate also disrupts energy-dependent efflux systems thus further enhancing the accumulation of antibiotics that are actively effluxed. In the case of pentamidine, the latter disrupts the membrane potential across the membrane, thus when used with bicarbonate, both components that make up the proton motive force are synergistically targeted. This phenomenon was also observed with other various small molecules that dissipate membrane potential when used with bicarbonate.

Like bacterial cells, yeast and fungal cells have a cytoplasm and a membrane surrounded by a cell wall. Within the plasma membrane is a chemiosmotic mechanism that is very similar to that of bacteria. In fact, these energetics mechanisms underlie the function of nearly all living organisms. Indeed, energetics via components of proton motive force in yeast and fungi is very similar to that of bacteria and runs at similar values (−150 to −200 mV).

Bicarbonate is present in all body fluids and organs and plays a critical role in maintaining acid-base balance in the human body. Here, to better understand the bacteriostatic mechanism of bicarbonate, its interaction with antimicrobial agents (e.g. antibiotics) of varying mechanisms of action was studied. Many classes of conventional antibiotics displayed significant potentiation or suppression in the presence of physiological concentrations of bicarbonate. All interactions pointed to a mechanism whereby the bicarbonate ion causes perturbation of the pH gradient of proton motive force (PMF) across the cytoplasmic membrane. The product of cellular respiration, PMF, describes the electrochemical potential at the cytoplasmic membrane that is composed of an electrical potential (Δψ, negative inside) and a proton gradient (ΔpH, acidic outside). This electrochemical potential crucially underpins energy production so that bacterial cells work to maintain a constant PMF (Bakker, E. P. & Mangerich, W. E. J Bacteriol 11981, 147: 820-826). Agents that perturb either Δψ or ΔpH are growth inhibitory and prompt a compensatory increase in the other component in order to maintain PMF. Further, synergy in growth inhibition is observed when an agent active on the electrical potential is combined with an agent that targets the proton gradient (Farha et al, Chemistry and Biology 2013, 20:1168-78). Thus in dissipating the pH gradient, bicarbonate had enhancing effects on other antibacterial compounds through distinct mechanisms: (a) Bicarbonate dissipated the pH gradient across the cytoplasmic membrane and led to an increase in the compensatory component, the membrane potential. For antibiotics whose entries are dependent on the membrane potential, an enhancement of growth inhibition was observed in the presence of sodium bicarbonate, consistent with an increase in antibiotic entry. Further, by disrupting the energetics across the membrane, bicarbonate also disrupts energy-dependent efflux thus potentiating the activity of efflux substrates (e.g. macrolides). In these instances, it was observed that bicarbonate led to an increase in intracellular concentration of the antibiotic. (b) In an alternate mechanism, bicarbonate enhanced those compounds that disrupt membrane potential component as a primary mechanism of action. These activities were potentiated via a synergistic collapse of both components of PMF, Δψ by the antibiotic and ΔpH by bicarbonate. In all, by altering the cell's transmembrane pH gradient, bicarbonate potentiates antibiotic activity by increasing the effective intracellular levels of various antibiotics or enhancing their ability to collapse PMF, including pentamidine, an overlooked antibacterial thought to lack in vivo antibacterial activity. Furthermore, it was observed that bicarbonate works together with components of innate immunity (innate immunity factors) to inhibit the growth of bacterial pathogens. In sum, these data implicate bicarbonate as an overlooked potentiator of host immunity in the defense against pathogens. This study suggests that bicarbonate is an overlooked immune factor that may lead to unrecognized in vivo activities of clinically useful antibiotics and a potential natural and innocuous additive in the design of novel therapeutic strategies.

Example 20: The Effect of Bicarbonate on the Activity of Antibiotics

The effect of sodium bicarbonate on the activity of various antibacterial agents was investigated. Clinical isolates of various bacteria were obtained from the American Type Culture Collection (ATCC) and the International Health Management Associates (IHMA). Fractional inhibitory concentration indices (FICIs) were determined by setting up standard checkerboard broth microdilution assays in 96-well microtiter plates with serially diluted 8 (or 10) concentrations of each drug (sodium bicarbonate and the antibacterial agent). The protocol for checkerboard analyses was based on the Clinical & Laboratory Standards Institute (CLSI) guidelines. Plates were incubated at 37° C. for 18 hours, and optical density was read at 600 nm. At least 3 replicates were done for each query compound. Graphical results of these assays are shown in FIGS. 22-25.

The minimum concentration for inhibition (MIC) for each drug was the lowest drug concentration showing <10% growth. The FIC for each drug was calculated as the concentration of drug in the presence of the co-drug for a well showing <10% growth, divided by the MIC for that drug, as shown in the equation below. The FIC index (FICI) is the sum of the two FICs. Chemical-chemical interactions with IBC of less or equal to 0.5 were deemed synergistic.

Fractional Inhibitory Concentration (FIC)=[X]/$MIC_X$, where [X] is the lowest inhibitory concentration of drug in the presence of the co-drug.

Example 21: Administration of Topical Bicarbonate

Mice were infected with *Klebsiella pneumonia* (ATCC 43816; inoculum=$2.5\times10^6$ CFU/mL). Following infection, the infected mice were treated with 4 mL nebulized doses of 225 mM sodium bicarbonate using a chamber nebulizer delivery system (Kent Scientific) at 2, 12 and 24 hours post-infection. The mice were sacrificed after 36 hours, and bacterial counts enumerated. Nebulized bicarbonate was well tolerated at this concentration and all mice had bacterial counts that were lower (in the range of ~$4\times10^4$-$4\times10^5$ CFU/mL) as compared to that of the starting inoculum ($2.5\times10^6$ CFU/mL).

All publications, patents and patent applications are herein incorporated by reference in their entirety to the same extent as if each individual publication, patent or patent application was specifically and individually indicated to be incorporated by reference in its entirety. Where a term provided herein is found to be defined differently in a document incorporated herein by reference, the definition provided herein is to serve as the definition for the term.

The invention claimed is:

1. A method for inhibiting the growth of a bacterium, comprising contacting the bacterium with an effective amount of (i) bicarbonate and (ii) an antimicrobial agent, wherein the antimicrobial agent is azithromycin, and the effective amount of the bicarbonate is a concentration of greater than 150 mM.

2. The method of claim 1, wherein the effective amount of the bicarbonate is greater than 175 mM.

3. The method of claim 1, wherein the effective amount of the bicarbonate is 175 mM to 200 mM.

4. The method of claim 1, wherein the bicarbonate is sodium bicarbonate, ammonium bicarbonate, lithium bicarbonate, potassium bicarbonate, magnesium bicarbonate, calcium bicarbonate or zinc bicarbonate.

5. The method of claim 1, wherein the bicarbonate is present in a first composition and the antimicrobial agent is present in a second composition.

6. The method of claim 1, wherein the bacterium is a Gram negative bacterium.

7. The method of claim 1, wherein the bacterium is a Gram positive bacterium.

8. The method of claim 1, wherein the bacterium is a species of *Acetobacter, Acinetobacter, Actinomyces, Aerococcus, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Lactococcus, Legionella, Listeria, Methanobacterium, Microbacterium, Micrococcus, Moraxella, Mycobacterium, Mycoplasma, Neisseria, Pasteurella, Pediococcus, Peptostreptococcus, Porphyromonas, Prevotella, Pseudomonas, Rhizobium, Rickettsia, Rochalimaea, Rothia, Salmonella, Serratia, Shigella, Sarcina, Spirillum, Spirochaetes, Staphylococcus, Stenotrophomonas, Streptobacillus, Streptococcus, Tetragenococcus, Treponema, Vibrio, Viridans, Wolbachia* or *Yersinia.*

9. The method of claim 1, wherein the bacterium is *Pseudomonas aeruginosa.*

10. The method of claim 1, wherein the bacterium is *Staphylococcus aureus.*

11. The method of claim 1, wherein the bicarbonate is administered topically, and the antimicrobial agent is administered orally.

12. The method of claim 11, wherein the bicarbonate is administered intranasally.

13. The method of claim 11, wherein the bicarbonate is administered as an aerosol or nebulized spray.

14. A kit comprising i) a first bicarbonate composition and ii) a second antimicrobial composition, wherein the first composition comprises bicarbonate in an amount of greater than 150 mM and a pharmaceutically acceptable carrier, and the second composition comprises an antimicrobial agent azithromycin.

15. The kit of claim 14, wherein the first composition is prepared for administration topically, and the second composition is prepared for oral administration.

16. The kit of claim 14, wherein the first composition is an aerosol or nebulized spray.

17. The kit of claim 14, wherein the amount of the bicarbonate is greater than 175 mM.

18. The kit of claim 14, wherein the amount of the bicarbonate is an amount of 175 mM to 200 mM.

* * * * *